US012567211B2

(12) United States Patent
Wang et al.

(10) Patent No.: US 12,567,211 B2
(45) Date of Patent: Mar. 3, 2026

(54) HEALTH MANAGEMENT SYSTEM, AND HUMAN BODY INFORMATION DISPLAY METHOD AND HUMAN BODY MODEL GENERATION METHOD APPLIED TO SAME

(71) Applicant: BOE TECHNOLOGY GROUP CO., LTD., Beijing (CN)

(72) Inventors: Bingdong Wang, Beijing (CN); Hua Bai, Beijing (CN); Yunan Wang, Beijing (CN); Limin Yang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 18/762,194

(22) Filed: Jul. 2, 2024

(65) Prior Publication Data

US 2024/0362866 A1      Oct. 31, 2024

Related U.S. Application Data

(63) Continuation of application No. 17/756,285, filed as application No. PCT/CN2020/131439 on Nov. 25, 2020, now Pat. No. 12,141,923.

(30) Foreign Application Priority Data

Nov. 25, 2019   (CN) .......................... 201911167949.X
Nov. 25, 2019   (CN) .......................... 201911168892.5
(Continued)

(51) Int. Cl.
*G06T 19/00*         (2011.01)
*G06F 3/04815*       (2022.01)
(Continued)

(52) U.S. Cl.
CPC .......... *G06T 19/00* (2013.01); *G06F 3/04815* (2013.01); *G06F 3/04845* (2013.01);
(Continued)

(58) Field of Classification Search
None
See application file for complete search history.

(56) References Cited

U.S. PATENT DOCUMENTS 10,089,555 B2 *  10/2018  Russell ................ G06V 30/133
10,832,472 B2    11/2020  Mok et al.
(Continued)

FOREIGN PATENT DOCUMENTS

CN          102354347 A      2/2012
CN          102411675 A      4/2012
(Continued)

OTHER PUBLICATIONS

First Office Action received for Chinese Patent Application No. 201911168906.3, mailed on May 23, 2024, 16 pages (7 pages of English Translation and 9 pages of Original Document).
(Continued)

*Primary Examiner* — Saptarshi Mazumder
(74) *Attorney, Agent, or Firm* — Calfee, Halter & Griswold LLP

(57)          ABSTRACT

A health management system, including: a health assessment module configured to obtain human health-related health parameter information of a user, and generate a health condition assessment result on the basis of the health parameter information; a health intervention module configured to generate a health management plan on the basis of the health condition assessment result; a human body model generation module configured to generate a human body model that can be displayed on a display interface; and a human body information display model configured to: obtain at least one
(Continued)

first display instruction each corresponding to one human body system model of a plurality of human body system models medically classified according to human body systems, and display, on the display interface, the three-dimensional human body model in the form of layers based on the human body system model corresponding to the at least one first display instruction.

17 Claims, 20 Drawing Sheets

(30)       Foreign Application Priority Data

Nov. 25, 2019   (CN) .......................... 201911168906.3
Nov. 9, 2020    (CN) .......................... 202011242331.8

(51) Int. Cl.
    *G06F 3/04845*       (2022.01)
    *G06T 17/00*         (2006.01)
    *G16H 50/30*         (2018.01)
    *G06F 3/0488*        (2022.01)
(52) U.S. Cl.
    CPC ............. *G06T 17/00* (2013.01); *G16H 50/30* (2018.01); *G06F 3/0488* (2013.01); *G06T 2200/24* (2013.01); *G06T 2210/41* (2013.01); *G06T 2219/004* (2013.01)

(56)            References Cited

U.S. PATENT DOCUMENTS

| | | | |
|---|---|---|---|
| 2010/0167254 A1 | 7/2010 | Nguyen | |
| 2011/0169927 A1 | 7/2011 | Mages et al. | |
| 2011/0179389 A1* | 7/2011 | Douen ................... | G16H 70/60 707/769 |
| 2011/0313479 A1 | 12/2011 | Rubin | |
| 2017/0329905 A1* | 11/2017 | Passerini .................. | G06N 5/04 |
| 2017/0337350 A1* | 11/2017 | Kim .................... | G06F 3/04815 |
| 2019/0105105 A1 | 4/2019 | Zagorchev et al. | |
| 2019/0228581 A1* | 7/2019 | Dascola .............. | G06F 3/04886 |
| 2019/0371082 A1 | 12/2019 | Guo et al. | |
| 2020/0004328 A1 | 1/2020 | Blume et al. | |

FOREIGN PATENT DOCUMENTS

| | | | |
|---|---|---|---|
| CN | 102722338 A | | 10/2012 |
| CN | 104834824 A | | 8/2015 |
| CN | 105725964 A | | 7/2016 |
| CN | 105893778 A | | 8/2016 |
| CN | 107038750 A | | 8/2017 |
| CN | 107154071 A | | 9/2017 |
| CN | 108564612 A | | 9/2018 |
| CN | 109409348 A | | 3/2019 |
| CN | 109427083 A | | 3/2019 |
| CN | 109620407 A | | 4/2019 |
| CN | 109829971 A | | 5/2019 |
| CN | 109994198 A | | 7/2019 |
| CN | 110136243 A | | 8/2019 |
| CN | 110148209 A | | 8/2019 |
| CN | 110364262 A | | 10/2019 |
| JP | 2005-256232 A | | 9/2005 |
| KR | 10-2018-0064907 A | | 6/2018 |
| WO | 2013/120454 A1 | | 8/2013 |

OTHER PUBLICATIONS

First Office Action received for Chinese Patent Application No. 202011242331.8, mailed on May 24, 2024, 16 pages (7 pages of English Translation and 9 pages of Original Document).

International Preliminary Report on Patentability received for PCT Patent Application No. PCT/CN2020/131439, mailed on Jun. 9, 2022, 14 pages (8 pages of English Translation and 6 pages of Original Document).

International Search Report and Written Opinion received for PCT Patent Application No. PCT/CN2020/131439, mailed on Mar. 1, 2021, 18 pages (9 pages of English Translation and 9 pages of Original Document).

Non-Final Office Action received for U.S. Appl. No. 17/756,285, mailed on Feb. 16, 2024, 33 pages.

Notice of Allowance received for U.S. Appl. No. 17/756,285, mailed on Jun. 12, 2024, 17 pages.

Office Action received for Chinese Patent Application No. 201911167949.X, mailed on Jan. 24, 2022, 15 pages (8 pages of English Translation and 7 pages of Office Action).

Rejection Decision received for Chinese Patent Application No. 201911167949.X, mailed on Mar. 4, 2023, 22 pages (13 pages of English Translation and 9 pages of Original Document).

Second Office Action received for Chinese Patent Application No. 201911167949.X, mailed on Dec. 5, 2022, 13 pages (7 pages of English Translation and 8 pages of Original Document).

\* cited by examiner

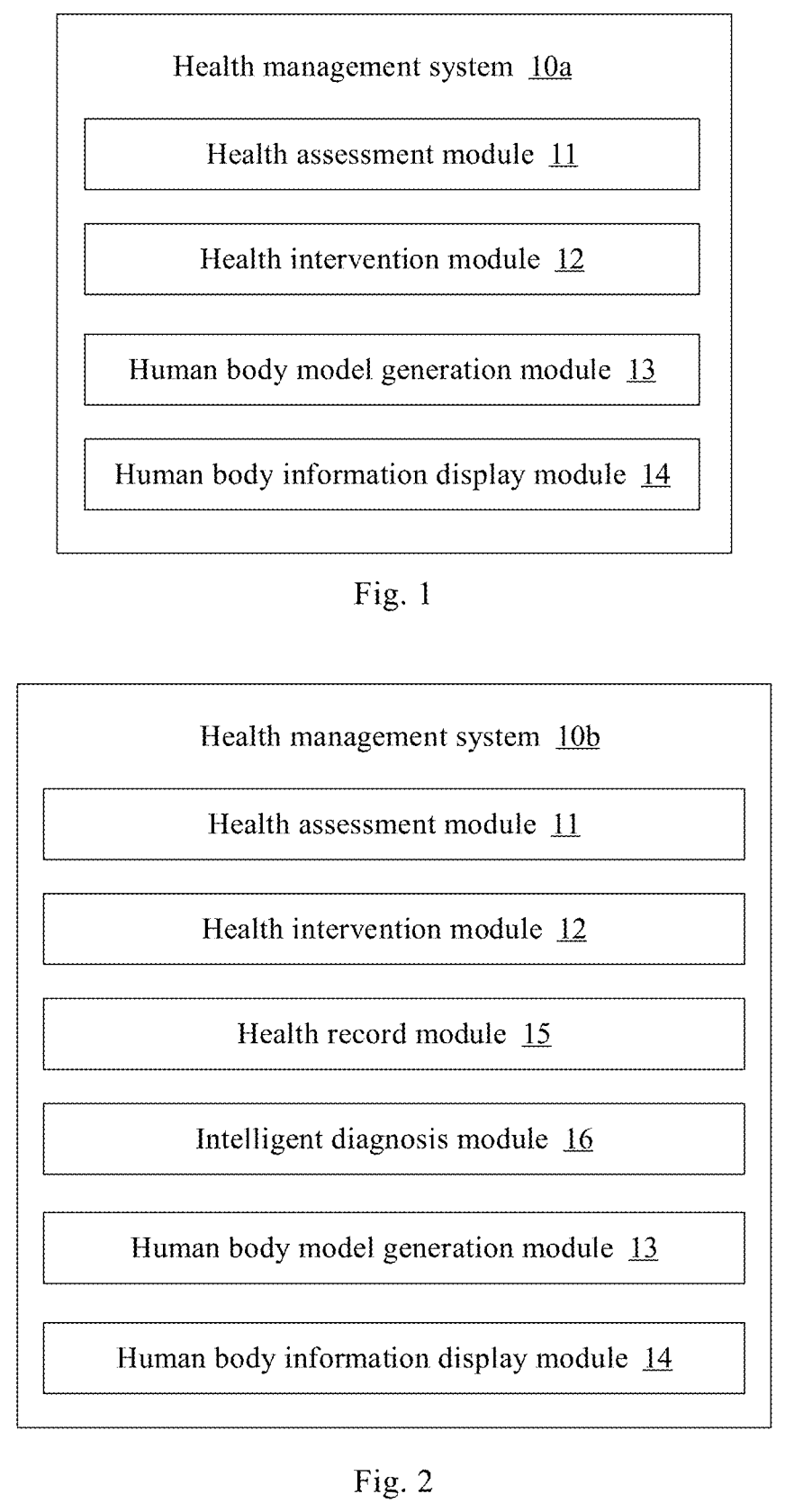

Health management system  10a

Health assessment module  11

Health intervention module  12

Human body model generation module  13

Human body information display module  14

Fig. 1

Health management system  10b

Health assessment module  11

Health intervention module  12

Health record module  15

Intelligent diagnosis module  16

Human body model generation module  13

Human body information display module  14

Displaying at least one human body information tag on the display interface ⟋— S2010

Obtaining a trigger instruction for one human body information tag, and prominently displaying, on the display interface, at least the local model of the three-dimensional human body model or the human body information corresponding to the human body information tag ⟋— S2200

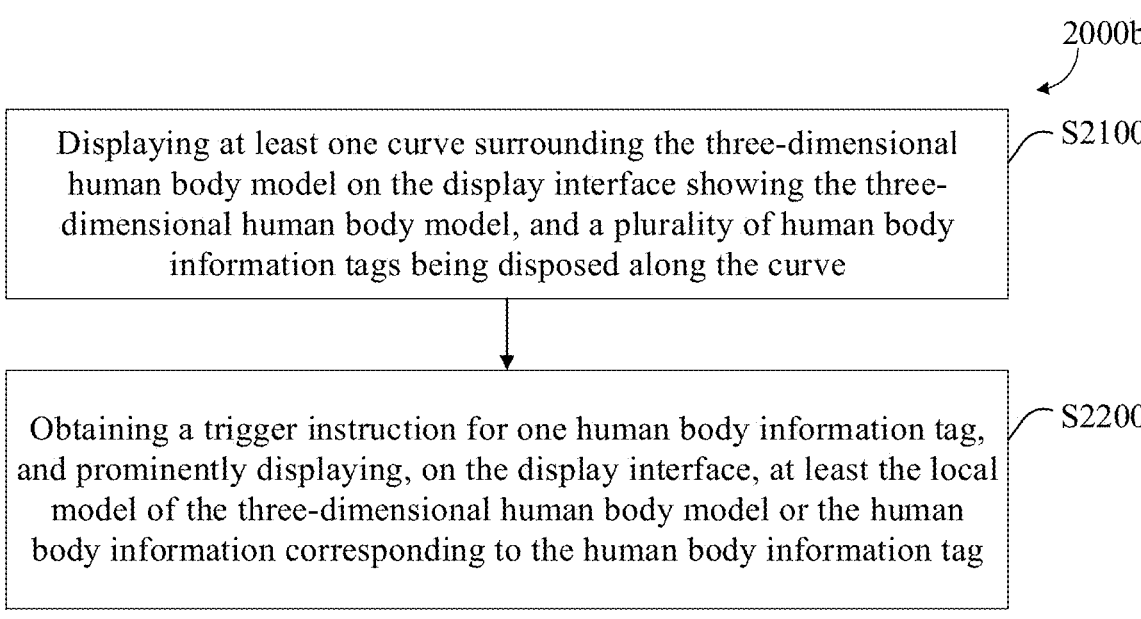

2000b

| Displaying at least one curve surrounding the three-dimensional human body model on the display interface showing the three-dimensional human body model, and a plurality of human body information tags being disposed along the curve | S2100 |

| Obtaining a trigger instruction for one human body information tag, and prominently displaying, on the display interface, at least the local model of the three-dimensional human body model or the human body information corresponding to the human body information tag | S2200 |

Fig. 9

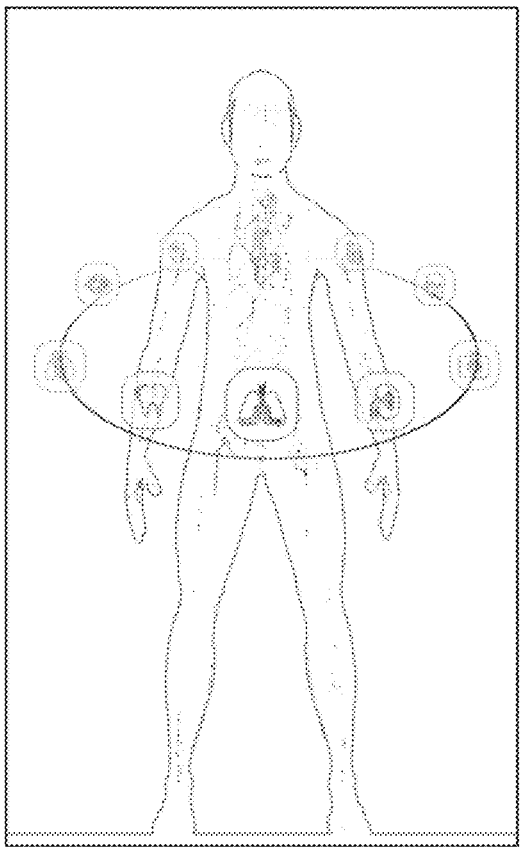

Fig. 10A

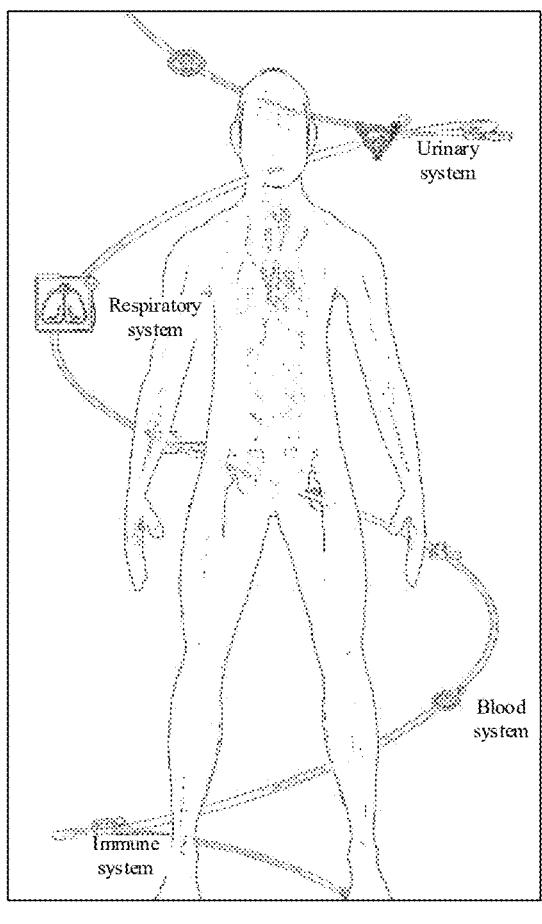

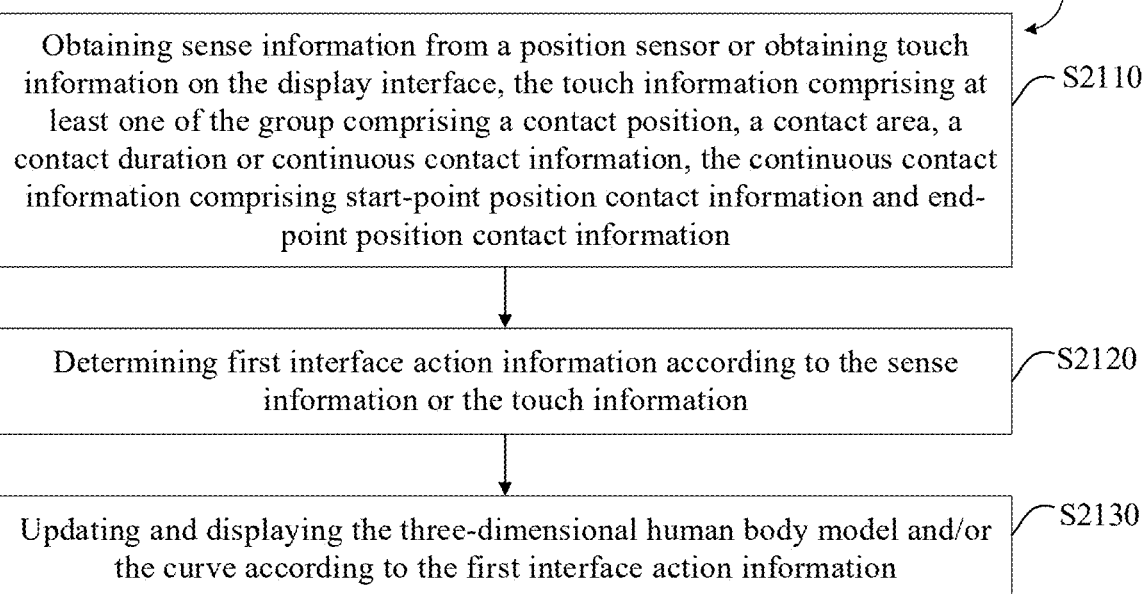

Obtaining sense information from a position sensor or obtaining touch information on the display interface, the touch information comprising at least one of the group comprising a contact position, a contact area, a contact duration or continuous contact information, the continuous contact information comprising start-point position contact information and end-point position contact information    S2110

Determining first interface action information according to the sense information or the touch information    S2120

Updating and displaying the three-dimensional human body model and/or the curve according to the first interface action information    S2130

Fig. 11

Blood system     Anomaly Index
Number of RBC increases ...

Immune system     Disease >
Number of RBC increases ...

Blood system     Anomaly Index >
Number of RBC increases ...

Immune system     Disease >
Number of RBC increases ...

Blood system     Anomaly Index >
Number of RBC increases ...

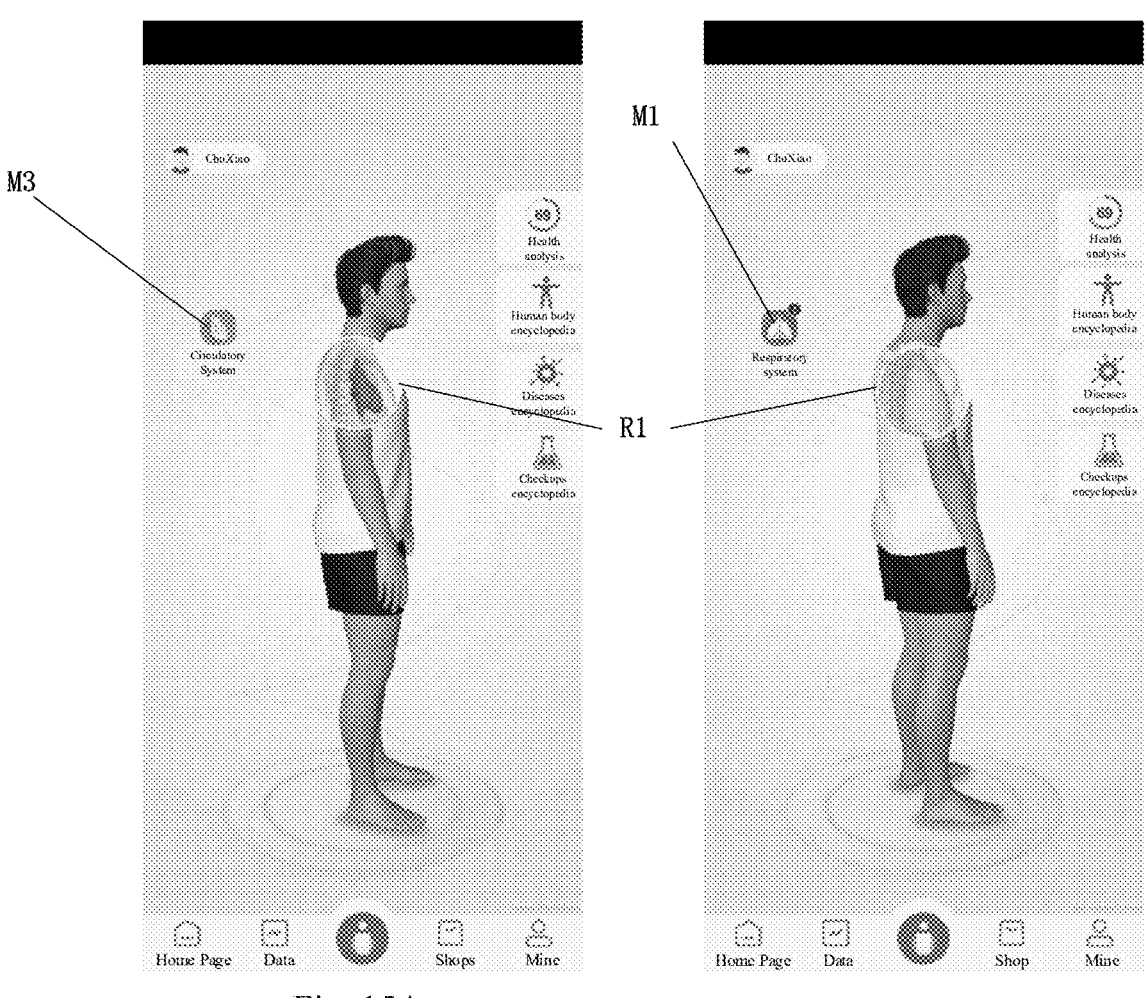
Fig. 15A                                    Fig. 15B
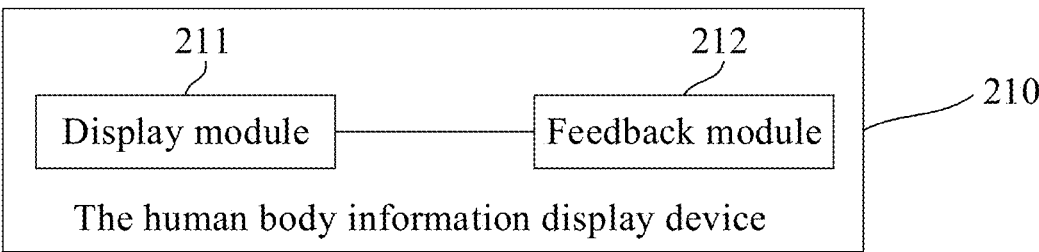
Fig. 16

3000a

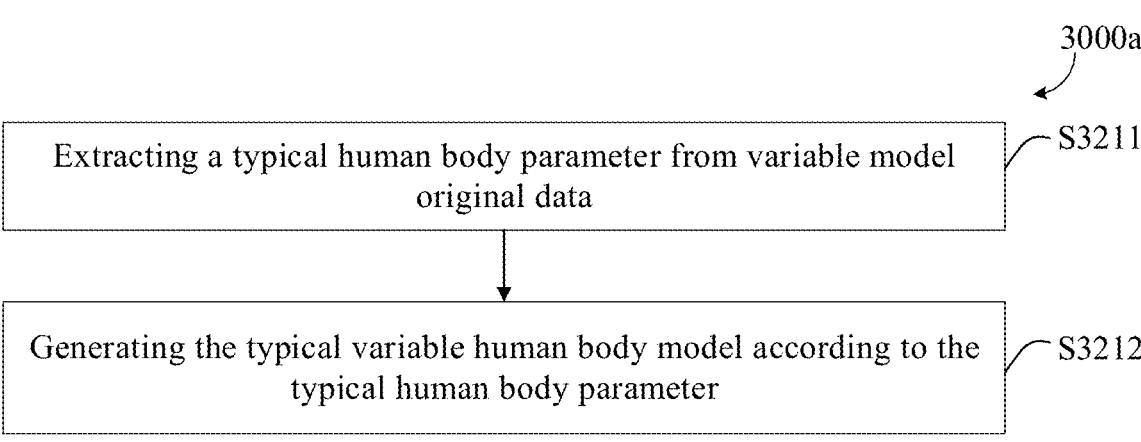

Extracting a typical human body parameter from variable model original data — S3211

Generating the typical variable human body model according to the typical human body parameter — S3212

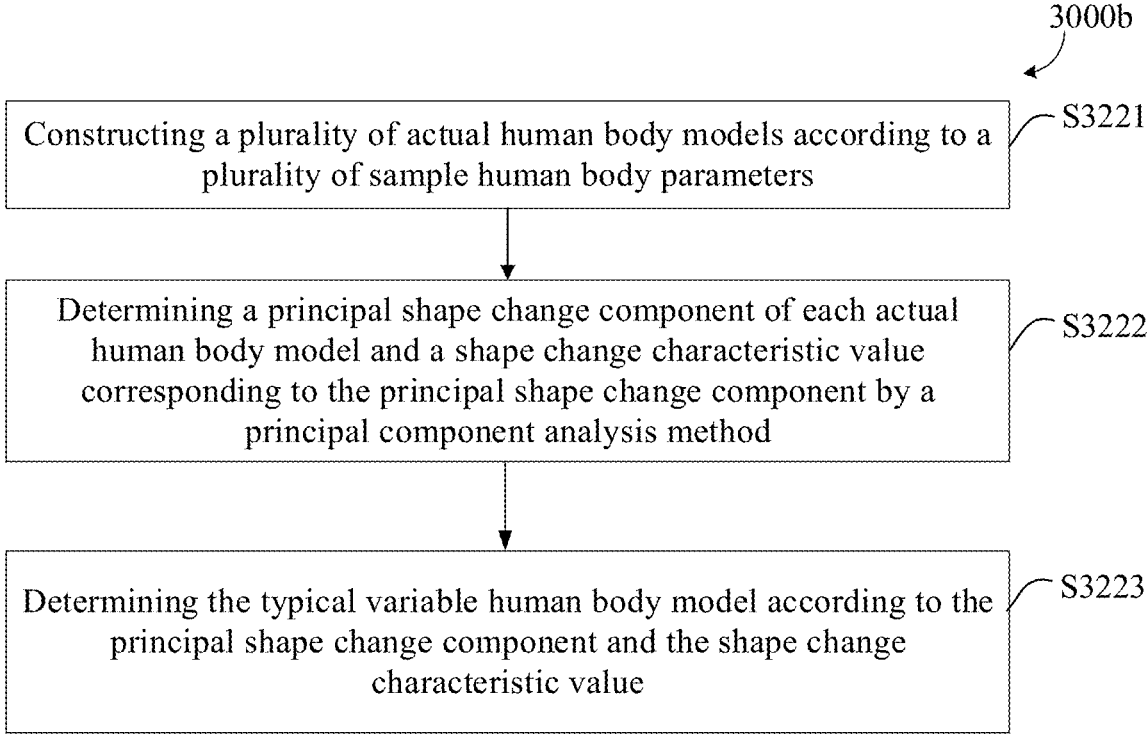

Constructing a plurality of actual human body models according to a plurality of sample human body parameters — S3221

Determining a principal shape change component of each actual human body model and a shape change characteristic value corresponding to the principal shape change component by a principal component analysis method — S3222

Determining the typical variable human body model according to the principal shape change component and the shape change characteristic value — S3223

Fig. 19B

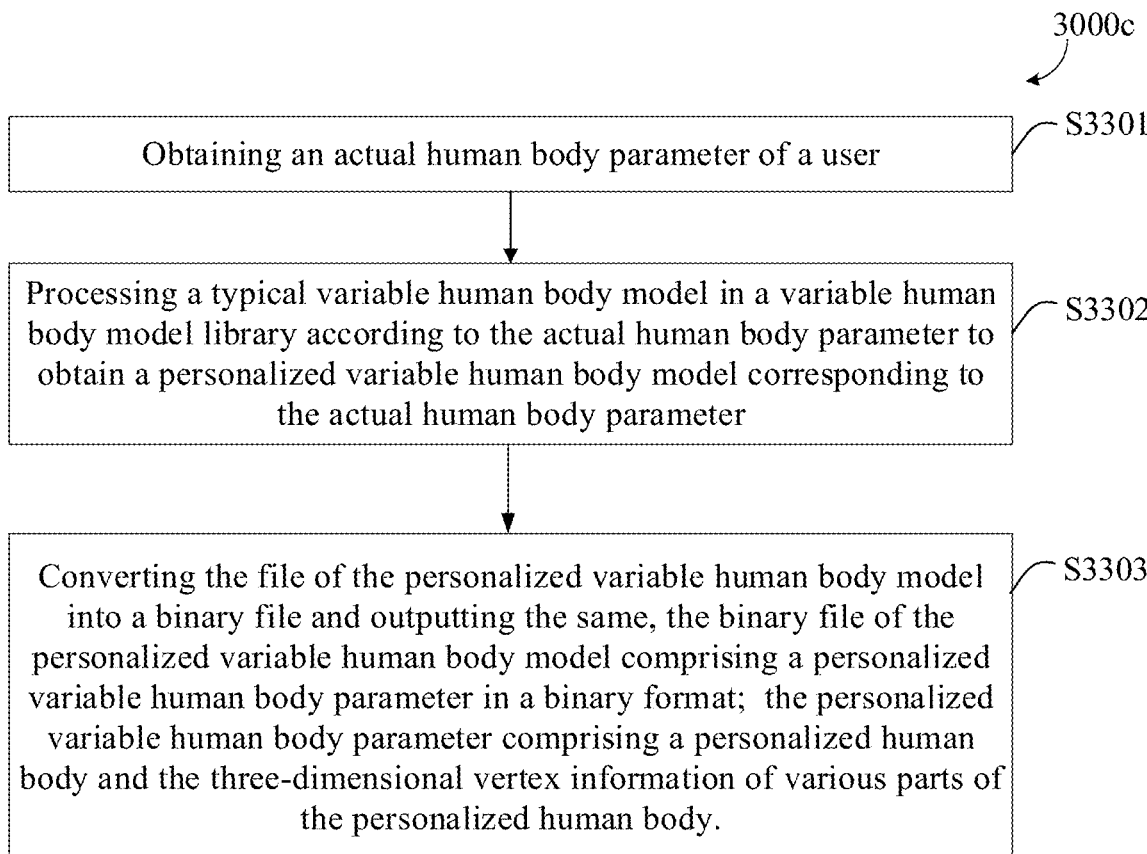

3000c

Obtaining an actual human body parameter of a user ⟋ S3301

Processing a typical variable human body model in a variable human body model library according to the actual human body parameter to obtain a personalized variable human body model corresponding to the actual human body parameter ⟋ S3302

Converting the file of the personalized variable human body model into a binary file and outputting the same, the binary file of the personalized variable human body model comprising a personalized variable human body parameter in a binary format; the personalized variable human body parameter comprising a personalized human body and the three-dimensional vertex information of various parts of the personalized human body. ⟋ S3303

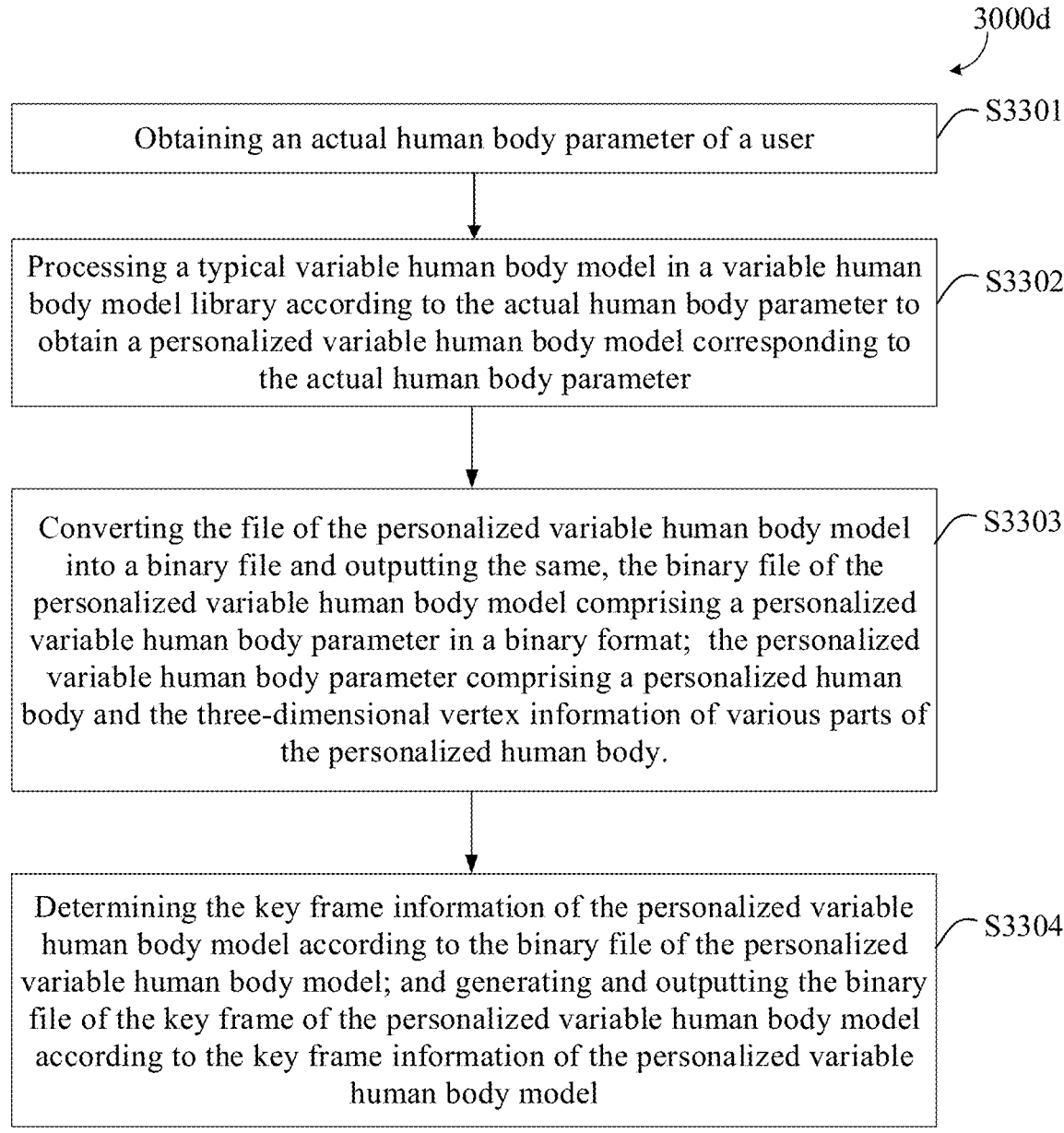

Obtaining an actual human body parameter of a user    S3301

Processing a typical variable human body model in a variable human body model library according to the actual human body parameter to obtain a personalized variable human body model corresponding to the actual human body parameter    S3302

Converting the file of the personalized variable human body model into a binary file and outputting the same, the binary file of the personalized variable human body model comprising a personalized variable human body parameter in a binary format; the personalized variable human body parameter comprising a personalized human body and the three-dimensional vertex information of various parts of the personalized human body.    S3303

Determining the key frame information of the personalized variable human body model according to the binary file of the personalized variable human body model; and generating and outputting the binary file of the key frame of the personalized variable human body model according to the key frame information of the personalized variable human body model    S3304

Fig. 20B

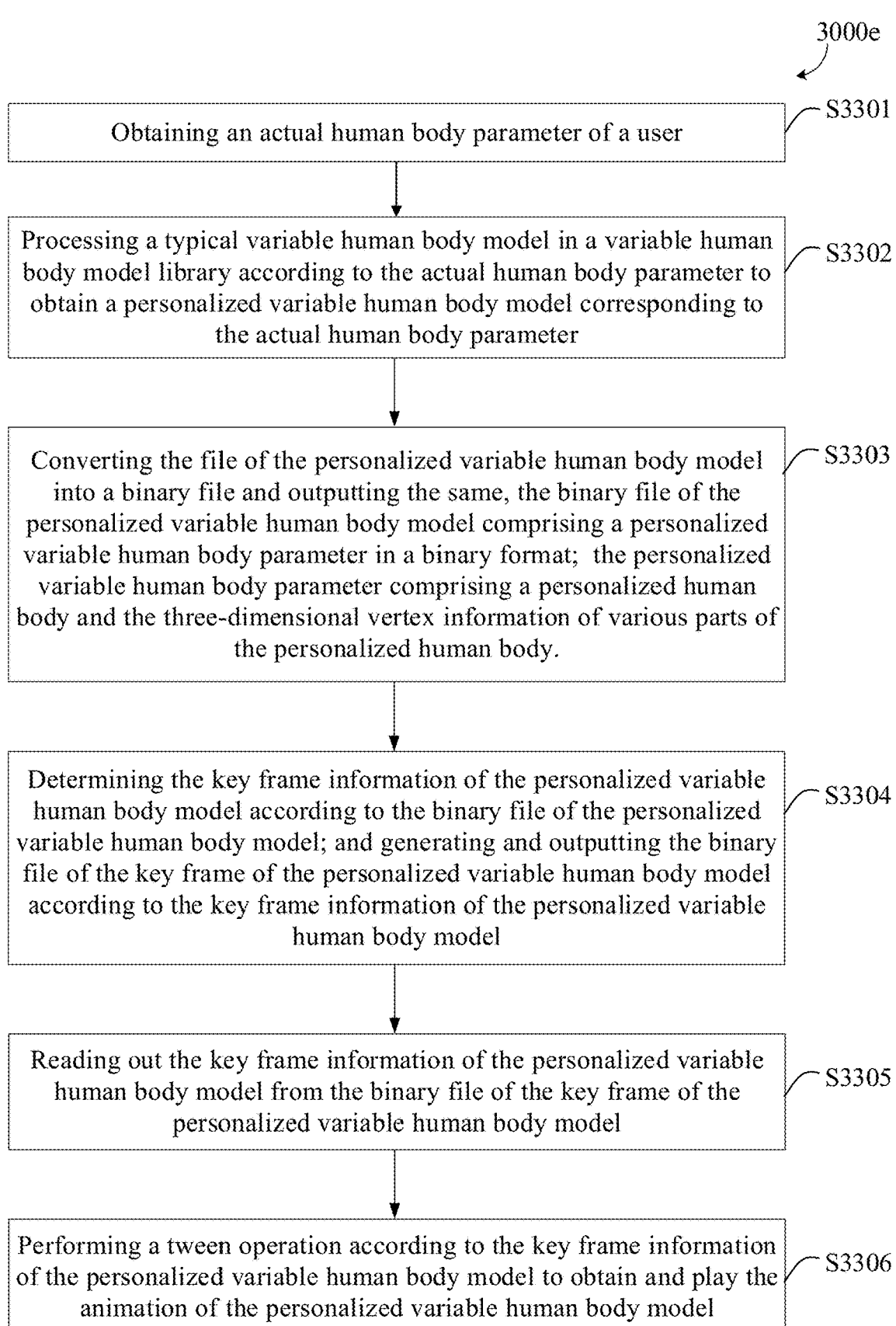

3000e

Obtaining an actual human body parameter of a user ⟋ S3301

Processing a typical variable human body model in a variable human body model library according to the actual human body parameter to obtain a personalized variable human body model corresponding to the actual human body parameter ⟋ S3302

Converting the file of the personalized variable human body model into a binary file and outputting the same, the binary file of the personalized variable human body model comprising a personalized variable human body parameter in a binary format; the personalized variable human body parameter comprising a personalized human body and the three-dimensional vertex information of various parts of the personalized human body. ⟋ S3303

Determining the key frame information of the personalized variable human body model according to the binary file of the personalized variable human body model; and generating and outputting the binary file of the key frame of the personalized variable human body model according to the key frame information of the personalized variable human body model ⟋ S3304

Reading out the key frame information of the personalized variable human body model from the binary file of the key frame of the personalized variable human body model ⟋ S3305

Performing a tween operation according to the key frame information of the personalized variable human body model to obtain and play the animation of the personalized variable human body model ⟋ S3306

Fig. 20C

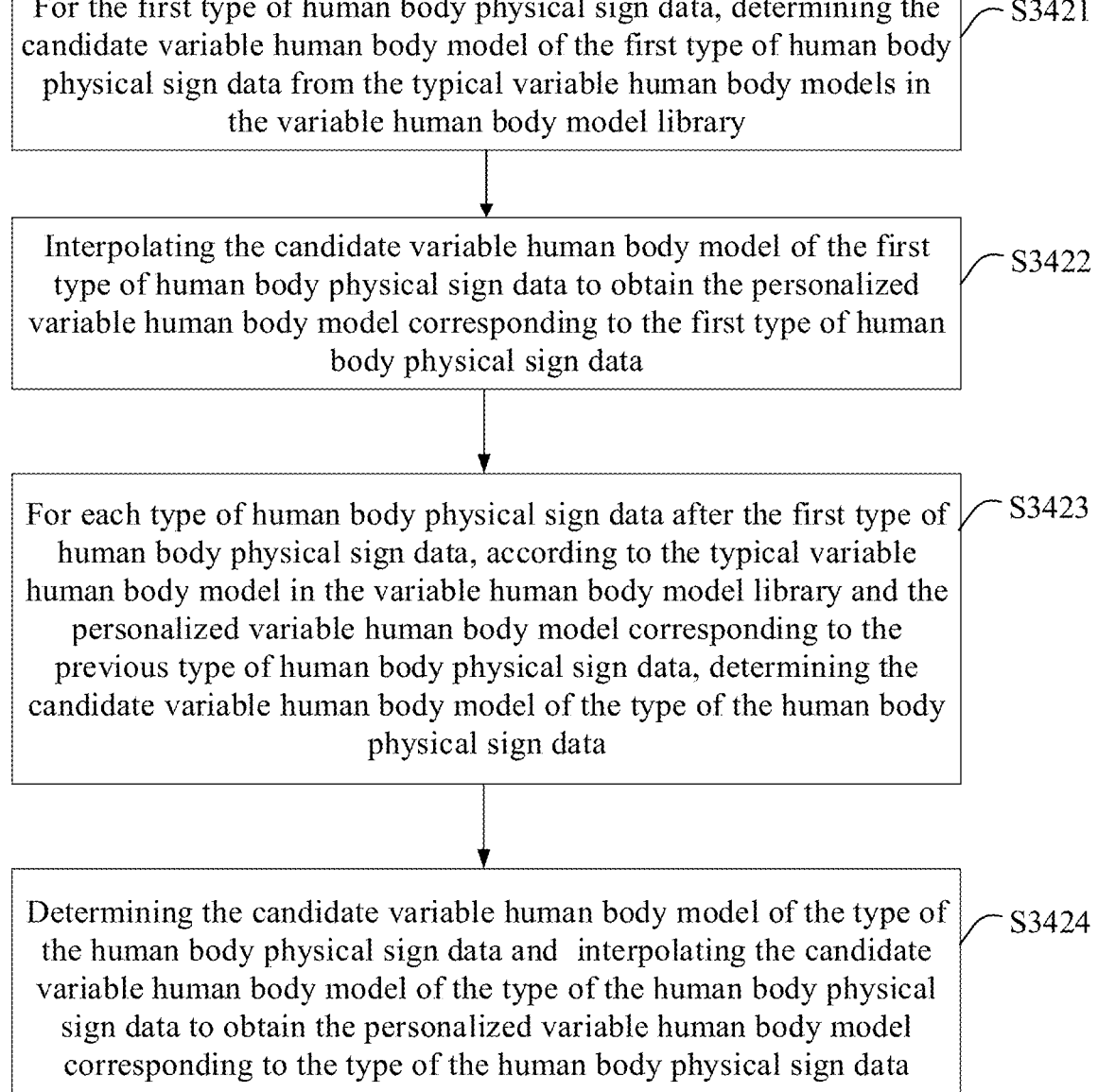

For the first type of human body physical sign data, determining the candidate variable human body model of the first type of human body physical sign data from the typical variable human body models in the variable human body model library ⟋⟋ S3421

Interpolating the candidate variable human body model of the first type of human body physical sign data to obtain the personalized variable human body model corresponding to the first type of human body physical sign data ⟋⟋ S3422

For each type of human body physical sign data after the first type of human body physical sign data, according to the typical variable human body model in the variable human body model library and the personalized variable human body model corresponding to the previous type of human body physical sign data, determining the candidate variable human body model of the type of the human body physical sign data ⟋⟋ S3423

Determining the candidate variable human body model of the type of the human body physical sign data and interpolating the candidate variable human body model of the type of the human body physical sign data to obtain the personalized variable human body model corresponding to the type of the human body physical sign data ⟋⟋ S3424

Fig. 21B

HEALTH MANAGEMENT SYSTEM, AND HUMAN BODY INFORMATION DISPLAY METHOD AND HUMAN BODY MODEL GENERATION METHOD APPLIED TO SAME

RELATED APPLICATIONS

This application is a continuation of U.S. patent application Ser. No. 17/756,285, filed on May 20, 2022, which is a 35 U.S.C. 371 U.S. national phase entry of PCT/CN2020/131439 with an international filing date of Nov. 25, 2020.

TECHNICAL FIELD

The present disclosure relates to the field of computer technology, and specifically to a health management system, a human body information display method and a human body model generation method therefor, and corresponding devices and computer-readable storage medium.

BACKGROUND

With the progress of society and the gradual improvement of living standards, people's health awareness and disease prevention awareness are constantly enhanced, and health management is becoming more and more important in people's lives. However, at the current stage, users only pay attention to the particular health parameter(s) of the human body, or do not know the impact of the contents of various physical examination items in the physical examination report on their own health status after the completion of the physical examination, which makes them unable or neglect to assess their own health status; or, although they know their own health status, they do not know how to take effective measures to intervene. In addition, due to the inconveniences of data collection and sorting, users often do not tend to preserve and manage health history data.

In addition, after decades of development, human body models have experienced the process from single sample to multi sample and from static state to dynamic state. However, current human body models are still insufficient. First of all, the number of human body samples included in a human body model is still limited. For example, at present, the human body model with the greatest number of samples only includes 10 human body samples, which can only provide a small number of samples of different ages, heights and weights, but cannot reflect the statistical rules of anatomical deformation in the population, cannot be used to generate a personalized human body variable model, or generates a low-precise personalized human body variable model. If the personalized human body variable model is calculated by a conventional statistical method, it will occupy a lot of computing resources, require high computing and time costs and have narrow applicability.

It should be understood that human body is an extremely complex integrated organic system. In order to effectively monitor their own health status, people must have a clear and accurate understanding of the human body. Based on the existing anatomical knowledge and display technology, people can understand the entire human body and the composition of various parts. However, in the field of human body models, a complex human body model is often displayed with various organs or tissues mutually penetrated or occluded, thereby rendering it difficult to observe and operate, which is unfavourable for the ordinary people without professional medical knowledge to clearly understand the human body information. In addition, everyone has unique individual characteristics, such that each human body is a unique system, and the system has been undergoing dynamic changes. Therefore, with the help of the existing technologies, it is difficult to accurately and truly display everyone's human body information, such as the spatial position of each system in the human body or the mutual relationships between the systems, nor is it possible to freely realize interactive cognition of the displayed human body information, that is, conveniently and quickly checking the human body information dynamically from any angle according to the user's own will.

SUMMARY

According to an aspect of the present application, there is provided a health management system, including a health assessment module configured to obtain health parameter information related to human body health of a user, and generate the health status assessment result of the user based on the health parameter information; a health intervention module configured to generate a health management scheme of the user based on the health status assessment result; a human body model generation module configured to generate a human body model displayable on a display interface; and a human body information display module configured to display the human body model on the display interface based on human body tissue layers, human body systems or human body parts according to received display instructions.

According to some exemplary embodiments, the health assessment module identifies the user's physical examination report so as to obtain health parameter information related to human body health of the user.

According to some exemplary embodiments, at least one of the health assessment module and the health intervention module is configured to monitor physiological indicators reflecting the health status of the user.

According to some exemplary embodiments, at least one of the health assessment module and the health intervention module is further configured to push a message to the user.

According to some exemplary embodiments, there is provided a human body information display method for displaying the human body model in the health management system, including the steps of: obtaining at least one first display instruction each corresponding to one of a plurality of tissue layer models classified according to the human body tissue layers, and displaying, on the display interface, the human body model in the form of the tissue layer model corresponding to the at least one first display instruction; and/or obtaining at least one second display instruction each corresponding to one of a plurality of human body system models classified according to the human body systems, and displaying, on the display interface, the human body model in the form of the human body system model corresponding to the at least one second display instruction; and/or obtaining at least one third display instruction each corresponding to one of a plurality of local human body models classified according to the human body parts, and displaying, on the display interface, the human body model in the form of the local human body model corresponding to the at least one third display instruction.

According to some exemplary embodiments, the first display instruction, the second display instruction and the third display instruction are obtained by at least one of the following manners: an optional menu displayed on the display interface; touch information of different predetermined areas on the display interface; or received preset voice information.

According to some exemplary embodiments, the step of displaying, on the display interface, the human body model in the form of the tissue layer model corresponding to the at least one first display instruction includes: updating and displaying the tissue layer model in a preset format, wherein the preset format includes one of the group including: displaying the human body model that is updated in the visual scope of the display interface; displaying the human body model that is updated in a predetermined colour; or displaying the human body model other than the tissue layer model with a predetermined transparency.

According to some exemplary embodiments, the human body information display method further includes the steps of: obtaining user's appearance information; determining the combined information of the user's appearance information and the human body model according to the human body model; and displaying the combined information on the display interface.

According to some exemplary embodiments, the human body model is a personalized three-dimensional human body model generated from actual human body parameters of the user.

According to some exemplary embodiments, the human body information display method further includes the steps of: displaying at least one human body information tag on the display interface; and obtaining a trigger instruction for one human body information tag, and prominently displaying, on the display interface, at least the local model of the personalized three-dimensional human body model and/or the human body information corresponding to the human body information tag.

According to some exemplary embodiments, the step of displaying at least one human body information tag on the display interface includes: dividing a human body image obtained by displaying the personalized three-dimensional human body model into a plurality of different areas with each serving as one of the human body information tags.

According to some exemplary embodiments, the human body information display method further includes the steps of: if a contact position on the display interface is clicked once or continuously, or the contact position is contacted continuously at a contact duration larger than a preset trigger duration, magnifying the personalized three-dimensional human body model by a predetermined multiple with at least local model or the human body information tag corresponding to the contact position as a centre; and displaying the personalized three-dimensional human body model that is magnified on the display interface.

According to some exemplary embodiments, the human body information display method further includes the steps of: displaying at least one curve surrounding the personalized three-dimensional human body model on the display interface, at least one human body information tag being provided along the curve; and obtaining a trigger instruction for one human body information tag, and prominently displaying, on the display interface, at least the local model of the personalized three-dimensional human body model or the human body information corresponding to the human body information tag.

According to some exemplary embodiments, the step of displaying at least one curve surrounding the personalized three-dimensional human body model on the display interface, at least one human body information tag being provided on the curve includes: obtaining sense information from a position sensor or obtaining touch information on the display interface, the touch information including at least one of the group including a contact position, a contact area, a contact duration or continuous contact information, the continuous contact information including start-point position contact information and end-point position contact information; determining interface action information according to the sense information or the touch information; and updating and displaying at least one of the personalized three-dimensional human body model and the curve according to the interface action information.

According to some exemplary embodiments, the sense information includes a contact position and a contact duration, and the interface action information includes: magnifying the personalized three-dimensional human body model by a predetermined multiple with at least local model or the human body information tag corresponding to a contact position as a centre if the contact position is clicked once or continuously, or the contact duration is larger than a preset trigger duration; and displaying the personalized three-dimensional human body model that is magnified on the display interface.

According to some exemplary embodiments, the human body information display method further includes the steps of: determining deflection displacement according to the sense information or the touch information, and the interface action information includes: moving all the human body information tags along the curve according to the deflection displacement; and displaying the human body information tags that are moved on the display interface.

According to some exemplary embodiments, the step of moving all the human body information tags along the curve according to the deflection displacement includes: determining a rotation angle value of the human body information tag according to a deflection distance of the deflection displacement and a distance between the contact position and a geometric central axis of the curve; and moving the human body information tag along the curve according to a deflection direction of the deflection displacement and the rotation angle value.

According to some exemplary embodiments, the human body information display method further includes the step of: determining deflection displacement according to the sense information or the touch information, and the interface action information includes: rotating the personalized three-dimensional human body model according to the deflection displacement; and displaying the personalized three-dimensional human body model that is rotated on the display interface.

According to some exemplary embodiments, the personalized three-dimensional human body model rotates on its axis at a predetermined speed on the display interface, and the interface action information includes: stopping the rotation of the personalized three-dimensional human body model; and displaying the personalized three-dimensional human body model that is stopped on the display interface.

According to some exemplary embodiments, the curve is static with respect to the display interface, and the curve includes at least one of the group including: an elliptical arc around the chest position of the personalized three-dimensional human body model; and a helical line spirally extending from the foot of the personalized three-dimensional human body model to the head of the personalized three-dimensional human body model.

According to some exemplary embodiments, the human body information tags that are adjacent on the curve are equidistantly spaced, and the information of the human body information tag includes at least one of the group including: human body organ category information, human body system category information, human body parameter information and health parameter information.

According to some exemplary embodiments, the curve includes a preset prominently-displayed area and a preset non-prominently-displayed area, and the step of displaying at least one curve surrounding the personalized three-dimensional human body model on the display interface, at least one human body information tag being provided on the curve, includes: magnifying and displaying the human body information tag and setting the human body information tag to an active state if the human body information tag is moved to the preset prominently-displayed area; and demagnifying and displaying the human body information tag and setting the human body information tag to an inactive state if the human body information tag is moved to the preset non-prominently-displayed area.

According to some exemplary embodiments, the personalized three-dimensional human body model includes a human body prominently-displayed area, and when the human body information tag is moved to the preset prominently-displayed area, the human body prominently-displayed area is moved to a part of the personalized three-dimensional human body model corresponding to the content of the human body information tag for prominent display.

According to some exemplary embodiments, if the health assessment module identifies the physical examination report of the user to obtain the health parameter information related to the human body health of the user, the human body information tag is displayed in a differential manner according to the abnormal information identified from the physical examination report.

According to another aspect of the present disclosure, there is provided a human body model generation method for generating the human body model in the above-mentioned health management system, including the steps of: obtaining an actual human body parameter of a user; and processing a typical variable human body model in a variable human body model library according to the actual human body parameter to generate a personalized variable human body model corresponding to the actual human body parameter.

According to some exemplary embodiments, the step of processing a typical variable human body model in a variable human body model library according to the actual human body parameter to generate a personalized variable human body model corresponding to the actual human body parameter includes: determining a gender of the user according to the actual human body parameter; and processing a typical human body model of the gender in the variable human body model library to generate a personalized variable human body model corresponding to the actual human body parameter.

According to some exemplary embodiments, the step of processing a typical variable human body model in a variable human body model library according to the actual human body parameter to generate a personalized variable human body model corresponding to the actual human body parameter includes: interpolating the typical variable human body model according to the actual human body parameter to generate a personalized variable human body model corresponding to the actual human body parameter.

According to some exemplary embodiments, the typical variable human body model is obtained in advance by the following manners: constructing a plurality of actual human body models according to a plurality of sample human body parameters, wherein each of the sample human body parameters includes at least one type of human body physical sign data of an actual human body; determining a principal shape change component of each of the actual human body models and a shape change characteristic value corresponding to the principal shape change component according to a principal component analysis method; and determining the typical variable human body model according to the principal shape change component and the shape change characteristic value.

According to some exemplary embodiments, the typical variable human body model is obtained in advance by the following manners: extracting a typical human body parameter from variable model original data; and generating the typical variable human body model according to the typical human body parameter.

According to some exemplary embodiments, the human body model generation method further includes the step of: converting the file of the typical variable human body model into a binary file for storage after generating the typical variable human body model according to the typical human body parameter, wherein the binary file of the typical variable human body model includes a typical human body parameter in a binary format.

According to some exemplary embodiments, the variable model original data include a plurality of sample human body parameters, and each of the sample human body parameters includes at least one type of human body physical sign data of an actual human body; and the step of extracting a typical human body parameter from variable model original data includes: determining at least one physical sign characteristic value of each type of the human body physical sign data according to the human body physical sign data in the plurality of sample human body parameters; and determining one typical human body parameter according to each of the physical sign characteristic values.

According to some exemplary embodiments, the step of determining one typical human body parameter according to each of the physical sign characteristic values includes: for each physical sign characteristic value, regarding the physical sign characteristic value as a type of human body physical sign data in the typical human body parameter; and determining other types of human body physical sign data in the typical human body parameter according to the physical sign characteristic value and a mapping relationship between different types of human body physical sign data.

According to some exemplary embodiments, the step of determining at least one physical sign characteristic value of each type of the human body physical sign data according to the human body physical sign data in the plurality of sample human body parameters includes: constructing a plurality of actual human body models according to the plurality of sample human body parameters; detecting change information of each type of the human body physical sign data in each of the actual human body models; and determining at least one physical sign characteristic value of each type of the human body physical sign data according to the change information.

According to some exemplary embodiments, the step of constructing a plurality of actual human body models according to the plurality of sample human body parameters includes: generating one actual human body model according to each of the sample human body parameters to obtain the plurality of actual human body models; and normalizing the plurality of actual human body models to make the positions and angles of the plurality of actual human body models consistent in the same three-dimensional space.

According to some exemplary embodiments, the step of normalizing the plurality of actual human body models to make the positions and angles of the plurality of actual human body models consistent in the same three-dimensional space includes: selecting any one of the actual human body models as an initial model; and moving and rotating the rest of the actual human body models in the same three-dimensional space sequentially until the position and angle of the actual human body model that is moved and rotated in the three-dimensional space are consistent with the position and angle of the initial model in the three-dimensional space.

According to some exemplary embodiments, the step of interpolating the typical variable human body model in the variable human body model library according to the actual human body parameter to generate a human body model corresponding to the actual human body parameter includes: determining a candidate variable human body model from the typical variable human body models in the variable human body model library according to the actual human body parameter; and interpolating the candidate variable human body model to generate a human body model corresponding to the actual human body parameter.

According to some exemplary embodiments, the step of determining a candidate variable human body model from the typical variable human body models in the variable human body model library according to the actual human body parameter includes: determining an actual human body parameter class of the actual human body parameter; and according to a mapping relationship between the actual human body parameter class and the typical human body parameter, determining the typical variable human body model of the typical human body parameter mapped by the actual human body parameter class as the candidate variable human body model.

According to some exemplary embodiments, the actual human body parameter class includes the data class of at least one type of human body physical sign data, and each data class has a mapping relationship with at least one typical human body parameter; and the step of according to the mapping relationship between the actual human body parameter class and the typical human body parameter, determining the typical variable human body model of the typical human body parameter mapped by the actual human body parameter class as the candidate variable human body parameter class as the candidate variable human body model includes: according to the mapping relationship between the data class of the human body physical sign data and the typical human body parameter, determining the typical variable human body model of the typical human body parameter mapped by each type of human body physical sign data in the actual human body parameter class as a candidate variable human body model of the type of the human body physical sign data.

According to some exemplary embodiments, the step of interpolating the candidate variable human body model to obtain a personalized variable human body model includes: according to the mapping relationship, determining the proportion coefficient between the actual human body parameter and the typical human body parameter that is mapped as a model weight coefficient; and according to the model weight coefficient, modifying the candidate variable human body model to obtain the personalized variable human body model.

According to some exemplary embodiments, the step of, according to the model weight coefficient, modifying the candidate variable human body model to obtain the personalized variable human body model includes: according to the model weight coefficients of the candidate variable human body models of various types of the human body physical sign data, modifying the candidate variable human body models of various types of the human body physical sign data to obtain the personalized variable human body models based on various types of the human body physical sign data.

According to some exemplary embodiments, the step of according to the model weight coefficients of the candidate variable human body models of various types of the human body physical sign data, modifying the candidate variable human body models of various types of the human body physical sign data to obtain the personalized variable human body models based on various types of the human body physical sign data includes: obtaining the personalized variable human body model based on various types of the human body physical sign data by the following manner:

$$X_0 = \sum_1^k (p_i X_i + q_i Y_i)$$

wherein $X_0$ is a personalized viable human body model, $X_i$ and $Y_i$ are respectively two candidate variable human body models of the i-th type of human body physical sign data, and $p_i$ and $q_i$ are respectively the model weight coefficients of the candidate variable human body models $X_i$ and $Y_i$.

According to some exemplary embodiments, the actual human body parameter class includes the data class of at least one type of human body physical sign data, and each data class has a mapping relationship with at least one typical human body parameter; and the step of according to the mapping relationship, determining a proportion coefficient between the actual human body parameter and the typical human body parameter that is mapped as a model weight coefficient includes: according to the mapping relationship between the data class of the human body physical sign data and the typical human body parameter, determining the proportion coefficient between each type of the human body physical sign data in the actual human body parameter and the type of the human body physical sign data in the typical human body parameter that is mapped as the model weight coefficient of the candidate variable human body model of the type of the human body physical sign data.

According to some exemplary embodiments, the step of according to the mapping relationship between the data class of the human body physical sign data and the typical human body parameter, determining the proportion coefficient between each type of the human body physical sign data in the actual human body parameter and the type of the human body physical sign data in the typical human body parameter that is mapped as the model weight coefficient of the candidate variable human body model of the type of the human body physical sign data includes: according to the mapping relationship between the data class of the human body physical sign data and the typical human body parameter, determining the proportion coefficient between each type of the human body physical sign data in the actual human body parameter and the median of the type of the human body physical sign data in the typical human body parameter that is mapped as the model weight coefficient of the candidate variable human body model of the type of the human body physical sign data.

According to some exemplary embodiments, the step of interpolating the typical variable human body model in the variable human body model library according to the actual human body parameter to obtain a personalized variable human body model corresponding to the actual human body parameter includes: according to a priority order of at least two types of human body physical sign data in the actual human body parameter, for the first type of human body physical sign data, determining the candidate variable human body model of the first type of human body physical sign data from the typical variable human body models in the variable human body model library, and interpolating the candidate variable human body model of the first type of human body physical sign data to obtain the personalized variable human body model corresponding to the first type of human body physical sign data; and for each type of human body physical sign data after the first type of human body physical sign data, according to the typical variable human body model in the variable human body model library and the personalized variable human body model corresponding to the previous type of human body physical sign data, determining the candidate variable human body model of the type of the human body physical sign data, and interpolating the candidate variable human body model of the type of the human body physical sign data to obtain the personalized variable human body model corresponding to the type of the human body physical sign data.

According to some exemplary embodiments, the step of for the first type of human body physical sign data, determining the candidate variable human body model of the first type of human body physical sign data from the typical variable human body models in the variable human body model library, and interpolating the candidate variable human body model of the first type of human body physical sign data to obtain the personalized variable human body model corresponding to the first type of human body physical sign data includes: for the first type of human body physical sign data, according to the mapping relationship between the data class of the human body physical sign data and the typical human body parameter, determining the respective typical variable human body models of the two typical human body parameters mapped by the human body physical sign data as the two candidate variable human body models of the type of the human body physical sign data; according to the mapping relationship between the human body physical sign data and the typical human body parameter, determining the proportion coefficients between the type of the human body physical sign data in the actual human body parameters and the type of the human body physical sign data of the two candidate variable human body models as the model weight coefficients of the two candidate variable human body models of the type of the human body physical sign data; and according to the model weight coefficients of the two candidate variable human body models of the type of the human body physical sign data, interpolating the two candidate variable human body models of the type of the human body physical sign data to obtain the personalized variable human body model corresponding to the type of the human body physical sign data.

According to some exemplary embodiments, the step of for each type of human body physical sign data after the first type of human body physical sign data, according to the typical variable human body model in the variable human body model library and the personalized variable human body model corresponding to the previous type of human body physical sign data, determining the candidate variable human body model of the type of the human body physical sign data, and interpolating the candidate variable human body model of the type of the human body physical sign data to obtain the personalized variable human body model corresponding to the type of the human body physical sign data includes: for each type of human body physical sign data after the first type of human body physical sign data, according to the mapping relationship between the data class of the human body physical sign data and the typical human body parameter, determining the typical variable human body model of one of the typical human body parameters mapped by the type of the human body physical sign data, and regarding the typical variable human body model corresponding to the type of the human body physical sign data and the personalized variable human body model corresponding to the previous type of the human body physical sign data as the two candidate variable human body models of the type of the human body physical sign data; according to the mapping relationship between the human body physical sign data and the typical human body parameter, determining the proportion coefficient between the type of the human body physical sign data in the actual human body parameters and the type of the human body physical sign data of the two candidate variable human body models as the model weight coefficients of the two candidate variable human body models of the type of the human body physical sign data; and according to the model weight coefficients of the two candidate variable human body models of the type of the human body physical sign data, interpolating the two candidate variable human body models of the type of the human body physical sign data to obtain the personalized variable human body model corresponding to the type of the human body physical sign data.

According to some exemplary embodiments, for each type of the human body physical sign data in the actual human body parameter, the step of according to the mapping relationship between the human body physical sign data and the typical human body parameter, determining the proportion coefficient between the type of the human body physical sign data and the type of the human body physical sign data of the candidate variable human body model as the model weight coefficient of the candidate variable human body model of the type of the human body physical sign data includes: according to the mapping relationship between the data class of the human body physical sign data and the typical human body parameter, determining the difference between the type of the human body physical sign data and that in a first typical human body parameter that is mapped as the first physical sign difference; determining the difference between the type of the human body physical sign data in the two typical human body parameters mapped by the type of the human body physical sign data as the typical physical sign difference; determining the proportion coefficient between the first physical sign difference and the typical physical sign difference as the model weight coefficient of one candidate variable human body model of a second typical human body parameter; and according to the model weight coefficient of one candidate variable human body model of the second typical human body parameter, determining the model weight coefficient of one candidate variable human body model of the first typical human body parameter.

According to some exemplary embodiments, for each type of the human body physical sign data in the actual human body parameter, the step of according to the mapping relationship between the human body physical sign data and the typical human body parameter, determining the proportion coefficient between the type of the human body physical sign data and the type of the human body physical sign data of the candidate variable human body model as the model weight coefficient of the candidate variable human body model of the type of the human body physical sign data includes: as for the k-th type of the human body physical sign data, determining the model weight coefficient of the candidate variable human body model of each type of the human body physical sign data by the following manner:

$$\begin{bmatrix} a_{11} & \cdots & a_{1k} \\ \vdots & \ddots & \vdots \\ a_{k1} & \cdots & a_{kk} \end{bmatrix} \cdot \begin{bmatrix} g_1 \\ \vdots \\ g_k \end{bmatrix} = \begin{bmatrix} f_1 \\ \vdots \\ f_k \end{bmatrix}$$

$$\begin{bmatrix} a_{11} & \cdots & a_{1k} \\ \vdots & \ddots & \vdots \\ a_{k1} & \cdots & a_{kk} \end{bmatrix}$$

is a transformation matrix, $[g_1, \ldots, g_k]$ is the model weight coefficient of the k candidate variable human body models corresponding to the k-th type of the human body physical sign data, $[f_1, \ldots, f_k]$ is the k-th type of the human body physical sign data in the actual human body parameter, wherein k is an integer larger than 0; and the transformation matrix is determined in advance according to the typical human body parameter mapped by the k-th type of the human body physical sign data.

According to some exemplary embodiments, the transformation matrix is determined by the following manner: substituting the typical human body parameter mapped by the k-th type of the human body physical sign data into the transformation matrix; or substituting the difference obtained by subtracting the human body physical sign data of the two typical human body parameters mapped by each type of the human body physical sign data into the transformation matrix.

According to some exemplary embodiments, after obtaining the candidate variable human body model, the human body model generation method further includes the steps of: determining the key frame information of the candidate variable human body model according to the binary file of the candidate variable human body model; and generating and outputting the binary file of the key frame of the candidate variable human body model according to the key frame information of the candidate variable human body model.

According to some exemplary embodiments, after generating and outputting the binary file of the key frame of the candidate variable human body model according to the key frame information of the candidate variable human body model, the human body model generation method further includes the steps of: reading out the key frame information of the candidate variable human body model from the binary file of the key frame of the candidate variable human body model; and performing a tween operation according to the key frame information of the candidate variable human body model to obtain and play the animation of the candidate variable human body model.

According to some exemplary embodiments, after processing the typical variable human body model in the variable human body model library according to the actual human body parameter to obtain the personalized variable human body model corresponding to the actual human body parameter, the human body model generation method further includes the step of: converting the file of the personalized variable human body model into a binary file and outputting the same, wherein the binary file of the personalized variable human body model includes a personalized variable human body parameter in a binary format.

According to some exemplary embodiments, the step of converting the personalized variable human body model into a binary file includes: creating a binary file; and writing a model name, a number of vertices and three-dimensional positions of the vertices in the personalized variable human body model into the binary file layer by layer.

According to some exemplary embodiments, after converting the personalized variable human body model into a binary file and before outputting the binary file of the personalized variable human body model, the human body model generation method further includes the step of: adding check bits and file size information into the binary file of the personalized variable human body model.

According to some exemplary embodiments, after converting the personalized variable human body model into a binary file and outputting the same, the human body model generation method further includes the steps of: determining the key frame information of the personalized variable human body model according to the binary file of the personalized variable human body model; and generating and outputting the binary file of the key frame of the personalized variable human body model according to the key frame information of the personalized variable human body model.

According to some exemplary embodiments, the human body model generation method further includes the step of: storing the binary file by means of a Unity script.

According to some exemplary embodiments, the human body model generation method further includes the steps of: reading out the key frame information of the personalized variable human body model from the binary file of the key frame of the personalized variable human body model; and performing a tween operation according to the key frame information of the personalized variable human body model to obtain and play the animation of the personalized variable human body model.

According to some exemplary embodiments, the personalized variable human body model corresponding to the actual human body parameter includes: the personalized variable human body model corresponding to each type of the human body physical sign data in the actual human body parameter; and the step of reading out the key frame information of the personalized variable human body model from the binary file of the key frame of the personalized variable human body model includes: reading out the key frame information of the personalized variable human body model corresponding to the type of the human body physical sign data from the binary file of the key frame of the personalized variable human body model corresponding to each type of the human body physical sign data; and the step of performing a tween operation according to the key frame information of the personalized variable human body model to obtain and play the animation of the personalized variable human body model includes: performing a tween operation according to the key frame information of the personalized variable human body model corresponding to each type of the human body physical sign data to obtain the animation of the personalized variable human body model corresponding to the type of the human body physical sign data; and sequentially playing the animation of the personalized variable human body models corresponding to various types of the human body physical sign data according to the priority order of various types of the human body physical sign data.

According to another aspect of the present application, there is provided a computer device including a memory and a processor, wherein the memory stores a computer program, that, when executed by the processor, realizes the human body information display method as stated above or the human body model generation method as stated above.

According to another aspect of the present application, there is provided a computer-readable storage medium which stores a computer program, that, when executed by the processor, realizes the human body information display method as stated above or the human body model generation method as stated above.

BRIEF DESCRIPTION OF DRAWINGS

The above-mentioned and/or additional aspects and advantages of the present disclosure will be described in detail in view of exemplary embodiments and in conjunction with the drawings, wherein:

FIG. 1 schematically shows a health management system according to an exemplary embodiment of the present disclosure in the form of a block diagram;

FIG. 2 schematically shows a health management system according to another exemplary embodiment of the present disclosure in the form of a block diagram;

Figures 12, 13:
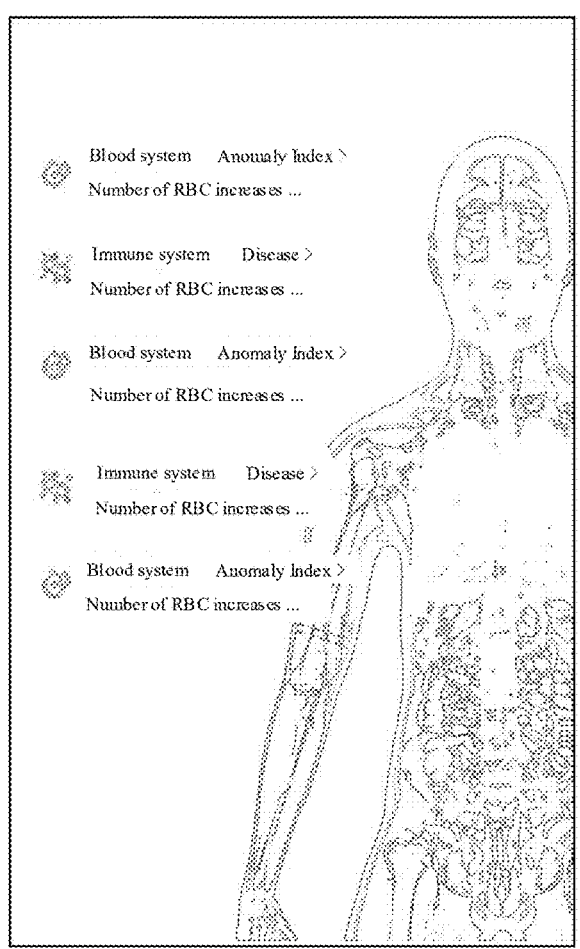
Figures 14A, 14B, 14C:
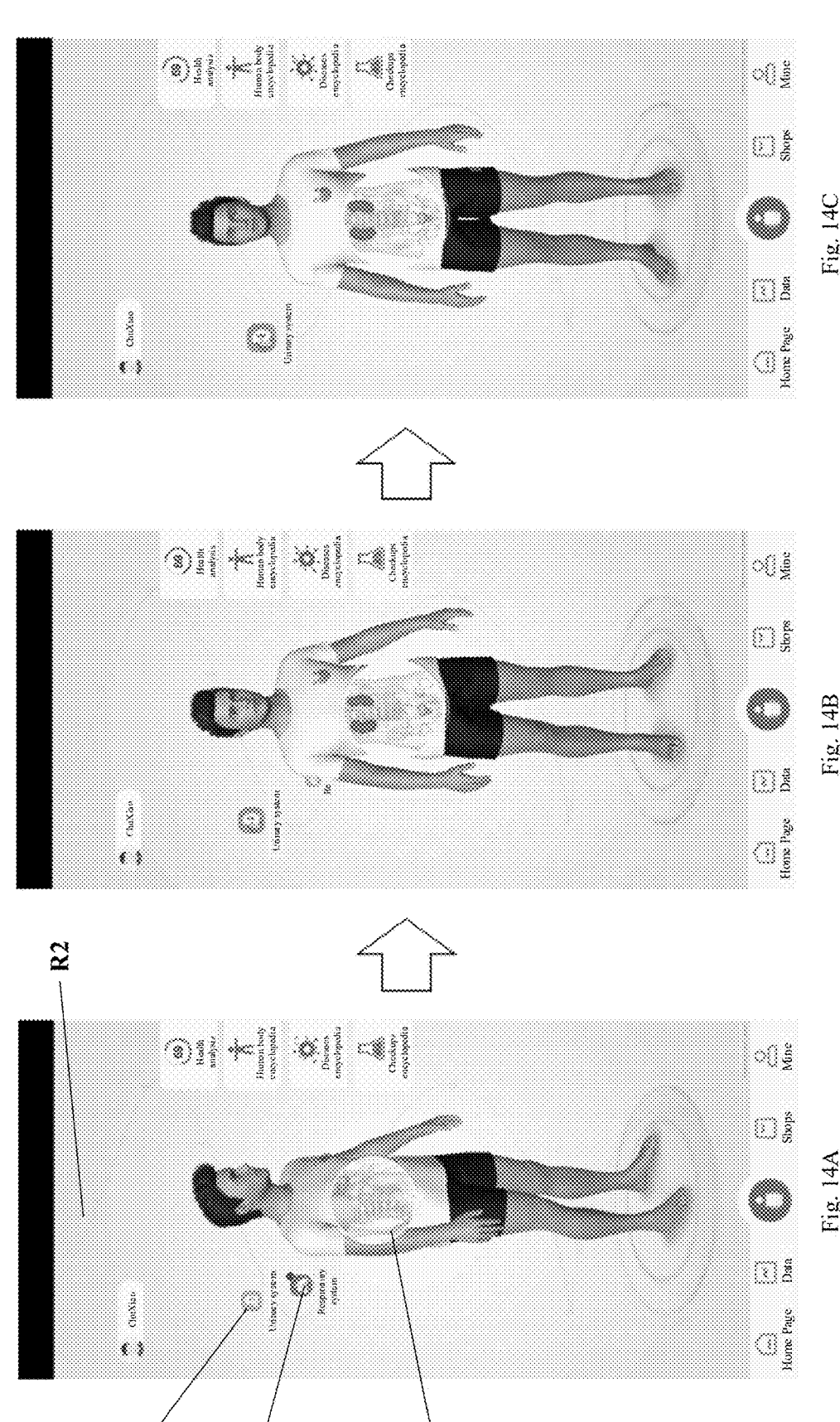
Figure 17:
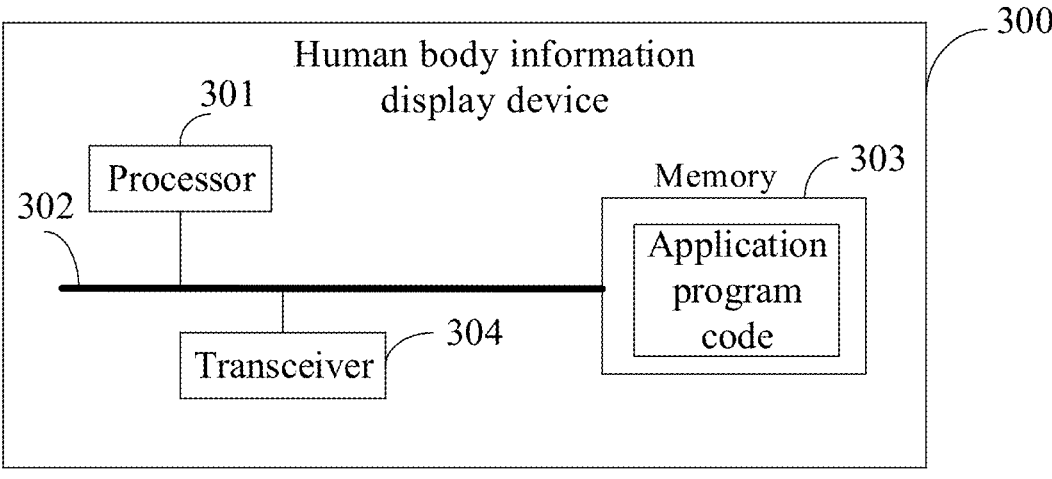
Figure 18:
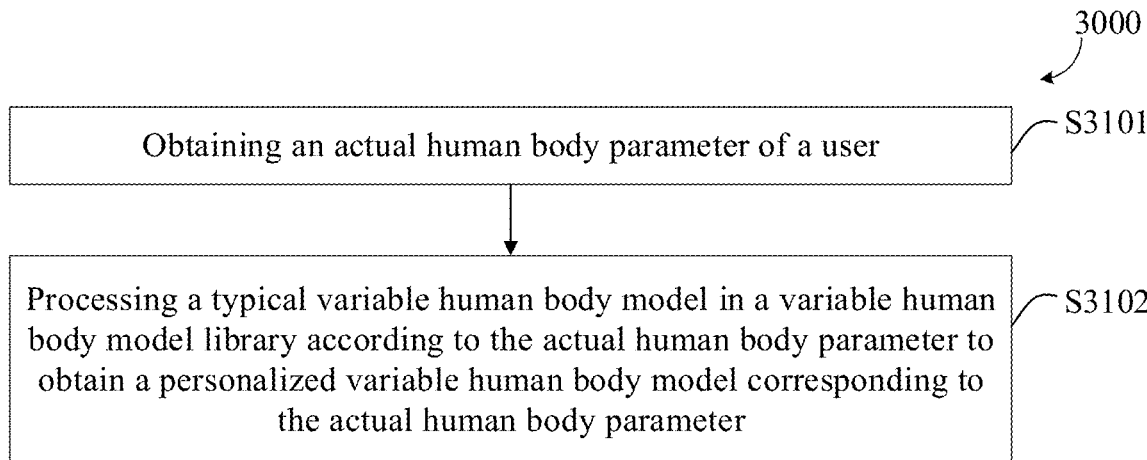
Figure 21A:
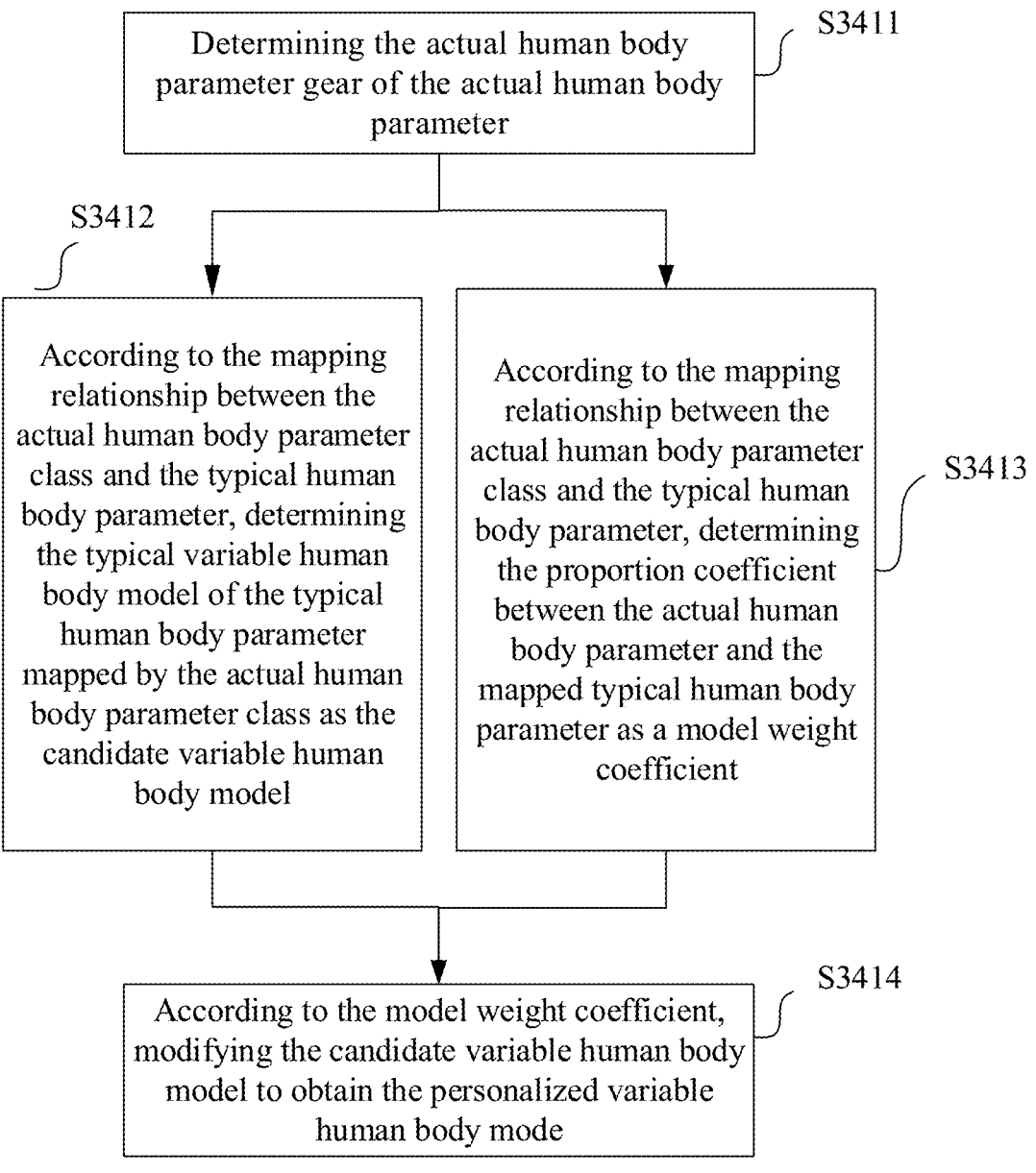
Figure 22:
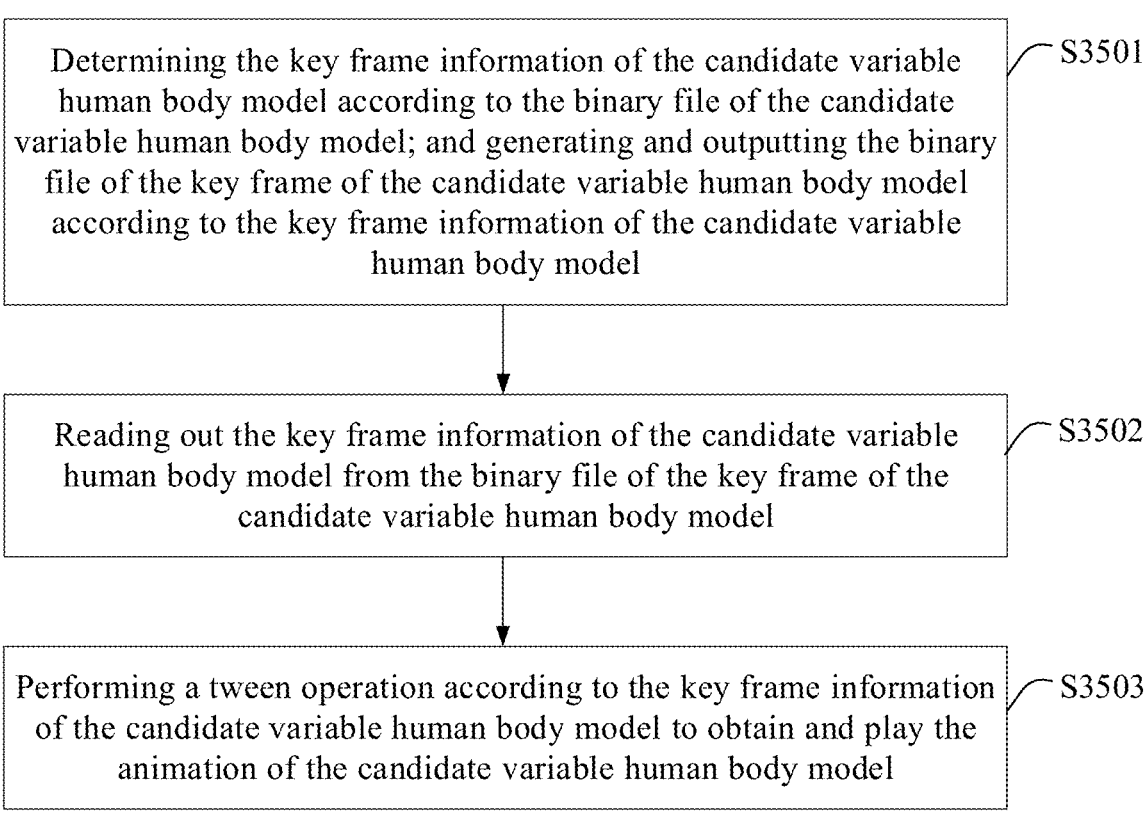
Figure 23A:
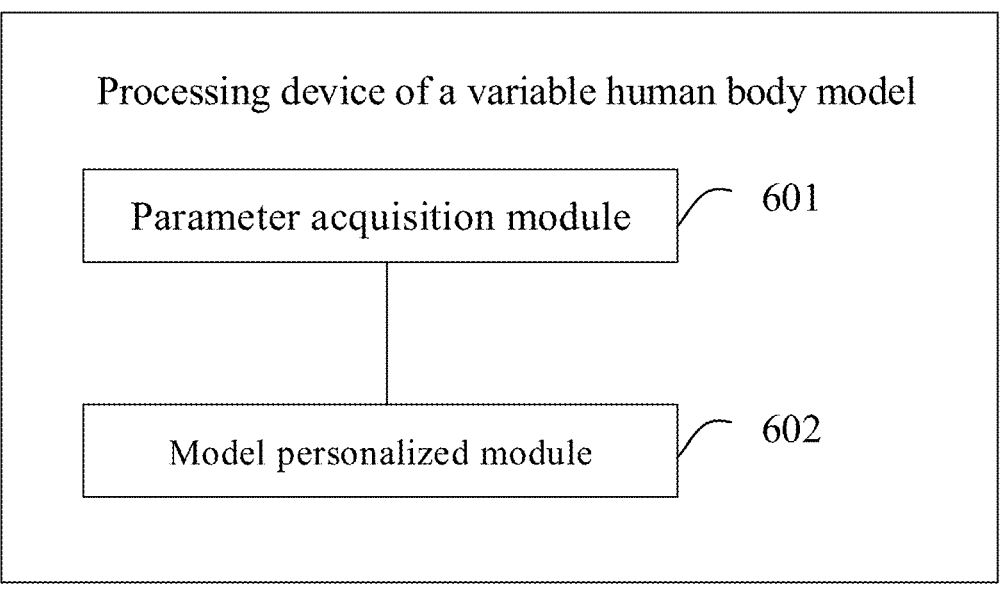
Figure 23B:
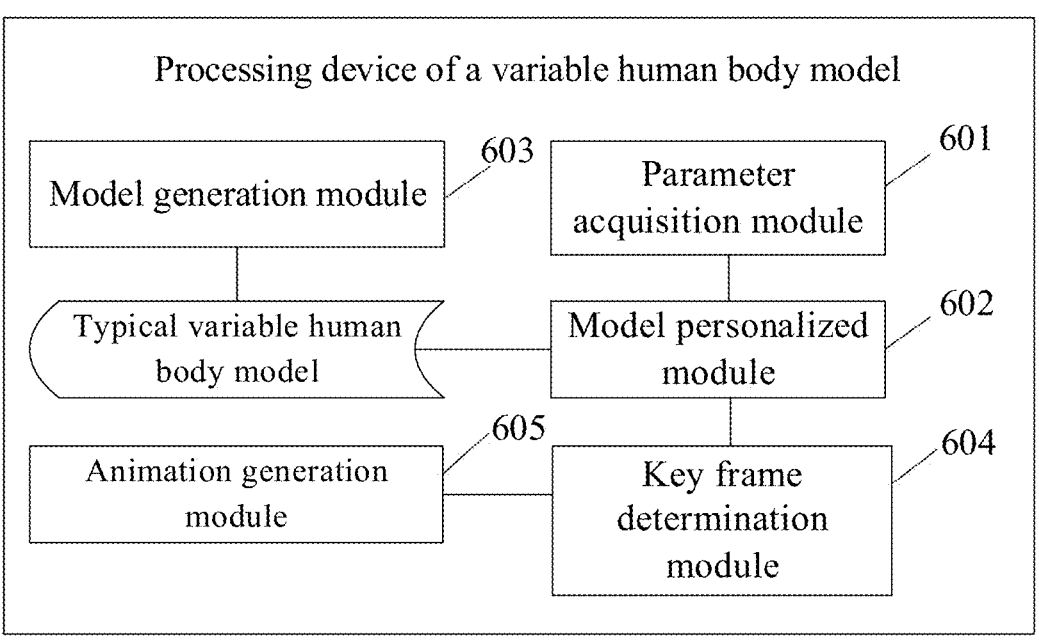
Figure 24:
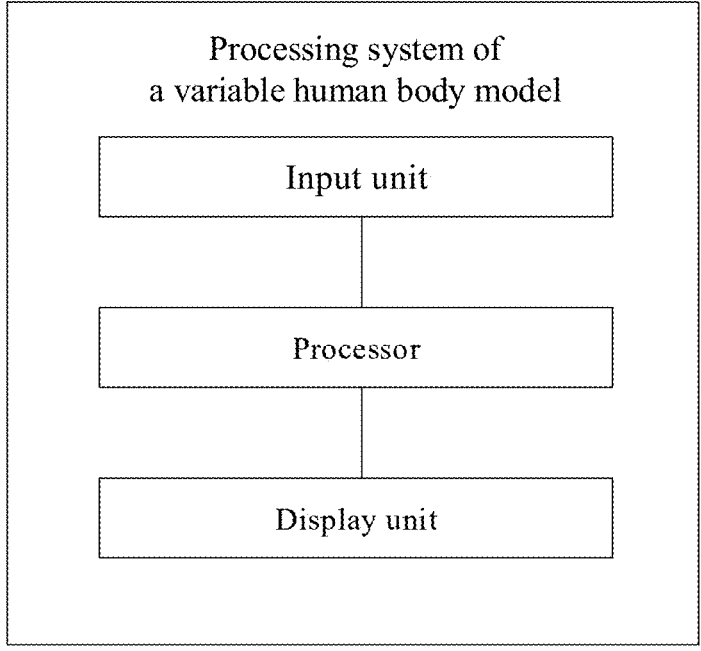
Figure 25:
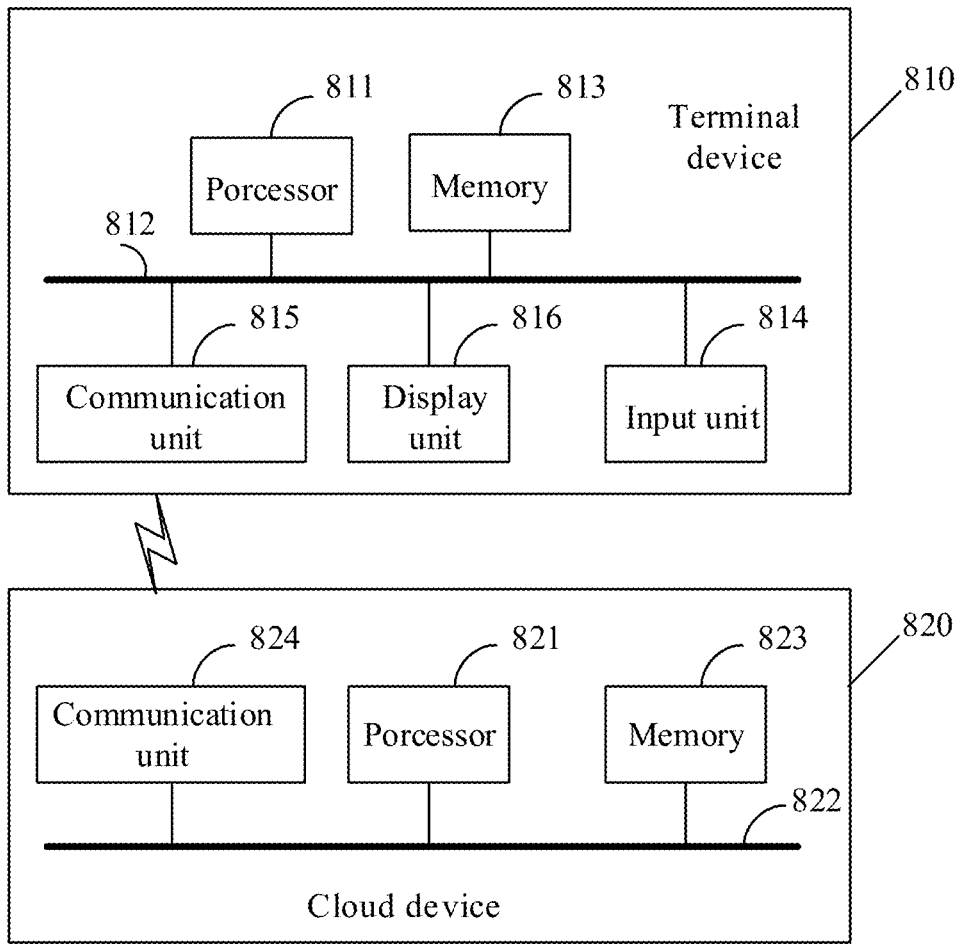

Each of FIGS. 8B, 8C, 8D and 8E schematically shows a display interface showing a three-dimensional human body model and human body information tags according to an exemplary embodiment;

FIG. 9 schematically shows a human body information display method according to another exemplary embodiment of the present disclosure in the form of a flowchart;

FIG. 10A is a schematic view of a display interface presenting human body information according to another exemplary embodiment of the present disclosure;

FIG. 10B is a schematic view of a display interface presenting human body information according to another exemplary embodiment of the present disclosure;

FIG. 11 schematically shows a method for updating and displaying a three-dimensional human body model and a curve according to an exemplary embodiment of the present disclosure in the form of a flowchart;

FIG. 12 is a schematic view of a display interface presenting human body information according to another exemplary embodiment of the present disclosure;

FIG. 13 is a schematic view of a display interface presenting human body information according to another exemplary embodiment of the present disclosure;

Each of FIGS. 14A, 14B and 14C schematically shows a display interface showing a three-dimensional human body model and human body information tags according to an exemplary embodiment;

Each of FIGS. 15A and 15B schematically shows a display interface showing a three-dimensional human body model and a human body information tag according to an exemplary embodiment;

FIG. 16 schematically shows the structure of a human body information display device according to another exemplary embodiment of the present disclosure in the form of a block diagram;

FIG. 17 shows the structure of a computing device used for a human body information display method according to an exemplary embodiment of the present disclosure in the form of a block diagram;

FIG. 18 schematically shows a human body model generation method according to an exemplary embodiment of the present disclosure in the form of a flowchart;

FIG. 19A is a schematic flowchart of a method for obtaining a typical variable human body model according to an exemplary embodiment of the present disclosure;

FIG. 19B is a schematic flowchart of another method for obtaining a typical variable human body model according to an exemplary embodiment of the present disclosure;

FIG. 20A is a schematic flowchart of a method for deploying and processing a variable human body model based on a typical variable human body model according to an exemplary embodiment of the present disclosure;

FIG. 20B is a schematic flowchart of another method for deploying and processing a variable human body model based on a typical variable human body model according to an exemplary embodiment of the present disclosure;

FIG. 20C is a schematic flowchart of a further method for deploying and processing a variable human body model based on a typical variable human body model according to an exemplary embodiment of the present disclosure;

FIG. 21A is a schematic flowchart of a processing method for interpolating a typical variable human body model according to an exemplary embodiment of the present disclosure;

FIG. 21B is a schematic flowchart of another processing method for interpolating a typical variable human body model according to an exemplary embodiment of the present disclosure;

FIG. 22 is a partial schematic flowchart of another method for deploying and processing a variable human body model according to an exemplary embodiment of the present disclosure;

FIG. 23A schematically shows the structure of a processing device of a variable human body model according to an exemplary embodiment of the present disclosure in the form of a block diagram;

FIG. 23B schematically shows the structure of another processing device of a variable human body model according to an exemplary embodiment of the present disclosure in the form of a block diagram;

FIG. 24 is an architecture schematic view of a processing system of a variable human body model according to an exemplary embodiment of the present disclosure;

FIG. 25 is a deployed architecture schematic view of a processing system of a variable human body model according to an exemplary embodiment of the present disclosure.

It should be understood that the drawings are only used for schematically showing various exemplary embodiments of the present disclosure and therefore do not need to be drawn to scale.

DETAILED DESCRIPTION

The present disclosure will be described in detail, and various exemplary embodiments of the present disclosure are shown in the drawings. Throughout all the drawings, identical or similar reference numerals indicate identical or similar features. In addition, the detailed description of known technologies can be omitted if it is not necessary for the features described in the present disclosure. The following embodiments described with reference to the drawings are exemplary and are only used for the purpose of explaining the present disclosure, rather than interpreted as limitations to the present disclosure.

Those skilled in the art should understand that unless otherwise defined, all terms (including technical terms and scientific terms) used herein have the same meaning as commonly understood by one having ordinary skills in the art, to which the present invention belongs. It should be further understood that terms such as those defined in a common dictionary should be construed as having the same meaning as in the context of the related art, and will not be construed in an ideal or overly formal sense, unless defined explicitly as such herein.

Those skilled in the art should understand that the singular forms of "a", an "the" and "said" are also intended to include the plural forms, unless otherwise specified clearly. It should be further understood that the terms such as "comprise" and/or "include" used in the specification of the present disclosure indicate the presence of the features, integers, steps, operations, elements and/or components, but do not exclude the presence or addition of one or more other features, integers, steps, operations, elements, components and/or groups thereof. It should be understood that when an element is referred to as being "connected to" or "coupled to" another element, it can be directly connected or coupled to another element, or intervening elements may be present. Furthermore, the term "connection" or "coupling" used herein may include wireless connection or wireless coupling. The term "and/or" used herein comprises any and all combinations of one or more related items as listed.

In the description of the specification of the present disclosure, expressions such as "an embodiment", "some embodiments", "exemplary embodiment(s)", "specific example(s)" or "some examples" are intended to mean that specific features, structures, materials or characteristics described with reference to the embodiments or examples are contained in at least one embodiment or example of this disclosure. In the specification of the present disclosure, schematic descriptions with respect to the above expressions herein do not have to be directed at the same embodiments or examples. Instead, specific features, structures, materials or characteristics described thereby can be combined in a suitable manner in any one or more embodiments or examples. Besides, where no contradiction is caused, one skilled in the art can combine and assemble different embodiments or examples described in the specification, and can combine and assemble the features of different embodiments or examples.

Various techniques may be described herein in the general context of software, hardware elements, or program modules. Generally, such modules include routines, programs, objects, elements, components, data structures, and so forth that perform particular tasks or implement particular abstract data types. The terms "module", "functionality" and "component" used herein generally represent software, firmware, hardware, or a combination thereof. The features of the techniques described herein are platform-independent, meaning that the techniques may be implemented on a variety of computing platforms having a variety of processors.

The steps included in the method described in the present disclosure are all exemplary. They do not necessarily have to be performed in the order as listed, but one or more of these steps can be performed in a different order or at the same time according to the actual situation. In addition, according to the actual situation, the described method may also include other additional steps.

FIG. 1 schematically shows a health management system 10a according to an exemplary embodiment of the present disclosure in the form of a block diagram, comprising a health assessment module 11, a health intervention module 12, a human body model generation module 13 and a human body information display module 14. It should be understood that the health management system 10a described herein and various modules included therein may be realized by any suitable type of a computing device.

As a non-limiting example, such a computing device may comprise one or more processors and one or more memories. By executing computer instructions stored in the memory by the processor, the health management system of the present disclosure and various modules included therein can be realized. For example, such computing devices include but are not limited to: desktop computers, smart TVs, set-top boxes, mobile computers (for example, Microsoft® Surface® devices, personal digital assistants (PDAs), laptops, notebook computers, tablets such as Apple iPad™, netbooks, etc.), mobile phones (such as cellular phones, smart phones like Microsoft Windows® phones, Apple iPhones and phones realizing Google® Android™ operating system, Palm® devices, Blackberry® devices and the like), wearable computing devices (such as smart watches, head-mounted devices, including smart glasses, such as Google® Glass™).

It should be understood that various modules included in the health management system of the present disclosure can also be realized by different computing devices. For example, one or more modules in the health management system of the present disclosure can be realized through a server or server cluster or cloud server. The server can be an independent physical server, or a server cluster or distributed system composed of a plurality of physical servers, or a cloud server providing cloud service, cloud database, cloud computing, cloud functions, cloud storage, network service, cloud communication, middleware service, domain name service, security service, CDN and basic cloud computing services such as big data and artificial intelligence platform, but the present disclosure is not limited thereto.

In the embodiment in which one or more modules in the health management system of the present disclosure are realized by different computing devices, different computing devices may be directly or indirectly connected by means of wired or wireless communication. For example, each of these computing devices may comprise at least one communication interface capable of communicating over a network. Such a communication interface may be one or more of the following: any type of network interface (e.g., network interface card (NIC)), wired or wireless (e.g., IEEE 802.11 wireless LAN (WLAN)) interface, worldwide microwave access interoperability (Wi-MAX) interface, Ethernet interface, universal serial bus (USB) interface, cellular network interface, Bluetooth™ interface, near-field communication (NFC) interface, etc., but the present disclosure is not limited to thereto. Further, as a non-limiting example, a network for communication interconnection may comprise any combination of a local area network (LAN), a wide area network (WAN), a personal area network (PAN), and/or a communication network such as the Internet.

With further reference to FIG. 1, the health assessment module 11 may be configured to obtain health parameter information related to human body health of a user, and generate the health status assessment result of the user based on the health parameter information. The health assessment module 11 can obtain the user's health parameter information related to human body health by receiving the information manually inputted by the user. As a non-limiting example, the health assessment module 11 may also obtain the user's health parameter information related to human body health by identifying the physical examination report or similar report provided by the user. For example, the health assessment module 11 can identify the PDF file or picture of the user's physical examination report by OCR, or scan and identify the paper file of the user's physical examination report, so as to obtain the user's health parameter information related to human body health. Then, the health assessment module 11 can make assessment according to the obtained health parameter information, for example, calculate the corresponding score according to the deviation between the actual value and the reference value of the parameter, so as to generate a health status assessment result. The health status assessment result can be displayed to the user through the display interface of the health management system 10a, for example, in the form of score. In some non-limiting examples, the health assessment module 11 may also monitor physiological indexes reflecting the user's health status. For example, for users suffering from chronic diseases such as hypertension, hyperglycemia and/or hyperlipidemia, the physiological indexes such as blood pressure, blood glucose and/or blood lipid can be monitored, and for users suffering from poor sleep quality, the indexes such as sleep quality parameter can be monitored, which is not limited by the present disclosure. In these examples, the health assessment module 11 can rely on an external physiological index acquisition device (such as sphygmomanometer, sleep meter and the like) in the process of obtaining health parameter information to achieve the above monitoring. In other non-limiting examples, the health assessment module 11 can also push a message to the user, for example, a message reminding the user of dos and dont's related to health, which is not limited in the present disclosure.

In addition, for the acquisition of external information, in addition to the physical examination report and parameter monitoring identification, the health assessment module 11 can also conduct information research in the form of questionnaire.

The health intervention module 12 may be configured to generate a health management scheme of the user based on the health status assessment result generated by the health assessment module 11. As a non-limiting example, the health intervention module 12 may generate a corresponding health management scheme based on the health status assessment result and provide it to the user. As a non-limiting example, the health intervention module 12 may monitor indexes of blood pressure, blood glucose and/or blood lipid for users suffering from chronic diseases such as hypertension, hyperglycemia and/or hyperlipidemia, or for users suffering from poor sleep quality, the health intervention module 12 may also monitor indexes such as sleep quality parameter, which is not limited in the present disclosure. In other non-limiting examples, the health intervention module 12 can also push a message to the user, for example, a message reminding the user of measuring relevant indexes, and a message reminding the user of dos and dont's related to health, which is not limited in the present disclosure.

The human body model generation module 13 may be configured to generate a human body model displayable on a display interface of the health management system 10a. The human body model generation module 13 may obtain the human body model through big data calculation based on a large number of real sample human body data. The diversity and authenticity of samples can ensure that the obtained human body model is highly precise, and also can reflect the personality characteristics of each person in terms of the human body. In addition, compared with the conventional statistical calculation method, the human body model generation module of the present disclosure can greatly reduce the amount of calculation, decrease costs, and shorten the processing time.

The human body information display module 14 may be configured to display the human body model on the display interface of the health management system 10a based on human body tissue layers, human body systems or human body parts according to received display instructions. In some exemplary embodiments, the human body information display module 14 may also display bones, organs, skin and the like in the human body model in different layers. It can be seen that the human body information display module 14 may display the human body model in the form of layers, so that when the complex human body model is displayed, the mutual occlusion of various organs or tissues is avoided, which is beneficial for the user to better understand the entire human body and the composition of various parts.

The present disclosure will describe in detail the human body model generation method used by the human body model generation module 13 and the human body information display method used by the human body information display module 14, which will not be reiterated herein. The health management system of the present disclosure at least provides the following advantageous technical effects: 1) it provides linkage with the physical examination report; 2) it provides a more convenient way to check an abnormal position/a patient's condition; 3) the server can request for the types, symptoms, treatment methods of existing diseases corresponding to a specific position/system/tissue, and provide more efficient and accurate guidance and suggestions for patients or doctors based on big data, including but not limited to diets/exercises/prescriptions.

FIG. 2 schematically shows a health management system 10b according to another exemplary embodiment of the present disclosure in the form of a block diagram. Compared with the health management system 10a shown in FIG. 1, the health management system 10b in FIG. 2 comprises a health record module 15 and an intelligent diagnosis module 16 in addition to the modules shown in FIG. 1. The health record module 15 may be configured to save the health parameter information and the health status assessment result of the user to generate the health history data of the user. The intelligent diagnosis module 16 may be configured to generate medical advice information of the user according to the consultation information received from the user and the pre-stored knowledge map. For example, the intelligent diagnosis module 16 may obtain keywords such as "fever", "38° C." and "medication" from the user's consultation information, and determine the corresponding medical advice information by searching the knowledge map. In some non-limiting examples, the intelligent diagnosis module 16 may also use natural language processing technology to process the original consultation information from the user and obtain the desired consultation information. Based on the natural language processing technology, the intelligent diagnosis module 16 may obtain the user's consultation details more efficiently.

Figure 3:
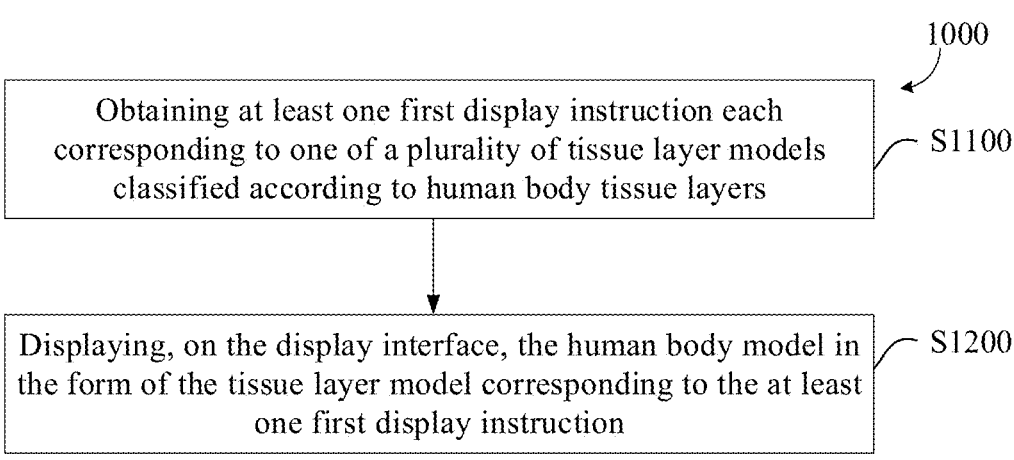
FIG. 3 schematically shows a human body information display method according to an exemplary embodiment of the present disclosure in the form of a flowchart.

FIG. 3 schematically shows a human body information display method 1000 according to an exemplary embodiment of the present disclosure in the form of a flowchart. The human body information display method 1000 may be applied to the human body information display module 14 in the health management systems 10*a* and 10*b* shown in FIG. 1 and FIG. 2. As shown in FIG. 3, the method comprises:

S1100: obtaining at least one first display instruction each corresponding to one of a plurality of tissue layer models classified according to human body tissue layers;

S1200: displaying, on the display interface, the human body model in the form of the tissue layer model corresponding to the at least one first display instruction.

The human body information display method 1000 according to the exemplary embodiment of the present disclosure may display, on the display interface, the human body model in the form of the tissue layer model classified according to the human body tissue layers by obtaining a display instruction corresponding to one of the plurality of tissue layer models classified according to the human body tissue layers, so that the user may view different tissue layers of the human body by inputting different display instructions, thereby avoiding the problem of mutual penetration or occlusion of organs or tissues, and facilitating users' better observation and understanding of human body information.

It should be noted that in the present disclosure, the term "three-dimensional human body model" refers to the display result of the human body model in three dimensions. In the present disclosure, the three dimensions are not necessarily all three directional dimensions of space. Therefore, in some exemplary embodiments of the present disclosure, when three dimensions are three directions of space, the display result of the human body model is a three-dimensional perspective view, which is considered to fall within the scope of the term "three-dimensional human body model" in the present disclosure. In other exemplary embodiments of the present disclosure, the display result of the human body model may be the rest human body tissues or systems displayed in a layered form (for example, an tissue layer model classified according to the human body tissue layers or a human body system model classified by the human body systems) in a human body contour shown in a planar view (namely, two space dimensions), and the layering method forms a third dimension for displaying the human body model, so this situation is also considered to fall within the scope of the term "three-dimensional human body model" in the present disclosure.

The content of Step S1100 is further described as: after opening the software or application that implements the health management system 10*a* and 10*b*, it will display the three-dimensional human body model in the initial state on the display interface. The three-dimensional human body model in the initial state may be preset to a specific form, which is usually an upright and naturally stretched naked human body and not displayed after classification according to some classification methods. For example, a method for classifying a three-dimensional human body model is to classify it according to the human body tissue layers, which may be a layered mode specifically comprising skin, muscles, nerves, lymph, blood vessels, etc. layer by layer from the outside to the inside. And a single layer may even be further divided, for example, the surface of the human body is covered with skin, but the skin is not just one layer but divided into epidermis and dermis according to the characteristics of different tissues. Through the first display instruction, the specific human body tissue layer corresponding to the first display instruction can be displayed on the display interface.

Figure 4:
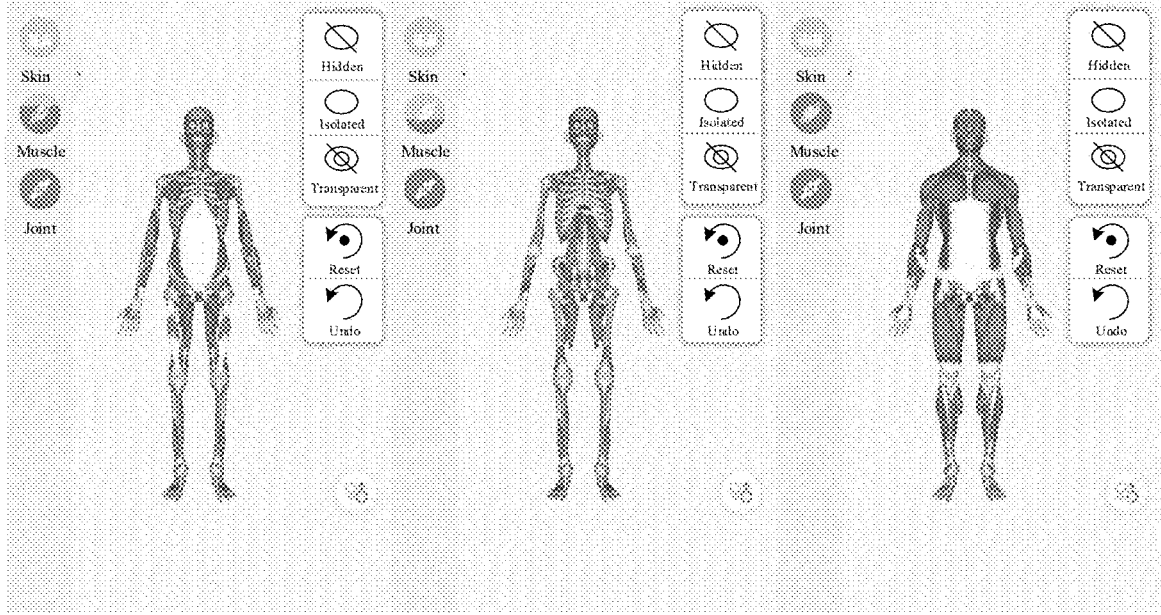
FIG. 4 is a schematic view of a display interface for displaying a three-dimensional human body model according to the classification of human body tissue layers according to an exemplary embodiment of the present disclosure.

As shown in FIG. 4, in one possible exemplary embodiment, the three-dimensional human body model is classified into three types of tissue layer models according to the human body tissue layers, and is divided into a surface tissue layer, a middle tissue layer and a deep tissue layer according to their position relationship in the human body from the outside to the inside. It should be explained that the above layering method is not carried out according to physical size. Each tissue layer has similar physiological properties. Different tissue layers have different physiological properties, but may belong to the same physiological system or physiological part. The detailed content is known to those skilled in the related art, such as those in the physiological or medical field, and will not be reiterated.

The first display instruction corresponds to the tissue layer model in a one-to-one relationship, so that the human body information display method may display, on the display interface, the three-dimensional human body model in the form of the tissue layer model corresponding to the first display instruction according to the first display instruction. When a first display instruction is obtained, the human body information display method finds the relevant data of the corresponding tissue layer model in the database according to the first display instruction, and then displays, on the display interface, the relevant data of the tissue layer model corresponding to the first display instruction in the form of image or video. Optionally, in a non-limiting embodiment, the first display instruction is obtained from at least one of the following ways:

an optional menu displayed on the display interface; or touch information of different predetermined areas on the display interface; or received preset voice information.

That is to say, the first display instruction may be inputted through the optional menu preset on the display interface. When the user clicks the optional menu through the touch screen or mouse, the first display instruction is formed. Different optional menus correspond to different first display instructions. The display interface may also be divided into different areas, and different touch screen information may be obtained by touching at different positions, so as to determine the first display instruction corresponding to the touch information. Alternatively, different first display instructions may be determined according to the times of touch in the same area. For example, one click is directed to one first display instruction, double click is directed to another first display instruction, and so on. In addition, instructions may be inputted directly into the device by means of voice input, and the first display instruction may be determined by speech recognition technology.

According to the description of three-dimensional human body models on the display interface as stated above, the three-dimensional human body models can not only be classified according to the human body tissue layers (that is, the three-dimensional human body models not only comprise a plurality of tissue layer models), but also be classified and displayed in other ways. In a non-limiting embodiment, the three-dimensional human body models also comprise a plurality of human body system models classified according to human body systems and a plurality of local human body models classified according to human body parts. Therefore, the human body information display method according to the present disclosure may also comprise the steps of: obtaining at least one second display instruction each corresponding to one of a plurality of human body system models classified according to the human body systems; and displaying, on the display interface, the human body model in the form of the human body system model corresponding to the at least one second display instruction. Alternatively, the human body information display method according to the present disclosure may also comprise the steps of: obtaining at least one third display instruction each corresponding to one of a plurality of local human body models classified according to the human body parts; and displaying, on the display interface, the human body model in the form of the local human body model corresponding to the at least one third display instruction.

The display of the human body model based on the human body tissue layers, human body systems and human body parts as described above may be implemented independently or jointly. The display interface of the device may initially show a complete three-dimensional human body model. After obtaining the first display instruction, the three-dimensional human body model may be displayed according to the human body tissue layer model. Alternatively, after obtaining the second display instruction, the three-dimensional human body model may be displayed on the display interface according to the human body system model, and the display interface still displays the three-dimensional human body model but specifically in the form of the human body system model. Alternatively, the complete three-dimensional human body model is initially shown on the display interface, after obtaining the third display instruction, the three-dimensional human body model may be displayed on the display interface according to the local human body model. The first, second and third display instructions are not necessarily conducted in order. Of course, the combination of the three display instructions may be conducted. For example, after obtaining the third display instruction first, the three-dimensional human body model is displayed in the form of the local human body model, and then the second display instruction is obtained on the display interface showing the three-dimensional human body model in the form of a local human body model, and the human body system model is superimposed on the local human body model. For example, when a heart model is displayed on the display interface, the second display instruction showing a circulatory system is obtained, and the heart model with a vascular structure is displayed on the display interface, that is, the local human body model is combined with the human body system model.

Specifically, the human body system model medically comprises a motor system model, a digestive system model, a respiratory system model, a urinary system model, a reproductive system model, an endocrine system model, an immune system model, a nervous system model and a circulatory system model. Therefore, there may be, e.g., nine second display instructions, which correspond to the human body system models in a one-to-one relationship. Similar to the acquisition and implementation manner of the first display instruction, the second display instruction is obtained. The step of displaying, on the display interface, the three-dimensional human body model in the form of the human body system model according to the second display instruction comprises: detecting at least one selected second display instruction on the display interface; and updating and displaying, on the display interface, the three-dimensional human body model as the human body system model corresponding to the second display instruction. The second display instruction may also be obtained in a form similar to the first display instruction, but the specific content of the second display instruction is different from that of the first display instruction to avoid instruction confusion.

Figure 5:
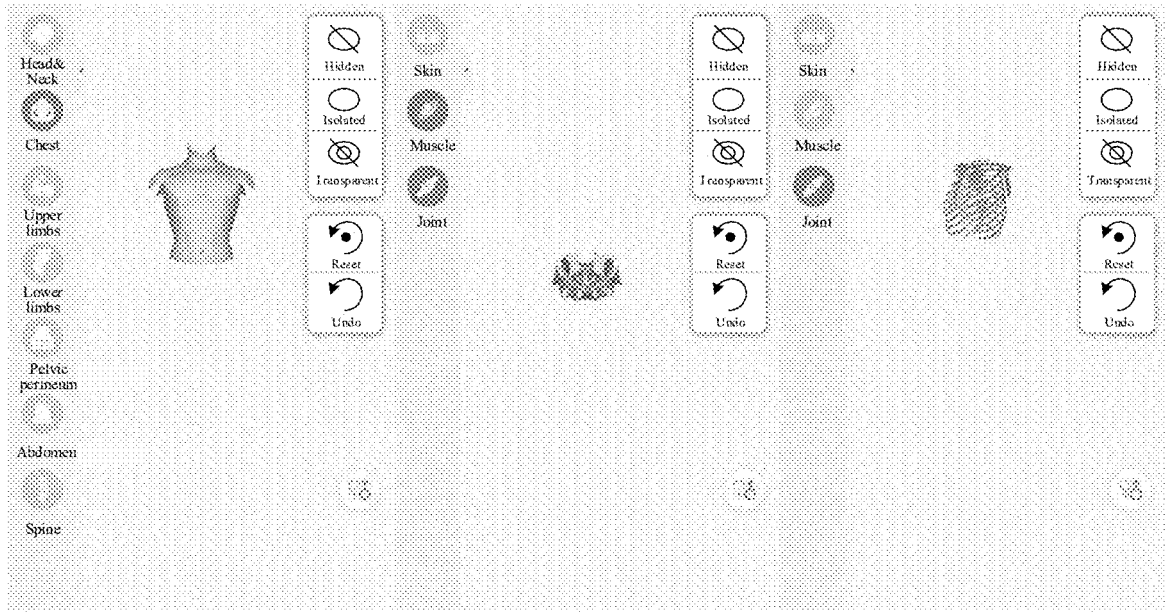
FIG. 5 is a schematic view of a display interface for displaying a three-dimensional human body model according to a local human body model according to another exemplary embodiment of the present disclosure.

Correspondingly, in the medical field, the local human body model comprises: a head and neck model, a chest model, an upper limb model, a lower limb model, a pelvic model, an abdominal model and a spine model. Therefore, there may be, e.g., seven third display instructions, which correspond to the local human body models in a one-to-one relationship. Similar to the acquisition and implementation manner of the first display instruction, the third display instruction is obtained. The step of displaying, on the display interface, the three-dimensional human body model in the form of the local human body model according to the third display instruction comprises: detecting at least one selected third display instruction on the display interface; and updating and displaying, on the display interface, the three-dimensional human body model as the local human body model corresponding to the third display instruction. As shown in FIG. 5, it illustrates a local human body model in one exemplary embodiment of the present disclosure, and the local human body model is also specifically displayed in the form of different tissue layer models.

According to the above-mentioned technical solution, for Step S1200, the three-dimensional human body model displayed on the display interface may be a three-dimensional human body model with complete human body information, or a certain human body system model, a certain local human body model, or the combination thereof (namely, a local human body system model) obtained after the updating of the complete human body information by the pre-inputted display instruction. No matter which form the above three-dimensional human body model on the display interface is, after obtaining the first display instruction, based on the first display instruction, the three-dimensional human body model is classified according to the human body tissue layers and displayed as a tissue layer model.

For the three-dimensional human body models as described above, in the database, all forms of three-dimensional human body models have their own names and corresponding relationships with instructions. The three-dimensional human body models may be classified in different forms and tabulated. For example, a human body system table is established according to the human body systems, a local human body table is established according to local human body parts, and an organ table is established according to organs, and so on. The information in the tables may be combined with each other, and the display instructions may also be superimposed correspondingly. The human body information display method of the present disclosure may be implemented circularly. For example, when the surface tissue model of the motor system, specifically the surface muscle human body model, has been displayed on the display interface, if a first display instruction is further obtained, the display instruction corresponds to the display of the middle muscle layer, which is equivalent to that on the basis of the original surface muscle human body model, the surface muscle human body information is removed to show the deeper middle muscle layer, and the middle muscle layer is displayed on the display interface as a new three-dimensional human body model.

In addition, for the step of displaying, on the display interface, the human body model in the form of the tissue layer model corresponding to the at least one first display instruction, in a non-limiting embodiment, the human body information display method updates and displays the tissue layer model in a preset format on the display interface, and the preset format may be one of the following categories:

displaying the updated three-dimensional human body model in the visual scope of the display interface; or displaying the updated three-dimensional human body model in a predetermined colour; or displaying the three-dimensional human body model other than the tissue layer model with predetermined transparency.

That is to say, the updated three-dimensional human body model may be displayed on the display interface in full screen. For example, when the dermis tissue of the head is displayed, the head dermis tissue model is displayed on the display interface in full screen to reflect the human body information more clearly. Or it is displayed in a specific colour to separate it from other parts of the three-dimensional human body model. Or the three-dimensional human body model may be displayed with different transparency to display the part of the tissue layer model required for display opaquely, and other parts with relatively high transparency, in such a way to keep the connection between the prominently displayed part(s) and the non-prominently-displayed parts.

Figure 6:
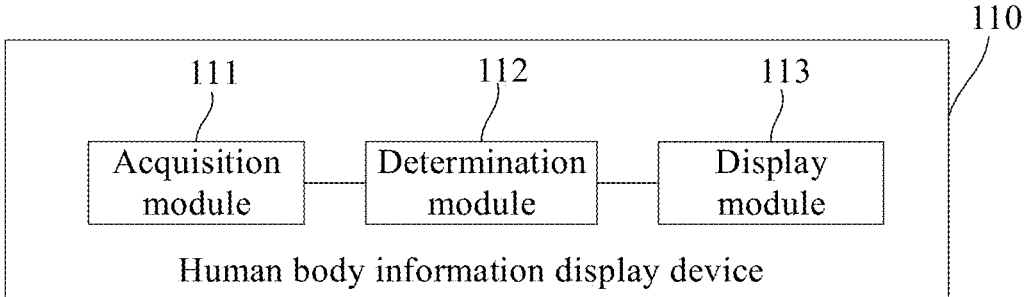
FIG. 6 schematically shows the structure of a human body information display device according to an exemplary embodiment of the present disclosure in the form of a block diagram.

FIG. 6 schematically shows the structure of a human body information display device 110 according to an exemplary embodiment of the present disclosure in the form of a block diagram. As shown in FIG. 6, the human body information display device 110 comprises an acquisition module 111, a determination module 112 and a display module 113. The acquisition module 111 is configured to acquire the first, second and/or third display instruction(s) on the display interface for displaying the three-dimensional human body model, and the three-dimensional human body model comprises: a plurality of tissue layer models classified according to the human body tissue layers, a plurality of human body system models classified according to the human body systems, and/or a plurality of local human body models. The determination module 112 is configured to determine a tissue layer model, a human body system model and/or a local human body model according to the first, second and/or third display instruction(s). The display module 113 is configured to update and display the three-dimensional human body model on the display interface with a tissue layer model, a human body system model and/or a local human body model.

The human body information display device 110 according to the present disclosure may update and display, on the display interface, the three-dimensional human body model as the tissue layer model classified according to the human body tissue layers, a plurality of human body system models classified according to the human body systems and/or a plurality of the local human body models through the obtained display instructions, so that the user may view different tissue layers, systems and/or local parts of the human body by inputting different display instructions, thereby avoiding the problem of mutual penetration or occlusion of organs or tissues, and facilitating users' better observation and understanding of human body information.

In another non-limiting embodiment, the display model may update and display the tissue layer model in a preset format, and the preset format comprises one of the following categories:

displaying the updated three-dimensional human body model in the visual scope of the display interface; or displaying the updated three-dimensional human body model in a predetermined colour; or displaying the three-dimensional human body model other than the tissue layer model with predetermined transparency.

The human body information display device of the embodiment may implement any human body information display method provided by the embodiment of the present disclosure, and its implementation principle is similar, which will not be reiterated herein.

It should be understood that the human body information display method and the human body information display device of the present disclosure may also display at least one of the bones, organs and skin in the three-dimensional human body model according to the received display instruction. It should also be understood that when the skin is displayed simultaneously with bones and/or organs, the skin may be displayed with a certain degree of transparency. In addition, in some other exemplary embodiments, the human body information display method and the human body information display device of the present disclosure may also display the skin of the three-dimensional human body model according to specific requirements, such as the user's customized requirements.

Figure 7:
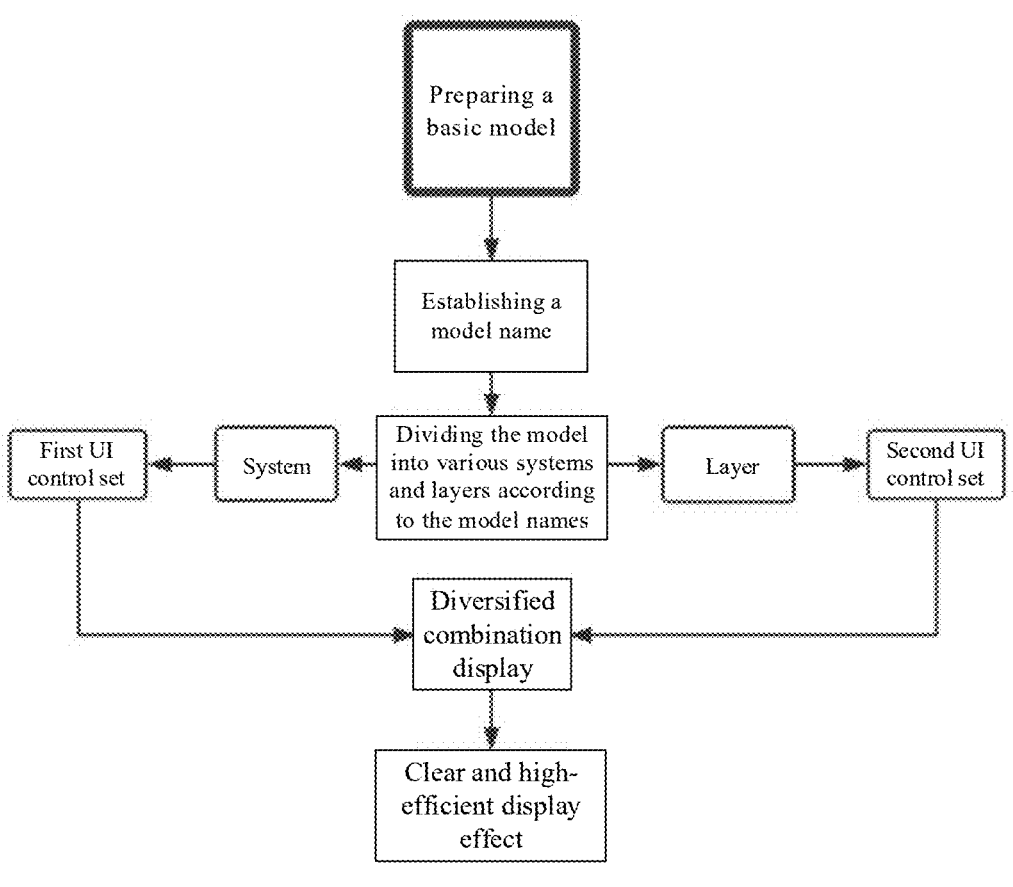
FIG. 7 is a schematic view showing the use flowchart of the human body information display device according to an exemplary embodiment of the present disclosure.

FIG. 7 is a schematic view showing the use flowchart of the human body information display device according to an exemplary embodiment of the present disclosure, which describes a use scenario. As shown in FIG. 7, the relevant applications on computing devices such as mobile phones are launched, a basic model is prepared, and the three-dimensional human body model is displayed on the display interface of the computing device. The three-dimensional human body model is displayed in the form of a complete human body, and the model name is established in the system. According to the model name, the three-dimensional human body model is divided into various systems and layers in advance. According to the layers or according to the "first user interface (UI) control set" and "second UI control set" respectively corresponding to the systems, diversified combinations may be displayed.

Specifically, the lower left corner of the display interface of the computing device is clicked to determine the first display instruction by the finger click at this area, obtain the human body information of the surface muscle tissue layer of the three-dimensional human body model, and display the three-dimensional human body model of the surface muscle tissue layer of the entire human body on the display interface of the computing device. Furthermore, the lower left corner of the display interface of the computing device is clicked to determine another first display instruction, correspondingly obtain the human body information of the middle muscle tissue layer of the three-dimensional human body model, and display the three-dimensional human body model of the middle muscle tissue layer of the entire human body on the display interface of the computing device.

Alternatively, the three-dimensional human body model is displayed on the display interface of the computing device, but the voice instruction "circulatory system" is inputted into the computing device, and the computing device obtains the second display instruction, that is, to display classified "systems" through "first UI control set", and specifically display the content of "circulatory system". Before the three-dimensional human body model is displayed as a tissue layer model, the blood vessels of the entire human body are displayed on the display interface of the computing device. According to the tissue layers, the blood vessels may be divided into arterial blood vessels, venous blood vessels or capillaries etc. Then, the lower left corner of the display interface of the computing device is clicked to obtain the first display instruction, and display classified "layers" through the "second UI control set" to display the arterial blood vessels of the entire human body on the display interface of the computing device.

Alternatively, there are optional menus in software, one of which is "head". By selecting the "head" optional menu, the classified local parts are displayed through a "third UI control set" (not shown). The three-dimensional human body model of the head is displayed in full screen on the display interface of the computing device. Then, the left lower corner of the display interface of the computing device is clicked to obtain the first display instruction, and display the dermis layer of the head on the display interface of the computing device.

Therefore, the human body information display method and device provided by the present disclosure can enable the user to view different tissue layers of the human body by inputting different display instructions, thereby avoiding the problem of mutual penetration or occlusion of organs or tissues, and facilitating users' better observation and understanding of human body information.

Figure 8A:
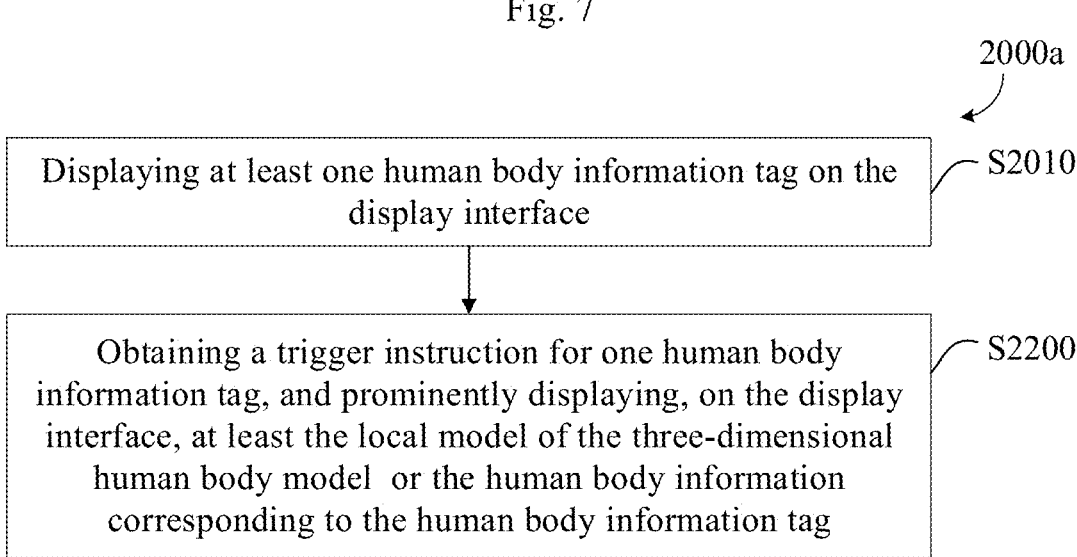
FIG. 8A schematically shows a human body information display method according to another exemplary embodiment of the present disclosure in the form of a flowchart.

Referring to FIG. 8A, it schematically shows a human body information display method 2000a according to another exemplary embodiment of the present disclosure in the form of a flowchart. The human body information display method 2000a may be applied independently or combined with the human body information display method 1000 in FIG. 3 as additional steps. As shown in FIG. 8A, the method comprises the steps of:

S2010: displaying at least one human body information tag on the display interface;

S2200: obtaining a trigger instruction for one human body information tag, and prominently displaying, on the display interface, at least the local model of the three-dimensional human body model or the human body information corresponding to the human body information tag.

It should be understood that in the present disclosure, the term "human body information tag" should be understood in a broad way, which comprises not only the human body information tags displayed in the form of an icon or a list, etc., but also the human body information tags, each of which is one of the different areas obtained by dividing the human body image obtained by displaying the three-dimensional human body model. Therefore, optionally, the human body information display method 2000a may comprise displaying at least one human body information tag in the form of an icon at a specific position of the display interface, such as, around a human body image obtained by displaying the personalized three-dimensional human body model. In addition, optionally, the human body information display method 2000a may also comprise: dividing the human body image obtained by displaying the personalized three-dimensional human body model into a plurality of different areas with each area serving as one of the human body information tags.

Each of FIGS. 8B, 8C, 8D and 8E schematically shows a display interface showing a three-dimensional human body model and human body information tags according to a non-limiting embodiment, and also shows the changing process of the display interface during operation by clicking the human body information tag.

Figures 8B, 8C, 8D, 8E:
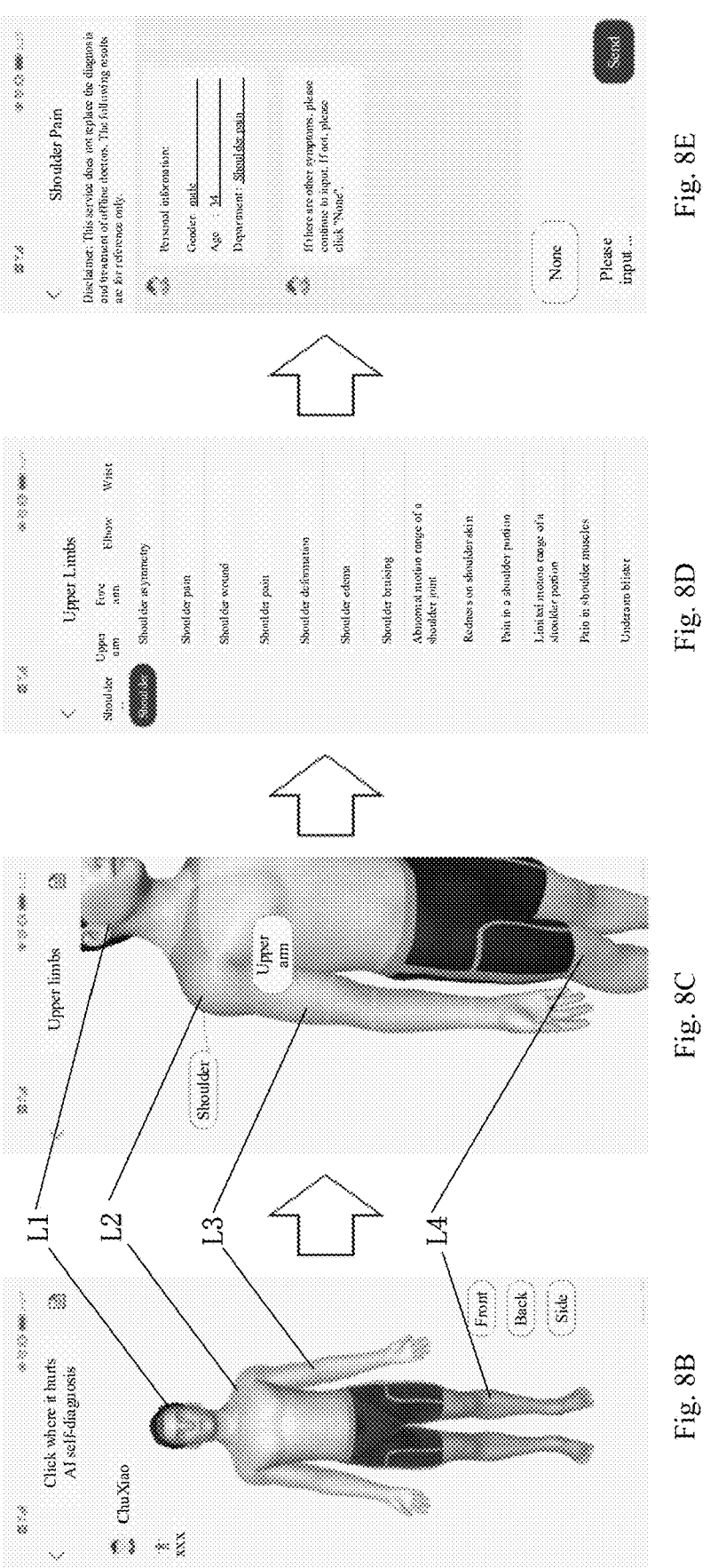

As shown in FIG. 8B, what is initially shown on the display interface is usually a complete three-dimensional human body model, which is generally presented as an upright and naturally stretched three-dimensional human body image. The three-dimensional human body image may be divided into a plurality of different areas, such as a head area L1, a shoulder area L2, an upper limb area L3 and a lower limb area L4 as shown in FIG. 8b. These areas are marked in different colours, indicating that they are human body information tags that may be operated, such as clicking, continuously clicking or continuously contacting. Referring to FIG. 8C, after clicking the shoulder area L2, the display interface magnifies the three-dimensional human body model by a predetermined multiple with the shoulder area L2 of the three-dimensional human body model as a centre and displays the magnified three-dimensional human body model. At this time, the shoulder area L2 may be prominently displayed in a different colour to indicate that the area is selected by the user, and meanwhile may correspondingly display identifier words, such as "Shoulder". Referring to FIG. 8D, as a non-limiting example, after clicking the identifier word "Shoulder", the display interface may display an information list related to "Shoulder", for example, shoulder-related diseases. Finally, as shown in FIG. 8E, after the user clicks the item, such as "Shoulder pain", in the information list, the display interface may be changed into a corresponding questionnaire, so as to clarify the further diagnosis suggestions and/or recommendations, such as diets, exercises, prescriptions, by means of, e.g., symptom feedback and the like. Both information list and questionnaire may involve sorting and storage of diseases in the form of database (multi-layered classification), and may call or update the information in the database stepwise and/or item by item along with the interaction with users.

Referring to FIG. 9, it schematically shows a human body information display method 2000b according to another exemplary embodiment of the present disclosure in the form of a flowchart. The human body information display method 2000b may be applied independently or combined with the human body information display method 1000 in FIG. 3 as additional steps. As shown in FIG. 9A, the method comprises the steps of:

S2100: displaying at least one curve surrounding the three-dimensional human body model on the display interface showing the three-dimensional human body model, and a plurality of human body information tags being disposed along the curve;

S2200: obtaining a trigger instruction for one human body information tag, and prominently displaying, on the display interface, at least the local model of the three-dimensional human body model or the human body information corresponding to the human body information tag.

The present disclosure shows the three-dimensional human body model on the display interface, and can provide a curve with a plurality of human body information tags in the area surrounding the three-dimensional human body model. The trigger instruction of the human body information tag enables the display interface to display the human body information corresponding to the human body information tag, so as to enable users to check the human body information quickly and conveniently according to their own personalized needs, and enhance users' immersion experience by surrounding the three-dimensional human body model with the curve.

For the above Step S2100, the human body information display method provided by the present disclosure generally realizes information interaction with the user through the operation of the electronic device. After the electronic device is turned on to have access to the display interface showing the human body information, what is initially shown on the display interface is usually a complete three-dimensional human body model, which is generally presented as an upright and naturally stretched three-dimensional human body image. In addition, it is possible to observe at least one curve surrounding the three-dimensional human body model on the display interface. In some feasible embodiments, as shown in FIGS. 10A and 10B, the curve comprises at least one of the following: an elliptical arc around the chest position of the three-dimensional human body model; and a helical line spirally extending from the foot of the three-dimensional human body model to the head of the three-dimensional human body model. The curve that is static relative to the display interface. The curve may also be other forms of geometric curves surrounding the three-dimensional human body model, and specifically, there may be one or two curves that are displayed in parallel with a certain gap, or when the curve is a helical line, it may be presented as a double helix structure. Of course, the number of curves may be three or four, etc., which may be set according to the actual needs.

The human body information tag may correspond to different parts of the three-dimensional human body model. Different parts of the three-dimensional human body model may be determined according to different categories. In some feasible embodiments, the human body information tag comprises at least one of the following: human body organ category information, human body system category information, human body parameter information and/or health parameter information; and adjacent human body information tags on the curve are equidistantly spaced. For example, the human body organ category information is classified according to organs, comprising heart, liver, spleen, lung, kidney and the like, or classified according to human body systems, comprising a circulatory system, a digestive system, a respiratory system, a reproductive system, an immune system and the like, or classified according to local parts, comprising head, chest, and upper and lower limbs and the like. Other human body parameter information related to human body health, such as health history data or wound data etc., may also be comprised. These human body information tags may be disposed sequentially along the curve. In order to form a stereoscopic effect, the human body information tags on the curve can be of different sizes, but adjacent human body information tags on the curve are equidistantly spaced, for example, the human body information tags in the middle position are larger, and the human body information tags gradually become smaller as they are further away from the middle position.

Of course, the human body information tags may be set to different states. In some feasible embodiments, the curve comprises a preset prominently-displayed area and a preset non-prominently-displayed area. The step of displaying at least one curve surrounding the human body model on the display interface showing the three-dimensional human body model, the curve being provided with a plurality of the human body information tags, specifically comprises: magnifying and displaying the human body information tag and setting the human body information tag to an active state if the human body information tag is moved to the preset prominently-displayed area; and demagnifying and displaying the human body information tag and setting the human body information tag to an inactive state if the human body information tag is moved to the preset non-prominently-displayed area.

The human body information tag may be moved on the curve, and at a specific position of the curve, for example, on the curved segment close to the central axis of the three-dimensional human body model, the human body information tag is moved to this preset prominently-displayed area, then the human body information tag is in an active state, and the shape is magnified and can be selected, and the next operation can be performed according to the selection. The other areas are preset non-prominently-displayed areas, and the human body information tags in the preset non-prominently-displayed areas are in an inactive state, and displayed in a smaller size accordingly. During the movement of the human body information tag, the magnifying and demagnifying processes are also displayed on the display interface, which can form a vivid stereoscopic dynamic process and improve the user's immersion experience during human-computer interaction. Of course, in addition to magnifying or demagnifying the shape, the feature of changing the brightness and colour of the human body information tag can also be added.

In Step S2100, the content displayed on the display interface is not always in a static state, and the displayed content can be updated according to the specific change of the instruction information obtained from the display interface. In an exemplary embodiment, as shown in FIG. 11, Step S2100 further comprises:

S2110: obtaining sense information from a position sensor or obtaining touch information on the display interface, the touch information comprising at least one of the group comprising a contact position, a contact area, a contact duration or continuous contact information, the continuous contact information comprising start-point position contact information and end-point position contact information.

As a non-limiting example, the position sensor may be a three-axis gyroscope sensor. The signal of the position sensor enables users to operate without touch, so that the operation becomes more convenient and fast. Optionally, the touch information may be obtained by gestures such as touching, sliding or pressing-holding the touch-sensitive display screen, or by operating a mouse such as clicking and dragging the mouse.

S2120: determining first interface action information according to the sense information or the touch information.

Optionally, the instruction specifically corresponding to the touch information can be determined by obtaining the parameter related to the above touch information and/or the information of the three-dimensional human body model on the display interface, for example, the first interface action information can be obtained so as to update the displayed content on the display interface according to the first interface action information.

S2130: updating and displaying the three-dimensional human body model and/or the curve according to the first interface action information.

Optionally, the updated content is the new pose of the three-dimensional human body model, or the new presentation order of the human body information tags on the curve. The curve comprises the human body information tags, and the curve with the human body information tags presented in the new order is the new curve displayed on the display interface, or a combination of the three-dimensional human body model and the new content of the curve.

In an exemplary embodiment, the three-dimensional human body model is presented as a new posture, and the touch information comprises a contact position and a contact duration; the step of updating and displaying the three-dimensional human body model and/or curve according to the first interface action information comprises: magnifying the personalized three-dimensional human body model by a predetermined multiple with the contact position as a centre if the contact position is clicked once or continuously, or the contact duration is larger than a preset trigger duration; and displaying the magnified three-dimensional human body model. When the device detects that a certain position on the display interface is contacted, comprising being touched or clicked by a mouse at the contact position for a period of time, which is greater than the preset trigger time, such as 1 second or 0.5 second, the first interface action information is determined to be the instruction information for magnified display. The position of the three-dimensional human body model to be magnified is determined according to the contact position and the displayed information about the three-dimensional human body model on the display interface so as to magnify the position of the three-dimensional human body model by the predetermined multiple. Of course, the whole three-dimensional human body model is also magnified, but the three-dimensional human body model at the contact position is preferentially displayed on the display interface, so that the user can take the three-dimensional human body model at the position as the key observed object. Optionally, the personalized three-dimensional human body model may be magnified by a predetermined multiple with at least the local model or the human body information tag corresponding to the contact position as the centre. Optionally, at least the local model or the human body information tag corresponding to the contact position may be displayed on the new interface.

In another exemplary embodiment, at least one curve surrounding the three-dimensional human body model is displayed on the display interface displaying the three-dimensional human body model, and a plurality of human body information tags are provided on the curve, comprising: obtaining touch information on the display interface, and determining deflection displacement according to the touch information; and moving all the human body information tags along the curve according to the deflection displacement. This embodiment provides a method process of how to move the human body information tag. The touch information may be obtained on the display interface. Specifically, the touch information may comprise a contact position and continuous contact information. The movement information of the human body information tag is determined according to the contact position and the continuous contact information, and the human body information tag is moved and displayed accordingly. The result after movement may be displayed, and since each movement is a continuous process, it is also possible to display the full process of movement operation.

In one possible implementation of above another specific embodiment, the step of moving all the human body information tags along the curve according to the deflection displacement comprises: determining the rotation angle value of the human body information tag according to the deflection distance of the deflection displacement and the distance between the contact position and the geometric central axis of the curve; and moving the human body information tag along the curve according to the deflection direction of the deflection displacement and the rotation angle value. The deflection displacement obtained from the display interface is a vector comprising the deflection distance and the deflection direction. Take the touch-sensitive screen for example. The defection distance is determined according to the sliding distance on the display interface, and the deflection direction is the sliding direction of the finger on the touch screen. The distance between the contact position and the geometric central axis of the curve can represent the display proportion of the curve on the display interface. If the distance between the contact position and the geometric central axis of the curve is large, it means the curve is displayed in a larger size. If the distance therebetween is small, it means the curve is displayed in a smaller size. If the large size is measured in centimetres, the small size can be considered to be measured in millimetres.

According to the deflection distance and the distance between the contact position and the geometric central axis of the curve, the rotation angle value of the human body information tag on the current display interface can be determined. Then, according to the rotation angle value and the deflection direction in the deflection displacement, the human body information tag is moved on the curve. In addition, it should be explained that since there are a plurality of human body information tags on the curve, they must be arranged in a predetermined order. For example, there are six human body information tags ABCDEF, and the order is in constant circulation, that is, A is next to B and F, B is next to A and C, and so on. After the movement of the human body information tags on the curve, the order with the above adjacency relationships is still maintained.

In another possible implementation of above another non-limiting embodiment, the step of updating and displaying the three-dimensional human body model and/or the curve according to the first interface action information comprises: rotating the three-dimensional human body model according to the deflection displacement; and displaying the rotated three-dimensional human body model on the display interface. According to the implementation provided by the embodiment, the three-dimensional human body model may be moved following the instruction corresponding to the touch information. Not only the human body information tag can be moved along the curve, but also the three-dimensional human body model can be moved so that the user can flip the human body information tag according to the needs to select the checked human body information, and flip and check the three-dimensional human body model. Optionally, the rotation of the three-dimensional human body model itself may be synchronized with the movement of the human body information tag arranged along the curve. As a non-limiting example, the synchronization refers to that the rotation speed value of the three-dimensional human body model itself is proportional to the moving speed value of the human body information tag. Reference can be made to the above-mentioned contents for the specific moving principle of the three-dimensional human body model, which will not be reiterated. In some application scenarios, it is equivalent to keeping the three-dimensional human body model motionless, and the camera that captures the images of the three-dimensional human body model moves with the user's operation, so as to check the three-dimensional human body model from every perspective.

In a feasible embodiment, the three-dimensional human body model rotates on its axis on the display interface at a predetermined rotation speed; the step of displaying at least one curve surrounding the human body model on the display interface showing the three-dimensional human body model comprises: obtaining second interface action information, stopping the rotation of the three-dimensional human body model; and displaying the stopped three-dimensional human body model on the display interface. After the touch information is obtained from the display interface, the touch information can also represent the second interface action information. The three-dimensional human body model is not necessarily displayed as rotating following the user's instructions, but rotates by itself for display. By default, the three-dimensional human body model has been rotating by itself at a certain speed, and the human body central axis is usually selected as the axis of rotation. When the second interface action information is obtained, the second interface action information is also determined according to the touch information, for example, the contact position is located in a preset area, such as in one corner of the display interface, or an area other than the three-dimensional human body model is displayed on the display interface, which is equivalent to stopping the rotation of the three-dimensional human body model by clicking the display interface at these positions, and displaying, on the display interface, the three-dimensional human body model with the pose when it stops rotation.

There are many ways to display the three-dimensional human body model, and there are also other ways to display the curve. In a feasible embodiment, the step of displaying at least one curve surrounding the human body model on the display interface showing the three-dimensional human body model, the curve being provided with a plurality of the human body information tags, comprise: obtaining third interface action information on the display interface; and displaying the curve surrounding the three-dimensional human body model according to the third interface action information. Only the three-dimensional human body model is displayed on the initial interface of the display interface, so that the user can simply check the human body model. Once the touch information is obtained from the display interface, the curve and the human body information tag on the curve will be displayed to facilitate the user's further operation to check other contents. The third interface action information is also determined by the touch information. For example, on a touch screen, as long as the touch screen is detected to be touched, the third interface action information is generated, and it is also possible to maintain the display state of the curve within a certain maintaining time period after the screen is sensed to be touched, and until the preset maintaining time period is exceeded, the curve is concealed. The curve is arranged in a concealable display form so as to make the checking interface concise and clear and allow users to check relevant information conveniently and quickly.

As for Step S2200, in a feasible embodiment, the step of obtaining a trigger instruction for one human body information tag, and prominently displaying, on the display interface, at least the local model of the three-dimensional human body model or the human body information corresponding to the human body information tag comprises: obtaining a trigger instruction within the scope of the display interface where the human body information tag is located. The human body information corresponding to the human body information tag is determined according to the trigger instruction. The human body information is displayed by one of the following ways:

displaying the human body information or at least local model of the three-dimensional human body model corresponding to the human body information within the visual scope of the display interface; or displaying the human body information on the three-dimensional human body model in a predetermined colour; or displaying the three-dimensional human body model in part other than the human body information with a predetermined transparency.

The human body information tag is displayed on the display interface, and when the human body information tag is in the active state, it can be selected and then an instruction be inputted. All human body information tags may be set to the active state, or a part of specific human body information tags may be set to an active state. The trigger instruction of the human body information tag is obtained from the display interface. For instance, when the human body information tag is clicked or double clicked, it goes to the human body information of the selected human body information tag in the system database. For example, when the human body information tag "circulatory system" is clicked, the information of the circulatory system of the human body can be obtained accordingly.

In addition, an explanatory text or further human body information tag can be added correspondingly on the interface prominently displaying the corresponding human body information so as to check more human body information. As shown in FIG. 12, for example, the human body information tag "other" is clicked, the display interface displays the three-dimensional human body model and meanwhile the information tag related to human body information, such as "blood system" or "immune system", and the corresponding information tag is further provided with detailed information index. The displayed content corresponding to each human body information tag may be presented in different forms. As shown in FIG. 13, the human body information tag corresponding to "circulatory system" is clicked to display the three-dimensional human body information of the circulatory system and display the possible detailed descriptive contents in some areas of the display interface.

The selected circulatory system information can be displayed on the three-dimensional human body model in a specific colour to make it distinguishable from other information, and the three-dimensional human body model non belonging to the circulatory system information can also be concealed to prominently display the circulatory system information. If the human body information tag "head" is selected, the head can be displayed in the visual range of the whole display interface, that is, the local model of the three-dimensional human body model, namely the head model, can be displayed in full screen.

In addition to the above-mentioned functions, the human body information display method provided by the present disclosure can realize a human-computer interaction function. In a feasible embodiment, before the step of displaying at least one curve surrounding the three-dimensional human body model on the display interface showing the three-dimensional human body model, the method further comprises: obtaining user's appearance information; determining the combined information of the user's appearance information and the three-dimensional human body model according to the three-dimensional human body model; and displaying the combined information on the display interface. As a non-limiting embodiment, the user's appearance information may be the user's real-time image information. The real-time image information may be obtained by a video camera or a camera, and can also be transmitted to the system through a mobile data storage device. For example, the environment around the device can be obtained by a video camera, and the three-dimensional human body model and the captured environment image can be fitted together to form combined information. The specific image fitting method is known to those skilled in the related field, which will not be reiterated herein. In the combined information that is displayed, the three-dimensional human body model is displayed in the current environment. This embodiment can further improve the realistic display of the three-dimensional human body model and enhance users' immersion experience. As a non-limiting example, an AI face recognition technology can also be applied to the step of obtaining user's appearance information to accurately obtain the user's facial information.

Referring to FIGS. 14a, 14b and 14c, each of which schematically shows a display interface showing a three-dimensional human body model and human body information tags according to an exemplary embodiment. The display interface comprises preset prominently-displayed areas for human body information tags M1 and M2, wherein, for example, the human body information tag M1 may correspond to the respiratory system of a human body, and the human body information tag M2 may correspond to the urinary system of a human body, and the display interface also comprises the human body prominently-displayed area R1 for the three-dimensional human body model. With reference to FIG. 14A, the human body information tag M1 is in the preset prominently-displayed area, and accordingly, the human body prominently-displayed area R1 shows the part of the three-dimensional human body model corresponding to the respiratory system. It should be understood that the human body prominently-displayed area R1 can display the part in the form of at least one of the tissue layer model, human body system model and local human body model. With further reference to FIG. 14B, the human body information tag M1 is being moved out of the preset prominently-displayed area along the curve R2, and the human body information tag M2 is being moved into the preset prominently-displayed area along the curve R2. Correspondingly, the human body prominently-displayed area R1 also slides down to the part corresponding to the urinary system along the three-dimensional human body model and is switched to display the part. With reference to FIG. 14C, the human body information tag M1 has been completely moved out of the preset prominently-displayed area along the curve R2, and the human body information tag M2 has been completely moved into the preset prominently-displayed area along the curve R2. Correspondingly, the human body prominently-displayed area R1 displays the part of the three-dimensional human body model corresponding to the urinary system.

There is no special requirement for the preset prominently-displayed position in the display interface. For example, it can be closer to the centre of the display interface, or a particular position. Optionally, the trigger instruction is not needed for the movement of the human body information tag along the curve, and the human body information tag is moved along the curve repeatedly at a certain speed rate. Optionally, while the human body information tag is moved, the three-dimensional human body model can rotate around its own height direction (that is, the direction extending from the foot of the three-dimensional human body model to its head), and the rotation speed is in a fixed proportion to the moving speed of the human body information tag along the curve. Optionally, the process of the human body information tag entering into the preset prominently-displayed area is a continuously gradual change process. For example, the colour and/or size and/or shape of the human body information tag can be continuously and gradually changed in this process. Optionally, the shape and/or size of the prominently-displayed area of the human body can be changed during the corresponding movement.

In this way, the human body information display method of the present disclosure can compare the local model and the entire model at the same time and further prominently display the contents in the preset prominently-displayed area, so as to display the human body information more vividly, and the human body information tag and its corresponding information and the three-dimensional human body model are linked more timely, so as to bring users' better experience.

Referring to FIGS. 15A and 15B, each of which schematically shows a display interface showing a three-dimensional human body model and human body information tags according to an exemplary embodiment. The display interface comprises preset prominently-displayed areas for human body information tags M1 and M3, wherein, for example, the human body information tag M1 may correspond to the respiratory system of a human body, and the human body information tag M3 may correspond to the circulatory system of a human body. As shown in FIG. 15A, the human body information tag M3 is in the preset prominently-displayed area, and accordingly, the human body prominently-displayed area R1 shows the part of the three-dimensional human body model corresponding to the circulatory system. As shown in FIG. 15B, the human body information tag M1 is in the preset prominently-displayed area, and accordingly, the human body prominently-displayed area R1 shows the part of the three-dimensional human body model corresponding to the respiratory system. As stated above, the human body prominently-displayed area R1 can display the part in the form of at least one of the tissue layer model, human body system model and local human body model. For some reason, for example, when the health assessment module 11 identifies the user's physical examination report to obtain the health parameter information related to human health of the user, and identifies the abnormal information of the user's respiratory system according to the physical examination report. Therefore, the human body information tag M1 corresponding to the human body respiratory system can be displayed in a differential way to remind the user to pay attention. In FIG. 15B, the human body information tag M1 is displayed differentially in a different colour and with a dot added to the upper right corner of the icon. However, it should be understood that any suitable way to display the human body information tags differentially can be adopted.

Referring to FIG. 16, it schematically shows a human body information display device 210 according to an exemplary embodiment of the present disclosure. The human body information display device 210 may comprise a display module 211 and a feedback module 212. The display module 211 is configured to display at least one curve surrounding the three-dimensional human body model on the display interface showing the three-dimensional human body model, the curve being provided with a plurality of the human body information tags; and the feedback module 212 is configured to obtain a trigger instruction one human body information tag, and prominently display, on the display interface, at least the local model of the three-dimensional human body model or the human body information corresponding to the human body information tag.

The human body information display device 210 provided by the present disclosure can show the three-dimensional human body model on the display interface, and provide a curve with a plurality of human body information tags in the area surrounding the three-dimensional human body model. The trigger instruction of the human body information tag enables the display interface to display the human body information corresponding to the human body information tag, so as to enable users to check the human body information quickly and conveniently according to their own personalized needs, and enhance users' immersion experience by surrounding the three-dimensional human body model with the curve.

In another exemplary embodiment, there is provided another human body information display device, and the display module of the human body information display device further comprises an acquisition unit, a combination unit and an output unit. The acquisition unit is configured to obtain real-time image information. The combination unit is configured to determine the combined information of the real-time image information and the three-dimensional human body model according to the three-dimensional human body model. The output unit is configured to display the combined information on the display interface.

The human body information display device provided by the present disclosure can implement the human body information display method shown in any embodiment of the present disclosure, and its implementation principle is similar, which will not be reiterated herein.

Referring to FIG. 17, it schematically shows a human body information display device according to a further exemplary embodiment of the present disclosure in the form of a block diagram. The human body information display device comprises: one or more processors; a memory; one or more application programs stored in the memory and configured to be executed by the one or more processors, wherein the one or more application programs are configured to implement the human body information display method as shown in any embodiment of the present disclosure.

Compared with the related art, the human body information display device provided by the present disclosure can facilitate the user to check the human body information quickly and conveniently according to the user's personalized needs, and enhance the user's immersion experience and improve the human-computer interaction efficiency by encircling the three-dimensional human body model with a curve.

As shown in FIG. 17, the human body information display device 300 comprises a processor 301 and a memory 303. The processor 301 and the memory 303 are connected by, for example, a bus 302. Optionally, the human body information display device 300 may further comprise a transceiver 304. It should be explained that the transceiver 304 may not be limited to one in practical applications. The structure of the human body information display device 300 does not constitute a limitation to the embodiments of the present application.

The processor 301 may be a central processing unit (CPU), a general purpose processor, a digital signal processor (DSP), an application specific integrated circuit (ASIC), a field programmable gate array (FPGA) or other programmable logic devices, transistor logic devices, hardware components or any combination thereof. It may implement or execute various exemplary logical blocks, modules and circuits described in connection with the contents of the present disclosure. The processor 301 may also be a combination for realizing a computing function, for example, a combination comprising one or more microprocessors, or a combination of a DSP and a microprocessor, or the like.

The bus 302 may comprise a pathway for transmitting information between the above components. The bus 302 can be a peripheral component interconnect (PCI) bus or extended industry standard architecture (EISA) bus, or the like. The bus 302 can be divided into an address bus, a data bus, a control bus and the like. For easy representation, there is only one thick line in FIG. 17 to represent a bus, but it does not mean that there is only one bus or one type of buses.

The memory 303 can be a read only memory (ROM) or other types of static storage devices that can store static information and instructions, a random access memory (RAM) or other types of dynamic storage devices that can store information and instructions, or an electrically erasable programmable read only memory (EEPROM), a compact disc read only memory (CD-ROM) or other optical disk storage, optical disc storage (including a compact disc, a laser disc, an optical disc, a digital versatile disc, a blue-ray disc, etc.), magnetic disk storage media or other magnetic storage devices, or any other medium that can be used to carry or store a desired program code in the form of an instruction or data structure and can be accessed by a computer. But the memory is not limited thereto.

The memory 303 is configured to store an application program code for executing various solutions of the present disclosure, which can be controlled and executed by the processor 301. The processor 301 is configured to execute the application program code stored in the memory 303 to realize the contents shown in any of the above method embodiments.

Referring to FIG. 18, it schematically shows a human body model generation method 3000 according to an exemplary embodiment of the present disclosure in the form of a flowchart. The flowchart schematic view of the method as shown in FIG. 18 comprises steps S3101 and S3102:

S3101: obtaining an actual human body parameter of a user;

S3102: processing a typical variable human body model in a variable human body model library according to the actual human body parameter to obtain a personalized variable human body model corresponding to the actual human body parameter.

In the exemplary embodiment of the present disclosure, the typical variable human body model in the variable human body model library is obtained by means of big data calculation based on a large number of real sample human body data. The diversity and authenticity of samples can ensure that the typical variable human body model is highly precise, such that the personalized variable human body model obtained by processing the typical variable human body model is highly precise; and compared with the conventional statistical calculation method, the method of the present disclosure can greatly reduce the amount of calculation, decrease costs, and shorten the processing time, so that the hardware device with general processing capacity can also apply the personalized variable human body model processing method provided by the embodiment of the present disclosure, so as to broaden the scope of application. It should be understood that the step of obtaining an actual human body parameter of a user can also be realized by identifying the physical examination report of the user through the health assessment module 11.

Optionally, the exemplary embodiment of the present disclosure provides a method for obtaining a typical variable human body model and a method for deploying and processing a variable human body model based on a typical variable human body model.

In the exemplary embodiment of the present disclosure, the flowchart schematic view of a method 3000a for obtaining a typical variable human body model is shown in FIG. 19A, and comprises the following steps S3211 and S3212:

S3211: extracting a typical human body parameter from variable model original data.

Optionally, the variable model original data comprises: a plurality of sample body parameters with each comprising at least one type of human body physical sign data of an actual human body. Each sample body parameter can represent real body characteristics of an actual human body, and can be used to build a three-dimensional human body model (i.e., an actual human body model).

The types (i.e., categories) of the human body physical sign data involved in each sample human body parameter include but are not limited to the following types: age, fat content (or body fat rate), head circumference, neck circumference, chest circumference, upper chest circumference, lower chest circumference, abdominal circumference, hip circumference, back length, shoulder width, upper arm length, lower arm length, upper arm circumference, thigh length, thigh circumference, calf circumference, and the ratio of front waist length to back waist length.

In the exemplary embodiment of the present disclosure, the number of types of human body physical sign data included in various sample human body parameters may be the same or different. When the types of human body physical sign data included in various sample human body parameter are the same, the three-dimensional human body models constructed based on various sample human body parameters are relatively uniform, which can provide a unified processing benchmark for subsequent model processing; and when the types of human body physical sign data included in various sample human body parameters are different, the types of human body physical sign data that are missing in the sample human body parameters having fewer types can be supplemented based on the sample human body parameter having the most types, so that the types of human body physical sign data included in various sample human body parameters are the same, thereby constructing a unified three-dimensional human body model for subsequent processing.

In a non-limiting example, suppose the sample human body parameter A comprises 8 types of human body physical sign data, including age, height, weight, head circumference, shoulder width, chest circumference, waist circumference and hip circumference, and comprises the most types of the human body physical sign data among various sample human body parameters, other sample human body parameters except the sample human body parameter A can be supplemented based on the types of the sample human body parameter A. Take the sample human body parameter B as an example. Suppose the sample human body parameter B only comprises 5 types of human body physical sign data, including age, height, weight, head circumference and shoulder width, data that are missing in the sample human body parameter B in comparison with the sample human body parameter A, i.e., data in relation to chest circumference, waist circumference and hip circumferences, can be supplemented according to default values that can be set according to actual needs. For example, based on any type of human body physical sign data in the sample human body parameter B, the missing data in relation to chest circumference, waist circumference and hip circumferences are determined based on the mapping relationships between different types of human body physical sign data in the parameter mapping library as mentioned above.

Optionally, each type of human body physical sign data has a corresponding relationship with some or all three-dimensional vertices (surface vertices) in the three-dimensional model. In one example, age can have a corresponding relationship with all three-dimensional vertices in the three-dimensional model. As the age changes, all three-dimensional vertices in the three-dimensional model will change accordingly. The main parts involved comprise back, abdomen, legs, and the like. As the age increases, the change of three-dimensional vertices of the back may lead to the bending of the back in the three-dimensional model to some extent, which may cause humpback (for example, the elderly versus the youth), the change of the three-dimensional vertices of the abdomen may lead to abdominal thickening (for example, the middle-aged versus the youth), and the change in the three-dimensional vertices of the legs can cause the legs to become longer (for example, adult versus juvenile).

The three-dimensional vertex information of the corresponding three-dimensional model can be generated according to the human body physical sign data. The three-dimensional vertex information comprises the coordinates of three-dimensional vertices, the connection relationships between the three-dimensional vertices, and the corresponding relationships between the three-dimensional vertices.

In an optional embodiment, in addition to the human body physical sign data, each sample human body parameter also comprises three-dimensional vertex information, specifically the three-dimensional vertex information of the actual human body and the three-dimensional vertex information of each part of the actual human body.

The three-dimensional vertex information of the actual human body can comprise the three-dimensional vertex information of some or all parts of the actual human body.

The three-dimensional vertex information of various parts of the actual human body can comprise: the three-dimensional vertex information of various local parts, such as the head and neck, chest, upper limbs, lower limbs, pelvic perineum, abdomen, spine and the like, of the actual human body, as well as the three-dimensional vertex information of various human body systems, such as the motor system, urinary system, respiratory system, visual system, oral system, circulatory system, blood system, immune system and the like, of the actual human body. The three-dimensional vertex information of the human body system of each actual human body comprises the three-dimensional vertex information of human body tissues and/or human body organs of the actual human body. For example, the three-dimensional vertex information of the motor system comprises the three-dimensional vertex information of various tissues, such as bones, joints, muscles and the like.

The sample human body parameter in the variable model original data can be calculated from the big data according to the statistical algorithm. The basic statistical data can be real human body images, such as computed tomography (CT) images. A large number of real human body models can be obtained by means of three-dimensional modelling of a large number of real human body CT images, and the actual human body parameters of a large number of users can be obtained by the statistical method at a time, and the data cover a wide range.

Optionally, the number of sample human body parameters (i.e., the number of items, corresponding to the number of actual human bodies) in the variable model original data can be the number greater than a preset threshold. The preset threshold can be determined according to the actual needs or empirical values. For example, the preset threshold can be set to 100, and the number of obtained actual human body parameters is greater than 100.

Compared with the related art, the sample data of the typical variable human body model constructed by the exemplary embodiment of the present disclosure involve a great number of users, the data quantity of the actual human body parameters of a single user is rich, and is conducive to pre-calculation and beneficial to obtaining the shape-changing rule of actual humans through statistics or comparison of these rich data, thereby reflecting the real differences between different individuals of the actual humans.

In an optional embodiment, the step of extracting a typical human body parameter from the variable model original data comprises: determining at least one physical sign characteristic value of each type of the human body physical sign data according to the human body physical sign data in the plurality of sample human body parameters; and determining one typical human body parameter according to each of the physical sign characteristic values.

Corresponding to the actual human body parameter, in an optional embodiment, the typical human body parameter may also comprise at least one type of typical human body physical sign data, such as gender, age, height, weight and the like; and in another optional embodiment, the typical human body parameter comprises at least one type of typical human body physical sign data, as well as a typical human body (i.e., the three-dimensional vertex information of a typical human body) and three-dimensional vertex information of various parts of the typical human body.

The three-dimensional vertex information of the typical human body can comprise the three-dimensional vertex information of some or all parts of the typical human body.

The three-dimensional vertex information of various parts of the typical human body can comprise: the three-dimensional vertex information of various local parts, such as the head and neck, chest, upper limbs, lower limbs, pelvic perineum, abdomen, spine and the like, of the typical human body, as well as the three-dimensional vertex information of various human body systems, such as the motor system, urinary system, respiratory system, visual system, oral system, circulatory system, blood system, immune system and the like, of the typical human body. The three-dimensional vertex information of the human body system of each typical human body comprises the three-dimensional vertex information of human body tissues and/or human body organs of the typical human body. For example, the three-dimensional vertex information of the motor system comprises the three-dimensional vertex information of various tissues, such as bones, joints, muscles and the like.

In the embodiment of the present disclosure, the coordinates of the three-dimensional vertex can be in the form of the three-dimensional coordinates (x, y, z) or UV coordinates. UVW is used to represent the mapping coordinate system, and represents a plane map in the three-dimensional space, wherein U represents the transverse direction, V represents the longitudinal direction, and W represents the direction perpendicular to a screen.

Optionally, the three-dimensional vertex information can be stored in the form of a binary file, such as .fbx format and .dat format, to reduce redundancy and save storage space, and ensure the accuracy of data. It can also be stored in a text format, such as .obj format.

The inventors of the present disclosure have found through studies that the change of the variable human body model largely depends on the change of the vertex position of the variable human body model, and the vertex connection relationships, UV coordinates, and corresponding relationships between vertices of the variable human body model are fixed.

Therefore, fixed information, such as the vertex connection relationships, UV coordinates, corresponding relationships between vertices of the variable human body model and the like, are extracted in advance from the variable model original data obtained by big data calculation, and stored in the hardware devices executing various methods in the present disclosure. Optionally, the file containing the fixed information can be converted into a binary file for storage.

Optionally, the file containing the variable model original data is converted into a .fbx model file, and the three-dimensional vertex information can be extracted from the .fbx model file by using three-dimensional processing software. The three-dimensional processing software can be 3d Max or Unity. The 3d Max, namely 3D Studio Max, is computer-system-based 3D animation rendering and production software developed by Discrete Inc. (later merged by Autodesk Inc.).

Optionally, the physical sign characteristic value in the exemplary embodiment of the present disclosure can be any one of the maximum value, minimum value, average value and other value, wherein the other value can be a value selected in the range between any two values of the maximum value, minimum value and average value, and the specific type thereof can be determined according to the actual situation. For a certain type of human body physical sign data, such as height, the maximum, minimum and average height of a plurality of users can be determined as the three physical sign characteristic values of height.

The physical sign characteristic value of a certain type of human body physical sign data in the exemplary embodiment of the present disclosure can reflect the change characteristics of the type of human body physical sign data in various sample human body parameters obtained based on the real humans, such as two extreme changes reflected by the maximum and minimum values of this type of human body physical sign data, and the average change reflected by the average value of this type of human body physical sign data. The typical human body parameter determined based on the change characteristics can better reflect the characteristics of human body shape change caused by this type of human body physical sign data. When there are many types of human body physical sign data, a typical human body parameter determined by each type of human body physical sign data can reflect a part of the characteristics of human body shape change, so that the plurality of typical human body parameters finally obtained can more comprehensively reflect the overall shape change rule of real humans, and are more referential in the personalized model customization stage, and that the personalized variable human body model can reflect the user's body characteristics more accurately.

At the same time, for M-type human body physical sign data, the number of physical sign characteristic values of each type of human body physical sign data is usually small (for example, 2 or 3), and the number of types of human body physical sign data that are frequently used in daily life, that is, the number of M, is also small (for example, less than 10). Therefore, the number of typical human body parameters (namely items, for example, 2M or 3M) determined based on physical sign characteristic values is also small. In order to achieve accurate personalized customization, the number of the selected sample human body parameters is usually large (more than 100), and the number of the typical human body parameters determined based on the physical sign characteristic value is obviously less than the number of the selected sample human body parameters. Thus, in comparison with the manner for directly utilizing an original sample human body parameter, the scheme of determining a typical human body parameter based on the physical sign characteristic value in the embodiment of the present disclosure can greatly reduce the number of human body models referred to in the personalized model customization stage.

Optionally, the step of determining at least one physical sign characteristic value of each type of the human body physical sign data according to the human body physical sign data in the plurality of sample human body parameters comprises: constructing a plurality of actual human body models according to the plurality of sample human body parameters; detecting the change information of each type of the human body physical sign data in each of the actual human body models; and determining at least one physical sign characteristic value of each type of the human body physical sign data according to the change information.

Optionally, the change information of each type of the human body physical sign data in each actual human body model can be detected by the following manners: setting a plurality of parameter marker points in each actual human body model, the parameter marker points having a corresponding relationship with the human body physical sign data, wherein it is possible to set the same parameter marker points at the same positions (such as the three-dimensional vertices of all parts or the same parts of the actual human body model) in different actual human body models; and obtaining the change information of each type of the human body physical sign data in each actual human body model by detecting the change information of each parameter marker point in each actual human body model.

Optionally, the step of determining one typical human body parameter according to each of the physical sign characteristic values comprises: for each physical sign characteristic value, regarding the physical sign characteristic value as a type of human body physical sign data in a typical human body parameter; and determining other types of human body physical sign data in the typical human body parameter according to the physical sign characteristic value and the mapping relationship between different types of human body physical sign data.

For each physical sign characteristic value, the typical human body parameter determined by the method (that is, the above-mentioned method for determining a parameter based on the mapping relationship between different types of human body physical sign data) is the typical human body parameter with a certain physical sign characteristic. For example, for the maximum height, after other human body physical sign data, such as weight, chest circumference, waist circumference and the like, are determined by the method, the maximum height, and the determined weight, chest circumference, waist circumference and the like, form the typical human body parameter in the case of maximum height. Similarly, for the minimum height, the typical human body parameter in the case of the minimum height can be obtained. For the average height, the typical human body parameter in the case of average height can be obtained. For height, if the physical sign characteristic value is a value between the maximum value and the average value, a typical human body parameter in the case of a height on the tall side can be obtained. Similarly, for a value between the minimum value and the average value, a typical human body parameter in the case of a height on the short side can be obtained.

For other human body physical sign data other than height, at least one typical human body parameter of various body types can be determined in the same way.

The mapping relationship between different types of human body physical sign data can be established in advance and stored in a parameter mapping library for use. The mapping relationship between different types of human body physical sign data can be established according to the change rules of different types of human body physical sign data. For example, the change of height usually brings about the changes of other human body physical sign data such as weight, chest circumference, waist circumference and the like. When the height increases by a fixed value, other human body physical sign data such as weight, chest circumference, waist circumference and the like will increase or decrease by the corresponding value. The specific change rule can be determined based on the statistics of various actual human body parameters of the actual humans, and the determined change rules can be stored in the parameter mapping library.

Optionally, the change rules of different types of human body physical sign data can be expressed by the proportional relationship between different types of human body physical sign data, or by the proportional relationship between the change values of different types of human body physical sign data. The data stored in the parameter mapping library can be the above proportional relationship, or the combination of a plurality of human body physical sign data in line with the above change rules.

In a non-limiting example, during storage, for a stored human body physical sign data (such as height), the value obtained by multiplying the human body physical sign data by the corresponding proportion coefficient may be used as other human body physical sign data such as weight, chest circumference, waist circumference and the like, and stored in the parameter mapping library together with height.

The mapping relationship between different types of human body physical sign data is established by taking into account the influence between different types of human body physical sign data, which can make the selection of typical human body parameters more accurate and more referential.

In another optional embodiment, the step of extracting a typical human body parameter from the variable model original data comprises: for each type of human body physical sign data, respectively selecting the type of human body physical sign data in a standard value range, a larger value range and a smaller value range from the type of human body physical sign data of a plurality of actual human bodies; and using various types of human body physical sign data in different ranges as the typical human body parameters of different body types, to be specific, using various types of human body physical sign data in the standard value range as typical human body parameters of a standard body type, using various types of human body physical sign data in the larger value range as typical human body parameters of an overweight body type, and using various types of human body physical sign data in the smaller value range as typical human body parameters of a slim body type.

Body types of actual humans may be substantially divided according to the method for extracting the typical human body parameter to obtain typical human body parameters of different body types. Based on the typical physical body parameters of different body types, the typical human body models of different body types can be obtained to reflect the body type characteristics of actual humans. In the personalized model customization stage, different customization benchmarks can be provided for different users, so as to achieve the purpose of personalized customization, while reducing the amount of calculation.

Optionally, the step of constructing a plurality of actual human body models according to a plurality of actual human body parameters comprises: generating one actual human body model according to each sample human body parameter to obtain the plurality of actual human body models; and normalizing the plurality of actual human body models to make the positions and angles of the plurality of actual human body models consistent in the same three-dimensional space.

Through the above normalization processing, the position and angle of each actual human body model in the three-dimensional space are unified, which can provide a unified benchmark for the subsequent steps (such as the detection of the physical sign characteristic value and shape change characteristic value and parameter marker points), so as to make the detection and calculation more accurate, and the obtained typical human body parameters more referential.

Optionally, for each user, when the actual human body model of the user is generated according to the actual human body parameter, a binary file is created. The actual human body model and its actual human body parameter are converted into a binary format so as to be written into the binary file.

Optionally, the model name of the actual human body model in a binary format, the number of vertices of the actual human body parameter in a binary format, and the three-dimensional positions of the vertices of the actual human body parameter in a binary format are written into the binary file layer by layer.

For each user, when the actual human body model of the user is generated according to the actual human body parameter, a plurality of three-dimensional vertex information can be generated according to the actual human body parameter, so as to generate the actual human body model formed by the plurality of three-dimensional vertex information.

Optionally, the step of normalizing the plurality of actual human body models to make the positions and angles of the plurality of actual human body models consistent in the same three-dimensional space comprises: selecting any one of the actual human body models as an initial model; and moving and rotating the rest of the actual human body models in the same three-dimensional space sequentially until the position and angle of the moved and rotated actual human body model in the three-dimensional space are consistent with the position and angle of the initial model in the three-dimensional space.

The method for moving and rotating the plurality of actual human body models one by one with reference to the initial model can realize the accurate adjustment of each actual human body model, which is conducive to maintaining the consistency of various actual human body models.

The commonly used Proctor analysis method needs to process different individuals in terms of the three dimensions of position, angle and size, that is, to move, rotate and perform scaling on different individuals respectively. In the embodiment of the present disclosure, considering that body size is an important morphological difference between different users, if perform scaling on sizes for normalization, the important morphological difference may be ignored, which is disadvantageous to the construction of the personalized variable human body model. Thus, in the embodiment of the present disclosure, only the movement and rotation are performed instead of scaling.

Optionally, after moving and rotating each actual human body model by the above steps, the position and angle errors between every two actual human body models are calculated. For the actual human body model whose position and angle errors are greater than the error threshold, the above normalizing step is performed again to ensure the high consistency of the actual human body models in terms of position and angle, in such a way to provide a more unified benchmark for the subsequent steps and improve the accuracy of subsequent detection and calculation.

In an optional embodiment, if a plurality of actual human body models are taken as samples, the plurality of actual human body models are normalized, that is, the plurality of sample shapes are normalized.

In one example, a plurality of samples in a training set are normalized as follows: 1) estimating an initial average shape (selecting any shape in the training set in the first iteration); 2) aligning the shapes in the training set to the shape by the normalization method of the Proctor analysis method; 3) recalculating the average shape of the aligned samples; 4) repeating the step 2) until the convergence condition is satisfied.

S3212: Generating the typical variable human body model according to the typical human body parameter.

Optionally, the file of a typical variable human body model is created and the typical human body parameter is written into the file.

Optionally, the three-dimensional vertex information corresponding to the typical human body parameter is written into the file of the typical variable human body model.

According to the different typical human body parameters, the typical variable human body models can be diversified, including the typical variable human body models of every age, gender, region and the like.

In an optional embodiment, a typical variable human body model with the maximum height can be obtained according to the previously determined typical human body parameter with the maximum height, a typical variable human body model with the minimum height can be obtained according to the typical human body parameter with the minimum height, and a typical variable human body model with an average height can be obtained according to the typical human body parameter with the average height. Other human body physical sign data, such as weight, chest circumference, waist circumference and the like, are the same.

In another optional embodiment, a typical variable human body model of the standard body shape can be obtained according to the above determined typical human body parameter of the standard body shape, a typical variable human body model of the overweight body shape can be obtained according to the typical human body parameter of the overweight body shape, and a typical variable human body model of the slim body shape can be obtained according to the typical human body parameter of the slim body shape.

The typical variable human body models obtained by the above various methods can better reflect the shape change characteristics (such as the maximum height, the minimum height, the maximum weight and the like) or body shape characteristics (such as standard body type, overweight body type, slim body shape and the like) of the real humans, which can provide a reliable model basis for personalized customization of human body models, and reduce the number of models or the amount of data and the calculation amount and improve the calculation efficiency in comparison with the customized method based on the real human original data or the actual human body model.

As shown in FIG. 19B, the flowchart schematic view of another method 3000b for obtaining a typical variable human body model in the embodiment of the present disclosure comprises the following steps S3221 to S3223:

S3221: Constructing a plurality of actual human body models according to a plurality of sample human body parameters.

Each of the sample human body parameters comprises at least one type of human body physical sign data of an actual human body (that is, a real human body). Each sample human body parameter can construct an actual human body model, and each actual human body model can reflect the real body characteristics of an actual human body.

As mentioned above, a plurality of sample human body parameters can be calculated from big data according to statistical algorithm and stored in advance as the variable model original data.

As mentioned above, the number of the types of human body physical sign data included in various sample human body parameters may be the same or different. If different, the types of human body physical sign data that are missing in various sample human body parameters having fewer types can be supplemented based on the sample human body parameter having the most types, so that the types of human body physical sign data included in various sample human body parameters are the same, thereby constructing a unified actual human body model for subsequent processing.

S3222: Determining a principal shape change component of each actual human body model and a shape change characteristic value corresponding to the principal shape change component by a principal component analysis method.

S3223: Determining the typical variable human body model according to the principal shape change component and the shape change characteristic value.

In an optional embodiment, at least one typical human body parameter is determined according to the principal shape change component and shape change characteristic value, and a typical variable human body model is determined according to each determined typical human body parameter as a typical variable human body model reflecting shape change characteristics. Wherein, the step of determining at least one typical human body parameter according to the principal shape change component and shape change characteristic value may comprise: adjusting the human body parameter of the basic human body model according to the principal shape change component and the shape change characteristic value to obtain at least one typical human body parameter.

In another optional embodiment, the three-dimensional vertex information of the basic human body model can be adjusted directly according to the principal shape change component and the shape change characteristic value to obtain a corresponding typical variable human body model.

In some examples, since the human body parameters of the human body model are associated with the three-dimensional vertex information, there may be no clear order of precedence between the determination of the typical human body parameters and the determination of the typical variable human body model. The determination of the typical variable human body model may not depend on the typical human body parameters, or the typical variable human body model may be determined by directly adjusting the three-dimensional vertex information. Therefore, in some embodiments, the human body parameters and three-dimensional vertex information in the basic human body model can be adjusted synchronously according to the principal shape change component and the shape change characteristic value so as to obtain the typical human body parameters and their corresponding typical variable human body models at the same time.

The principal shape change component is the component that can cause the partial shape change of the three-dimensional model. The basic human body model can be a three-dimensional human body model generated according to the averages value of the actual human body parameters of a plurality of users, or a three-dimensional human body model generated according to other parameter values set as required.

The principle of the above process is introduced hereinafter in view of a specific example:

Suppose that there are m actual human body models as the samples of principal component analysis, and each real human body model comprises n curved surface vertices as parameter marker points. In the process of principal component analysis, each actual human body model is first represented by the column vector of the coordinate set of n curved surface vertices as follows:

$$X_i = \left[ x_1^i, y_1^i, z_1^i, x_2^i, y_2^i, z_2^i, \quad \ldots \quad \ldots \quad , x_n^i, y_n^i, z_n^i \right]^T \qquad \text{Equation (1)}$$

In the equation (1), i represents the sample number, that is, the number of the real human body model used as the sample in the example of the present disclosure.

Then, the average shape vector of all samples (which can be used as the human body parameter vector of the basic human body model) is calculated by the following manner:

$$\overline{X} = \frac{1}{m} \sum_{i=1}^{m} X_i \qquad \text{Equation (2)}$$

Furthermore, the covariance matrix of each sample is calculated by the following manner:

$$S = \frac{1}{m-1} \sum_{i=1}^{m} \left( X_i - \overline{X} \right)^T \cdot \left( X_i - \overline{X} \right) \qquad \text{Equation (3)}$$

Furthermore, the principal shape change component (characteristic vector) $\phi_m$ and its corresponding shape change characteristic value $\lambda_m$ of the covariance matrix S are obtained by means of singular value decomposition (SVD). The principal shape change component (characteristic vector) $\phi_m$ and its corresponding shape change characteristic value $\lambda_m$ can maintain the principal data information of the original m samples to a large extent so as to reflect the shape change characteristics of the original m samples, and meanwhile delete irrelevant or repeated data information so as to reduce the calculation amount.

All the obtained shape change characteristic values are sorted in order from large to small. The first largest c shape change characteristic values $\lambda_m$ are selected as an estimate of all the shapes of samples in the entirety. The shape of each human body may be expressed as follows:

$$X = \overline{X} + \sum_{m=1}^{c} b_m \phi_m \qquad \text{Equation (4)}$$

In the equation (4), $b_m$ represents a shape coefficient, which can be regarded as the compressed expression of the sample shape. Other parameters have the same meaning as above.

$\hat{X}$ can be adjusted by adjusting the shape coefficient $b_m$. The value of the shape coefficient $b_m$ can be determined according to the shape change characteristic value $\lambda_m$, and then is inserted into the equation (4) to determine a typical variable human body model X. The corresponding relationship between the shape change characteristic value $\lambda_m$ and the shape coefficient $b_m$ may be determined according to actual needs or empirical value, for example, $b_m \pm 3\sqrt{\lambda_m}$, wherein 3 may be replaced by other value according to actual needs.

In an optional embodiment, where the shape coefficient $b_m$ is unknown, X may also be stored as a typical variable human body model in the variable human body model library.

In fact, in the exemplary embodiment of the present disclosure, there are many types of typical human bodies and many types of typical variable human body models, and each typical variable human body model can be obtained from the above steps S3211 to S3212 or S3221 to S3223.

Optionally, on the basis of the above steps S3211 to S3212 or on the basis of steps S3221 to S3223, another method for obtaining a typical variable human body model in the exemplary embodiment of the present application further comprises the following step:

converting the file of the typical variable human body model into a binary file for storage, the binary file of the typical variable human body model comprising a typical human body parameter in a binary format.

Optionally, a binary file is created; and the typical variable human body model and its typical human body parameter are converted into a binary format and written into the binary file.

Optionally, the model name of the typical variable human body model in a binary format, the number of vertices of the typical human body parameter in a binary format, and the three-dimensional positions of vertices of the typical human body parameter in a binary format are written into the binary file layer by layer.

Optionally, the binary file is stored by means of a Unity script. Unity3D developed by Unity Technologies is a multi-platform comprehensive development tool, which allows users to easily create interactive contents such as three-dimensional video games, architectural visualization, or real-time three-dimensional animation, and a comprehensively integrated professional engine. It is simply deployed and user-friendly, has large-scale plug-ins and middleware to accelerate development speed, and supports scripts based on C# language, which can achieve a suitable balance between beautiful programming and efficient running.

By means of the embodiment of the present disclosure, when a large number of variable human body models are stored, the fixed information which is universal to each variable human body model can be saved only once. Only the three-dimensional vertex information needs to be stored for a large number of variable human body models, which saves a large number of processing steps such as extracting and maintaining the fixed information of the variable human body model, and is also conducive to saving the amount of calculation in the subsequent steps and saving the storage space occupied by storing a large number of variable human body models.

Optionally, in the embodiment of the present disclosure, there is provided a method 3000c for deploying and processing a variable human body model based on a typical variable human body model. As shown in FIG. 20A, the flowchart schematic view of the method comprises the following steps S3301 to S3303:

S3301: Obtaining an actual human body parameter of a user.

The meaning of the actual human body parameter is the same as stated above, which will not be reiterated herein.

S3302: Processing a typical variable human body model in a variable human body model library according to the actual human body parameter to obtain a personalized variable human body model corresponding to the actual human body parameter.

Optionally, the gender of the user is determined according to the actual human body parameter; and the typical human body model of the gender in the variable human body model library is processed to obtain a personalized variable human body model corresponding to the actual human body parameter.

Reference can be made to the above-mentioned contents related to S3210 to S3202 for the method for obtaining the typical variable human body model of each gender. Because the body characteristics of users with different genders may vary greatly, the typical variable human body models are respectively created for different genders so as to make the construction of models more relevant. The typical variable human body models with the same gender can reflect the real differences of the actual humans with that gender. Based on the typical variable human body models with the same gender, the personalized human body models of the target users are customized, such that the personalized variable human body models have higher quality, and can better reflect the identity characteristics of the target users.

The typical variable human body models with different genders can be stored in different folders to facilitate subsequent use.

S3303: Converting the file of the personalized variable human body model into a binary file and outputting the same, the binary file of the personalized variable human body model comprising a personalized variable human body parameter in a binary format.

In an optional implementation, the personalized variable human body parameter comprises at least one type of personalized human body physical sign data. In an optional implementation, on the basis of at least one type of personalized human body physical sign data, the personalized variable human body parameter also comprises a personalized human body (i.e., the three-dimensional vertex information of a personalized human body) and the three-dimensional vertex information of various parts of the personalized human body.

The three-dimensional vertex information of various parts of the personalized human body comprises: the three-dimensional vertex information of various local parts, such as the head and neck, chest, upper limbs, lower limbs, pelvic perineum, abdomen, spine and the like, of the personalized human body, as well as the three-dimensional vertex information of various human body systems, such as the motor system, urinary system, respiratory system, visual system, oral system, circulatory system, blood system, immune system and the like, of the actual human body. The three-dimensional vertex information of the human body system of the personalized human body comprises the three-dimensional vertex information of human body tissues and/or human body organs of the actual human body. For example, the three-dimensional vertex information of the motor system comprises the three-dimensional vertex information of various tissues, such as bones, joints, muscles and the like.

Optionally, the step of converting the personalized variable human body model into a binary file comprises: creating a binary file; and writing a model name, the number of vertices and the three-dimensional positions of the vertices in the personalized variable human body model into the binary file layer by layer.

Optionally, the personalized variable human body model and its personalized human body parameter are converted into a binary format, and the model name, the number of vertices and the three-dimensional positions of vertices of the personalized variable human body model in the binary format are written into a binary file layer by layer. Compared with files in other formats, binary files occupy less storage space, support streaming parsing, and do not need extra transcoding.

Optionally, after converting the personalized variable human body model into a binary file and before outputting the binary file of the personalized variable human body model, further comprising: adding check bits and file size information into the binary file of the personalized variable human body model. The added check bits and file size information can timely detect an error or a tampered binary file in the process of subsequent binary file transmission, so as to improve reliability.

Optionally, in the embodiment of the present disclosure, there is provided another method 3000d for deploying and processing a variable human body model based on a typical variable human body model. As shown in FIG. 20B, the flowchart schematic view of the method comprises the following step S3304, in addition to steps S3301 to S3303:

S3304: Determining the key frame information of the personalized variable human body model according to the binary file of the personalized variable human body model; and generating and outputting the binary file of the key frame of the personalized variable human body model according to the key frame information of the personalized variable human body model.

Optionally, the personalized human body parameter is parsed from the binary file of the personalized variable human body model. Optionally, the name of the personalized variable human body model in a binary format, and the number of vertices and the position information of vertices in the personalized human body parameter in a binary format can be parsed layer by layer from the binary file of the personalized variable human body model. The data in the binary file is clearly and hierarchically arranged to ensure the reliability and efficiency of data interaction in combination with layer-by-layer input and layer-by-layer reading.

Optionally, the personalized human body parameter comprises personalized human body physical sign data, three-dimensional vertex information of a personalized human body, and three-dimensional vertex information of various parts of the personalized human body.

Optionally, the personalized human body physical sign data may comprise such data as gender, age, height, weight, chest circumference, waist circumference, hip circumference, arm circumference, leg circumference and the like of the personalized human body.

Optionally, the three-dimensional vertex information of various parts of the personalized human body may comprise: the three-dimensional vertex information of various local parts, such as the head and neck, chest, upper limbs, lower limbs, pelvic perineum, abdomen, spine and the like, of the personalized human body, as well as the three-dimensional vertex information of various human body systems, such as the motor system, urinary system, respiratory system, visual system, oral system, circulatory system, blood system, immune system and the like, of the personalized human body. The three-dimensional vertex information of the human body system of each personalized human body comprises the three-dimensional vertex information of human body tissues and human body organs of the personalized human body. For example, the three-dimensional vertex information of the motor system comprises the three-dimensional vertex information of various tissues, such as bones, joints, muscles and the like.

Optionally, in the embodiment of the present disclosure, the term "variable" in the variable human body model not only means that the three-dimensional vertex information in the human body parameter may vary based on personalized change, but also means that the three-dimensional shape of local parts, human body tissues and human body organs of the personalized human body may vary to simulate the real human body. For example, heart beat and lung respiratory morphology may vary. Therefore, the personalized variable human body model also comprises the three-dimensional vertex information of a plurality of key three-dimensional morphologies of the local parts, human body tissues and human body organs of the personalized human body in the personalized human body parameter. The three-dimensional vertex information of each key three-dimensional morphology varies nonlinearly in time dimension. Specifically, as each key three-dimensional morphology varies with time, the three-dimensional vertex information of the key three-dimensional morphology varies nonlinearly.

Optionally, a complete and displayable personalized variable human body model is determined according to the fixed information such as the vertex connection relationship, UV coordinates, and corresponding relationship between vertices of the variable human body model stored in advance, and the parsed personalized human body parameter.

The three-dimensional vertex information comprising various key three-dimensional morphologies is extracted from the complete and displayable personalized variable human body model. The three-dimensional vertex information comprising various key three-dimensional morphologies, and the fixed information such as the vertex connection relationship, UV coordinates, and corresponding relationship between vertices of the variable human body model as mentioned above are used as the key frame information of the personalized variable human body model. Each frame (including a key frame) of the personalized variable human body model may be regarded as a model image taken by a scene video camera at a certain time.

The binary file of the key frame of the personalized variable human body model is generated and outputted according to the key frame information of the personalized variable human body model.

In the embodiment of the present disclosure, the key frame can be used to not only express the three-dimensional morphological changes of local parts, human body tissues and human body organs of the human body, but also reduce the amount of data to be transmitted by eliminating non-key frames.

In an optional implementation, the step S3302 of processing a typical variable human body model in a variable human body model library according to the actual human body parameter to obtain a personalized variable human body model corresponding to the actual human body parameter comprises: interpolating the typical variable human body model in the variable human body model library according to the actual human body parameter to obtain a personalized variable human body model corresponding to the actual human body parameter.

In an optional implementation, the step of interpolating the typical variable human body model in the variable human body model library according to the actual human body parameter to obtain a personalized variable human body model corresponding to the actual human body parameter comprises:

determining a candidate variable human body model from the typical variable human body models in the variable human body model library according to the actual human body parameter; and interpolating the candidate variable human body model to obtain a personalized variable human body model.

Optionally, as shown in FIG. 21A, the step of determining a candidate variable human body model from the typical variable human body models in the variable human body model library according to the actual human body parameter comprises the steps S3411-S3412:

S3411: Determining the actual human body parameter class of the actual human body parameter.

Optionally, the actual human body parameter class comprises the data class of at least one type of human body physical sign data, and each data class has a mapping relationship with at least one typical human body parameter.

Optionally, the data class of the human body physical sign data may be determined in the following manner: setting a corresponding threshold and a corresponding data class for each type of human body physical sign data. In one example, the average value of this type of human body physical sign data in the actual humans may be used as a threshold, and two data classes can be divided. In other examples, the data class may be divided more finely. For example, the physical sign characteristic value of this type of human body physical sign data is used as a threshold, and a data class is located between the two adjacent physical sign characteristic values; or data classes may also be divided on the basis of a fixed data interval. For example, data classes such as 1-10 or 11-20 may be determined at the interval of 10.

In one example, if the physical sign characteristic values of height are respectively the maximum value of 200 cm, the minimum value of 140 cm, the average value of 170 cm, a value of 185 cm between the maximum value and the average value, and a value of 155 cm between the average value and the minimum value, the following data classes may be obtained: 140-155, 155-170, 170-185, 185-200, wherein the two typical human body parameters mapped by the class 140-155 are the typical human body parameter of height 140 cm and the typical human body parameter of height 155 cm respectively, that is, the typical human body parameters of the two endpoint values of this class, and the same is true for other classes.

Optionally, for the same type of human body physical sign data, different data classes may be set for different genders, so that the data classes may be set in line with gender characteristics.

Through the classes of the actual human body parameters (such as the data classes of various types of human body physical sign data), the actual human body parameters may be associated with the typical human body parameters, and furthermore, the actual human body parameters may be associated with the typical variable human body models. For example, the actual human body parameters may be associated with the typical variable human body models with different physical sign characteristics, different shape change characteristics or different body shapes, in order to determine a matching typical variable human body model as a candidate variable human body model according to the known actual human body parameter.

S3412: According to the mapping relationship between the actual human body parameter class and the typical human body parameter, determining the typical variable human body model of the typical human body parameter mapped by the actual human body parameter class as the candidate variable human body model.

Optionally, according to the mapping relationship between the data class of the human body physical sign data and the typical human body parameter, the typical variable human body model of the typical human body parameter mapped by each type of human body physical sign data in the actual human body parameter classes may be determined as the candidate variable human body model of the type of human body physical sign data.

In one example, if the typical variable human body model used is a typical variable human body model with different physical sign characteristics (e.g., the characteristics such as maximum height, minimum height, maximum weight or the like) or different shape change characteristics (e.g., the shape change characteristics reflected by the principal shape change components and shape change characteristic values determined based on principal component analysis), suppose that the height of the obtained actual human body parameters is 160 cm and the height class is 155-170, it can be determined that according to the mapping relationship between the height class and the typical human body parameter, the two typical human body parameters mapped by 155-170 are the typical human body parameters of 155 cm and 170 cm respectively. The typical variable human body models of the two typical human body parameters are used as two candidate variable human body models for height. Based on the similar method, when other human body physical sign data such as the user's weight, chest circumference, waist circumference and the like are obtained, two candidate variable human body models for each type of human body physical sign data, such as weight, chest circumference, waist circumference and the like, may be determined.

In another example, if the typical variable human body models used are typical variable human body models of different body types (such as standard body type, overweight body type and slim body type), suppose that for a typical variable human body model of a standard body type, the maximum value of a typical waist circumference is 80 cm, the minimum value thereof is 60 cm, the median thereof is 70 cm, and the mapped actual waist circumference class is 65-74 cm; and for a typical variable human body model of an overweight body type, the maximum value of a typical waist circumference is 90 cm, the minimum value thereof is 70 cm, the median thereof is 80 cm, and the mapped actual waist circumference class is 75-84 cm. When the actual waist circumference in the obtained actual human body parameter is 81 cm, it can be determined that the actual waist circumference falls within the actual waist circumference class of 75-84 cm, the mapped typical waist circumference is a typical waist circumference with a median of 80 cm, and the typical variable human body model to which the typical waist circumference belongs is a typical variable human body model of the overweight body type, which is used as a candidate variable human body model.

Through the above method, after obtaining the user's actual human body parameter, the typical variable human body model suitable for the user (such as the typical variable human body model of a certain shape change characteristic or the typical variable human body model of a certain body shape), that is, the candidate variable human body model, may be quickly determined according to the relationship between the actual human body parameter and the typical variable human body model established according to the actual human body parameter class (for example, various data classes in the actual human body parameter). The determined candidate variable human body model is used as the basis of a personalized customized model so as to improve the accuracy of personalized customization.

Optionally, as shown in FIG. 21A, the step of interpolating the candidate variable human body model to obtain a personalized variable human body model comprises the following steps S3413-S3414:

S3413: According to the mapping relationship between the actual human body parameter class and the typical human body parameter, determining the proportion coefficient between the actual human body parameter and the mapped typical human body parameter as a model weight coefficient.

Optionally, according to the mapping relationship between the data class of the human body physical sign data and the typical human body parameter, the proportion coefficient between each type of the human body physical sign data in the actual human body parameter and the type of the human body physical sign data in the mapped typical human body parameter is determined as the model weight coefficient of the candidate variable human body model of the type of the human body physical sign data. In each typical human body parameter, the number of each type of human body physical sign data may be one or more.

Optionally, in a solution, the step of according to the mapping relationship between the data class of the human body physical sign data and the typical human body parameter, determining the proportion coefficient between each type of the human body physical sign data in the actual human body parameter and the type of the human body physical sign data in the mapped typical human body parameter as the model weight coefficient of the candidate variable human body model of the type of the human body physical sign data comprises:

according to the mapping relationship between the data class of the human body physical sign data and the typical human body parameter, determining the difference between each type of the human body physical sign data and that in the first mapped typical human body parameter (at this time, the number of this type of the human body physical sign data is one) as the first physical sign difference; determining the difference between the type of human body physical sign data in the two typical human body parameters mapped by each type of the human body physical sign data as the typical physical sign difference; determining the proportion coefficient between the first physical sign difference and the typical physical sign difference as the model weight coefficient of one candidate variable human body model of the second typical human body parameter; and according to the model weight coefficient of one candidate variable human body model of the second typical human body parameter, determining the model weight coefficient of one candidate variable human body model of the first typical human body parameters.

In one example, if the typical variable human body model used is a typical variable human body model with different physical sign characteristics or different shape change characteristics, suppose a certain type of obtained human body physical sign data of the user is $h_0$, the data class is $h_1$-$h_2$ ($h_2$ is greater than $h_1$), and the two typical human body parameters mapped are the typical human body parameter of $h_1$ and the typical human body parameter of $h_2$ respectively. If the typical variable human body models of the two typical human body parameters are used as the two candidate variable human body models of the type of human body physical sign data, the model weight coefficients of the two candidate variable human body models may be determined in the following ways:

$$p = \frac{h_0 - h_1}{h_2 - h_1}$$

Equation (5)

54

-continued $$q = 1 - p = \frac{h_2 - h_0}{h_2 - h_1}$$

Equation (6)

In the equations (5) and (6), $h_0$-$h_1$ is the first physical sign difference, $h_2$-$h_1$ is the typical physical sign difference, p is the model weight coefficient of the candidate variable human body model corresponding to h2, and q is the model weight coefficient of the candidate variable human body model corresponding to h1.

The model weight coefficient of the candidate variable human body model of each type of human body physical sign data inputted by the user may be determined with reference to the equations (5) and (6).

For example, if the weight of the user is obtained as 50 kg and the weight class is 40-90 kg, the model weight coefficient of the candidate variable human body model corresponding to the weight of 40 kg is (90–50)/(90–40)=0.8, and the model weight coefficient of the candidate variable human body model corresponding to the weight of 90 kg is 1–0.8=0.2.

Optionally, in another solution, the step of according to the mapping relationship between the data class of the human body physical sign data and the typical human body parameter, determining the proportion coefficient between the type of the human body physical sign data in the actual human body parameter and the type of the human body physical sign data of the mapped typical human body parameter as the model weight coefficient of the candidate variable human body model of the type of the human body physical sign data comprises:

as for k types of the human body physical sign data, determining the model weight coefficient of the candidate variable human body model of each type of the human body physical sign data (at this time, the number of each type of the human body physical sign data is one) by the following manner:

$$\begin{bmatrix} a_{11} & \cdots & a_{1k} \\ \vdots & \ddots & \vdots \\ a_{k1} & \cdots & a_{kk} \end{bmatrix} \cdot \begin{bmatrix} g_1 \\ \vdots \\ g_k \end{bmatrix} = \begin{bmatrix} f_1 \\ \vdots \\ f_k \end{bmatrix}$$

Equation (7)

In the equation (7), $$A = \begin{bmatrix} a_{11} & \cdots & a_{1k} \\ \vdots & \ddots & \vdots \\ a_{k1} & \cdots & a_{kk} \end{bmatrix}$$

is a transformation matrix, $[g_1, \ldots, g_k]$ is the model weight coefficients of the k candidate variable human body models corresponding to the k types of the human body physical sign data (since the sum of two model weight coefficients is 1, the model weight coefficient of the other of the two candidate variable human body models corresponding to each type of human body physical sign data may be determined accordingly), $[f_1, \ldots, f_k]$ is the k types of the human body physical sign data in the obtained actual human body parameter of the user, wherein k is an integer larger than 0. As known by those skilled in the art, the transformation matrix A may also be a m×n matrix, wherein m and n are respectively an integer larger than 0.

The transformation matrix A may be determined in advance according to the typical human body parameters mapped by the k types of the human body physical sign data.

When the transformation matrix A is known, the model weight coefficient corresponding to each type of the human body physical sign data may be determined according to the obtained $[f_1, \ldots, f_k]$. The transformation matrix A may be determined in advance in any one of the following manners:

Manner 1: substituting the typical human body parameters mapped by the k types of the human body physical sign data into the transformation matrix A;

Manner 2: inputting a large number of sample data of the actual human body parameter and sample data of the model weight coefficient in the equation (7) to obtain the value of each element in the transformation matrix A by solving a linear equation group.

For Manner 1, suppose a candidate variable human body model corresponding to height is H=[170 cm, 70 kg, 90 cm, 65 cm, 95 cm], then H can be substituted into one element row, such as the first element row, of the transformation matrix A to obtain the first element row $a_{1j}$ as [170 cm, 70 kg, 90 cm, 65 cm, 95 cm]. Suppose a candidate variable human body model corresponding to weight is M=[160 cm, 60 kg, 85 cm, 60 cm, 90 cm], then M can be substituted into the second element row of the transformation matrix A to obtain the second row element $a_{2j}$ as [160 cm, 60 kg, 85 cm, 60 cm, 90 cm], and the data of chest circumference, waist circumference and hip circumference can be substituted by analogy.

Optionally, in another solution, the step of according to the mapping relationship between the data class of the human body physical sign data and the typical human body parameter, determining the proportion coefficient between each type of the human body physical sign data in the actual human body parameter and the type of the human body physical sign data in the mapped typical human body parameter as the model weight coefficient of the candidate variable human body model of the type of the human body physical sign data comprises:

according to the mapping relationship between the data class of the human body physical sign data and the typical human body parameter, determining the proportion coefficient between each type of the human body physical sign data in the actual human body parameter and the median of the type of the human body physical sign data (at this time, the number of type of the human body physical sign data is more than one) in the mapped typical human body parameter as the model weight coefficient of the candidate variable human body model of the type of the human body physical sign data.

In another example, if the typical variable human body model used is a typical variable human body model of different body types, the actual waist circumference in the actual human body parameter is 81 cm and the candidate variable human body model is a typical variable human body model of the overweight body type (reference can be made to the previous example for the determination of the candidate variable human body model), then the proportion coefficient between the actual waist circumference of 81 cm and the mapped typical waist circumference median of 80 cm (that is, the waist circumference median of the typical variable human body model of the overweight body type) can be determined as 1.0125 as the model weight coefficient.

S3414: According to the model weight coefficient, modifying the candidate variable human body model to obtain the personalized variable human body model.

Optionally, the candidate variable human body models of various types of human body physical sign data are modified according to the model weight coefficient of the candidate variable human body models of various types of human body physical sign data to obtain the personalized variable human body models based on various types of human body physical sign data.

Optionally, if the typical variable human body model used is the typical variable human body models of different physical sign characteristics or different shape change characteristics, as for the obtained k types of the human body physical sign data of the user, after determining the candidate variable human body models of the k types of the human body physical sign data and the model weight coefficients thereof, the personalized variable human body model may be obtained by the following manner:

$$X_0 = \sum_1^k (p_i X_i + q_i Y_i) \qquad \text{Equation (8)}$$

In the equation (8), $X_0$ is a personalized viable human body model, $X_i$ and $Y_i$ are respectively two candidate variable human body models determined on the basis of the i-th type of human body physical sign data, and $p_i$ and $q_i$ are respectively the model weight coefficients of the candidate variable human body models $X_i$ and $Y_i$, reference can be made to the previous equation (5) for the calculation of $p_i$, and reference can be made to the previous equation (6) for the calculation of $q_i$.

In the equation (8), the weighted calculation of the candidate variable human body models Xi and Yi is essentially the weighted calculation of the coordinates of each three-dimensional vertex in the candidate variable human body models Xi and Yi.

In another example, if the typical variable human body models used are typical variable human body models of different body types, and the candidate variable human body model is the typical variable human body model of the overweight body type, after the model weight coefficient (such as 1.0125 determined in the previous example) is determined based on a certain type of human body physical sign data (such as waist circumference), the weighted calculation of other human body physical sign data in the typical variable human body model of the overweight body shape may be done according to the model weight coefficient (that is, other human body physical sign data are multiplied by the model weight coefficient), and the weighted calculation of the three-dimensional sizes of each human body physical sign data, each part, each system, each tissue and each organ are done to obtain the personalized variable human body model and the corresponding personalized human body parameter.

In another optional implementation, the step of interpolating the typical variable human body model in the variable human body model library according to the actual human body parameter to obtain a personalized variable human body model corresponding to the actual human body parameter specifically comprises: according to the priority order of at least two types of human body physical sign data in the actual human body parameter, performing the following steps S3421-S3424 with reference to FIG. 21B:

S3421: For the first type of human body physical sign data, determining the candidate variable human body model of the first type of human body physical sign data from the typical variable human body models in the variable human body model library.

Optionally, for the first type of human body physical sign data, according to the mapping relationship between the data class of human body physical sign data and the typical human body parameter, the respective typical variable human body models of the two typical human body parameters mapped by the first type of human body physical sign data are determined as the two candidate variable human body models of this type of human body physical sign data.

The priority order of human body physical sign data can be set according to the actual situations, for example, according to the degree of influence of human body physical sign data on body characteristics. For example, the human body physical sign data affecting the whole body characteristics (such as height or physical sign) enjoys higher priority, and the human body physical sign data affecting the local characteristics (such as chest circumference, waist circumference and hip circumference) enjoys lower priority.

By setting the priority and performing interpolation steps sequentially according to the priority order, the order of interpolation may be optimized to improve the accuracy of the overall calculation. For example, for the human body physical sign data having different degrees of influence on the body characteristics, if the interpolation is first done based on the human body physical sign data affecting the local characteristics, the influence of the human body physical sign data affecting the local characteristics will inevitably affect the later interpolation based on the human body physical sign data affecting the whole body characteristics. The influence of the human body physical sign data affecting the local characteristics may be magnified, resulting in a large error. If, according to the degrees of influence on the body characteristics, the human body physical sign data affecting the whole body characteristics is interpolated, and then the human body physical sign data affecting the local characteristics is interpolated, the above error may be effectively reduced or eliminated.

For various types of human body physical sign data set according to a priority order, the "first type of human body physical sign data" in the embodiment of the present disclosure is the type of human body physical sign data having the highest priority.

S3422: Interpolating the candidate variable human body model of the first type of human body physical sign data to obtain the personalized variable human body model corresponding to the first type of human body physical sign data.

Optionally, according to the mapping relationship between the human body physical sign data and the typical human body parameter, the proportion coefficient between the type of the human body physical sign data in the actual human body parameter and the type of the human body physical sign data of the two candidate variable human body models is determined as the model weight coefficients of the two candidate variable human body models of the type of human body physical sign data; and according to the model weight coefficients of the two candidate variable human body models of the type of human body physical sign data, the two candidate variable human body models of the type of human body physical sign data are interpolated to obtain the personalized variable human body model corresponding to the type of human body physical sign data.

S3423: For each type of human body physical sign data after the first type of human body physical sign data, according to the typical variable human body model in the variable human body model library and the personalized variable human body model corresponding to the previous type of human body physical sign data, determining the candidate variable human body model of the type of the human body physical sign data.

Optionally, for each type of human body physical sign data after the first type of human body physical sign data, according to the mapping relationship between the data class of human body physical sign data and typical human body parameter, the typical variable human body model of a typical human body parameter mapped by the type of human body physical sign data is determined, and the typical variable human body model corresponding to the type of human body physical sign data and the personalized variable human body model corresponding to the previous type of human body physical sign data are taken as two candidate variable human body models of the type of human body physical sign data.

S3424: Determining the candidate variable human body model of the type of the human body physical sign data and interpolating the candidate variable human body model of the type of the human body physical sign data to obtain the personalized variable human body model corresponding to the type of the human body physical sign data.

Optionally, according to the mapping relationship between the human body physical sign data and the typical human body parameters, the proportion coefficient between the type of human body physical sign data in the actual human body parameter and the type of human body physical sign data of the two candidate variable human body models is determined as the model weight coefficients of the two candidate variable human body models of the type of human body physical sign data; and according to the model weight coefficients of the two candidate variable human body models of the type of human body physical sign data, the two candidate variable human body models of the type of human body physical sign data are interpolated to obtain the personalized variable human body model corresponding to the type of human body physical sign data.

For various types of human body physical sign data set according to a priority order, in the embodiment of the present disclosure, "each type of human body physical sign data after the first type of human body physical sign data" is the second to the n-th type of human body physical sign data whose priority is after that of the first type of human body physical sign data, wherein the priority of the second type of human body physical sign data is second only to that of the first type of human body physical sign data, the priority of the third type of human body physical sign data is second only to that of the second type of human body physical sign data, and so on. "Previous type of human body physical sign data" in the embodiment of the present disclosure refers to a type of human body physical sign data whose priority is before and adjacent to that of the current type of human body physical sign data (that is, the type of human body physical sign data currently processed).

Optionally, the personalized variable human body model corresponding to the actual human body parameter comprises: the personalized variable human body model corresponding to each type of human body physical sign data, or the personalized variable human body model corresponding to the last type of human body physical sign data. That is, after completing the construction of the personalized variable human body model corresponding to each type of human body physical sign data according to the priority order of at least two types of human body physical sign data in the actual human body parameter, the personalized variable human body models obtained can be jointly used as the personalized variable human body model corresponding to the actual human body parameter, or the personalized variable human body model that is last constructed (that is, the personalized variable human body model corresponding to the last type of human body physical sign data) can also be used as the personalized variable human body model of the actual human body parameter.

Optionally, in the above implementation with a priority order, for each type of human body physical sign data in the actual human body parameter, reference can be made to the equation (8) to modify the two candidate variable human body models of the type of human body physical sign data according to the model weight coefficients of the two candidate variable human body models of the type of human body physical sign data.

Optionally, in the above implementation with a priority order, the step of determining the model weight coefficients of the two candidate variable human body models of each type of human body physical sign data comprises:

according to the mapping relationship between the data class of the human body physical sign data and the typical human body parameter, determining the difference between the type of the human body physical sign data and that in the first mapped typical human body parameter as the first physical sign difference; determining the difference between the human body physical sign data in the two typical human body parameters mapped by the type of the human body physical sign data as the typical physical sign difference; determining the proportion coefficient between the first physical sign difference and the typical physical sign difference as the model weight coefficient of one candidate variable human body model of the second typical human body parameter; and according to the model weight coefficient of one candidate variable human body model of the second type of the typical human body parameter, determining the model weight coefficient of one candidate variable human body model of the first typical human body parameter.

Reference can be made to the examples of the equations (5) and (6).

Optionally, in the above implementation mode with a priority order, reference may also be made to the principle of the equation (7) for determining the model weight coefficients of the two candidate variable human body models of each type of human body physical sign data. According to the priority order of various types of human body physical sign data $f_1$ to $f_k$, the elements in each row of the transformation matrix A may be determined sequentially, and further the model weigh coefficients $g_1$ to $g_k$ may be determined sequentially. For each type of human body physical sign data, the manner to determine the transformation matrix A in the equation (7) may be any one of the above-mentioned manner 2 and the following manner 3:

Manner 3: Substituting each of the differences obtained by subtracting the human body physical sign data of the two typical human body parameters mapped by each type of the human body physical sign data into the transformation matrix A.

In a specific example, if the actual human body parameter comprises five types of human body physical sign data (height, weight, chest circumference, waist circumference and hip circumference) which are in the order of descending priority, when the model weight coefficient is calculated based on height with the highest priority, k in the transformation matrix A is 1, that is, the transformation matrix A is transformed into a single data $a_{11}$, which can be determined in the following manner:

suppose that the typical human body parameter of the two candidate variable human body models corresponding to height also comprises the five types of human body physical sign data, for example, I=[150 cm, 60 kg, 85 cm, 60 cm, 90 cm] and H=[170 cm, 70 kg, 90 cm, 65 cm, 95 cm], the height data (170 cm) in H and the height data (150 cm) in I are subtracted to obtain the data 20 cm, which is then substituted into all.

In this example, when the model weight coefficient is calculated based on weight with the second priority, k in the transformation matrix A is 2, that is, the transformation matrix A is a two-dimensional matrix, which may be determined by the following manner:

suppose that the typical human body parameter of the two candidate variable human body models corresponding to height and that of the two candidate variable human body models corresponding to weight both comprise the five types of human body physical sign data, for example, the two candidate variable human body models corresponding to height are I and H as mentioned above, and the two candidate variable human body models corresponding to weight are M=[160 cm, 60 kg, 85 cm, 60 cm, 90 cm] and N=[160 cm, 100 kg, 85 cm, 70 cm, 85 cm]; the height data (170 cm), weight data (70 kg) in H and the height data (150 cm) and weight data (60 kg) in I are subtracted correspondingly, and the height difference (20 cm) and weight difference (10 kg) obtained are respectively substituted into the first row elements $a_{11}$ and $a_{12}$ in the two-dimensional matrix; and the height data (160 cm), weight data (100 kg) in N and the height data (160 cm) and weight data (60 kg) in M are subtracted correspondingly, and the height difference (0 cm) and weight difference (40 kg) obtained are respectively substituted into the second row elements $a_{21}$ and $a_{22}$ in the two-dimensional matrix A.

Based on this example, when the model weight coefficient is calculated based on the chest circumference, waist circumference and hip circumference with lower priority and other human body physical sign data, the method for determining the transformation matrix A is analogized according to the priority order. For the human body physical sign data with the k-th priority, the transformation matrix A is a k-dimensional matrix, the k types of human body physical sign data of the candidate variable human body models corresponding to the 1-th to k-th human body physical sign data are subtracted respectively, and the corresponding differences are substituted into the transformation matrix A.

The principle of the above interpolation calculation will be introduced by taking for example the four human body physical sign data of height, weight, chest circumference and waist circumference which are in the order of descending priority.

First, the gender of the user is decided according to the actual human body parameter so as to determine from which folder the typical variable human body model to be interpolated is called; if the gender is male, then the typical variable human body model in the folder corresponding to male is then called, and if the gender is female, then the typical variable human body model in the folder corresponding to female is then called.

According to the priority order, the candidate variable human body model of height (hereinafter referred to as target height) and its model weight coefficient in the actual human body parameter are determined according to the mapping relationship between height class and typical human body parameter, wherein the two candidate variable human body models are respectively typical variable human body models corresponding to the end values of the class to which they belong. The candidate variable human body models are modified with reference to the equation (8) to obtain the personalized variable human body model of target height.

According to the mapping relationship between the weight class and the typical human body parameter, a candidate variable human body model (which may be a typical variable human body model corresponding to any end point value of the class to which it belongs) of weight (hereinafter referred to as the target weight) in the actual human body parameter and its model weight coefficient are determined, the personalized variable human body model of target height is used as another candidate variable human body model and the model weight coefficient thereof is determined. The candidate variable human body models are modified with reference to the equation (8) to obtain the personalized variable human body model of the target weight.

According to the mapping relationship between the chest circumference class and the typical human body parameter, a candidate variable human body model (which may be a typical variable human body model corresponding to any end point value of the class to which it belongs) of chest circumference (hereinafter referred to as the target chest circumference) in the actual human body parameter and its model weight coefficient are determined, the personalized variable human body model of target weight is used as another candidate variable human body model and the model weight coefficient thereof is determined. The candidate variable human body models are modified with reference to the equation (8) to obtain the personalized variable human body model of the target chest circumference.

According to the mapping relationship between the waist circumference class and the typical human body parameter, a candidate variable human body model (which may be a typical variable human body model corresponding to any end point value of the class to which it belongs) of waist circumference (hereinafter referred to as the target waist circumference) in the actual human body parameter and its model weight coefficient are determined, the personalized variable human body model of target weight is used as another candidate variable human body model and the model weight coefficient thereof is determined. The candidate variable human body models are modified with reference to the equation (8) to obtain the personalized variable human body model of the target waist circumference. The personalized variable human body model of the target waist circumference may be used as the personalized variable human body model corresponding to the actual human body parameter inputted by the user, i.e., a model reflecting the body characteristics of a target user.

The personalized variable human body model obtained based on the interpolation of the priority order of the human body physical sign data and in consideration of the complexity of the human body physical sign data of actual humans is more accurate and more matchable with the user.

In another optional implementation of the step S3302, the step of processing the typical variable human body model in the variable human body model library according to the actual human body parameter to obtain the personalized variable human body model corresponding to the actual human body parameter comprises:

processing the typical variable human body model associated with a human body parameter according to the actual human body parameter to obtain the personalized variable human body model corresponding to the actual human body parameter.

The association between the human body parameter and the typical variable human body model is determined in advance by the following manner:

constructing a plurality of user's actual human body models according to the plurality of user's actual human body parameters; and determining the relationship between the human body parameter and the variable human body model according to the corresponding relationships between the plurality of user's actual human body parameters and the plurality of corresponding actual human body models.

In an example, the association between the human body parameter and the typical variable human body model may be expressed as follows:

$$M[f_1, f_2, \ldots, f_k, 1]^T = b \qquad \text{Equation (9)}$$

In the equation (9), $[f_1, f_2, \ldots, f_k]$ refers to the k types of human body physical sign data in the human body parameter, $b = [b_1, b_2, \ldots, b_c]$ is the shape coefficient in the above-mentioned equation (4), and M is the transformation matrix.

As for the method for determining the transformation matrix M, reference can be made to the Manner 2 described above for determining the transformation matrix A: inputting a large number of sample data of the actual human body parameter and sample data of the shape coefficient to obtain the value of each element in the transformation matrix M by solving a linear equation group; and after determining the transformation matrix M, determining the association relationship between the human body parameter $[f_1, f_2, \ldots, f_k]$ and the shape coefficient vector b, and then determining the association relationship between the human body parameter $[f_1, f_2, \ldots, f_k]$ and the typical variable human body model X in combination with the above-mentioned equation (4).

When the above-mentioned association relationship has been determined, the user's actual human body parameter is substituted into the equation (9) to determine the shape coefficient vector b. The shape coefficients in the shape coefficient vector b are substituted into the equation (4) to modify the typical variable human body model and obtain the personalized variable human body model corresponding to the actual human body parameter.

It can be seen that in the non-limiting embodiment of the present disclosure, the personalized variable human body model is obtained by selecting the typical variable human body model that best matches the actual human body parameter and making weighted modification to the selected typical variable human body model. Compared with the conventional method for calculating and obtaining the personalized variable human body model by using the conventional statistical method, it can avoid a large amount of tedious statistical calculation, greatly save the amount of calculation, reduce the cost and improve the efficiency while ensuring high precision and high fidelity of the personalized variable human body model.

Optionally, in the exemplary embodiment of the present disclosure, there is provided a further method 3000e for deploying and processing a variable human body model based on a typical variable human body model. As shown in FIG. 20C, the flowchart schematic view of the method comprises the following steps S3305 and S3306, in addition to steps S3301 to S3304:

S3305: Reading out the key frame information of the personalized variable human body model from the binary file of the key frame of the personalized variable human body model.

Optionally, the key frame information of the personalized variable human body model in a binary format is read out from the binary file of the key frame of the personalized variable human body model. The key frame information comprises the three-dimensional vertex information of a plurality of key three-dimensional morphologies of the local parts, human body tissues and human body organs of the personalized human body in the personalized human body parameter.

Optionally, the key frame information of the personalized variable human body model corresponding to the type of the human body physical sign data is read out from the binary file of the key frame of the personalized variable human body model (reference can be made to the contents related to the steps S3421 to S3424 for the method for obtaining the model) corresponding to each type of the human body physical sign data.

S3306: Performing a tween operation according to the key frame information of the personalized variable human body model to obtain and play the animation of the personalized variable human body model.

Optionally, at least one transition frame between any two adjacent key frames is determined by using the tween operation according to the key frame information of the two adjacent key frames in the personalized variable human body model; and the animation of the personalized variable human body model is generated and played according to the key frames and transition frames of the personalized variable human body model.

In the embodiment of the present disclosure, key frames are used to express the changes of the three-dimensional morphologies of the human body local parts, human body tissues and human body organs, and the amount of data to be transmitted can be reduced by eliminating non-key frames.

Optionally, a tween operation is performed according to the key frame information of the personalized variable human body model corresponding to each type of human body physical sign data to obtain the animation of the personalized variable human body model corresponding to the type of human body physical sign data; and the animations of the personalized variable human body models corresponding to various types of human body physical sign data are played sequentially according to the priority order of various types of human body physical sign data.

The animations of the personalized variable human body models corresponding to various types of human body physical sign data sequentially obtained by interpolation according to the priority order are played sequentially according to the priority order of various types of human body physical sign data so as to continuously display the personalized variable human body models and enable users to visually observe the influence of various types of human body physical sign data on the three-dimensional model.

Optionally, as shown in FIG. 22, the method for processing a variable human body model provided by the exemplary embodiment of the present disclosure further comprises the steps S3501 to S3504:

S3501: Determining the key frame information of the candidate variable human body model according to the binary file of the candidate variable human body model; and generating and outputting the binary file of the key frame of the candidate variable human body model according to the key frame information of the candidate variable human body model.

Optionally, the typical human body parameter of the candidate variable human body model is parsed from the binary file of the candidate variable human body model. Optionally, the name of the candidate variable human body model in a binary format, and the number of vertices and the position information of vertices in the typical human body parameter in a binary format can be parsed layer by layer from the binary file of the candidate variable human body model.

Optionally, a complete and displayable candidate variable human body model is determined according to the fixed information such as the vertex connection relationship, UV coordinates, and corresponding relationship between vertices of the variable human body model stored in advance, and the parsed typical human body parameter.

The three-dimensional vertex information comprising various key three-dimensional morphologies is extracted from the complete and displayable candidate variable human body model. The three-dimensional vertex information comprising various key three-dimensional morphologies, and the fixed information such as the vertex connection relationship, UV coordinates, and corresponding relationship between vertices of the variable human body model are used as the key frame information of the candidate variable human body model.

The binary file of the key frame of the candidate variable human body model is generated and outputted according to the key frame information of the candidate variable human body model.

S3502: Reading out the key frame information of the candidate variable human body model from the binary file of the key frame of the candidate variable human body model.

Optionally, the key frame information of the candidate variable human body model in a binary format is read out from the binary file of the key frame of the candidate variable human body model. The key frame information comprises three-dimensional vertex information of a plurality of key three-dimensional morphologies of the local parts, human body tissues and human body organs of the typical human body in the typical human body parameter of the candidate variable human body model.

S3503: Performing a tween operation according to the key frame information of the candidate variable human body model to obtain and play the animation of the candidate variable human body model.

The animation of the candidate variable human body model is generated and played according to the key frames and transition frames of the candidate variable human body model.

The exemplary embodiment of the present disclosure may play the candidate variable human body model in the form of animation, so that the user may visually observe the situation of each candidate variable human body model determined on the basis of his or her own actual human body parameters. When the personalized variable human body model is subsequently generated on the basis of the candidate variable human body model and played in the form of animation, the user can visually observe the change process from the candidate variable human body model to the personalized variable human body model, and visually understand the differences between his or her own personalized variable human body model and the candidate variable human body model based on the real humans.

Based on the same inventive concept, the exemplary embodiment of the present disclosure provides a processing device of a variable human body model, which is used to implement the human body model generation method provided by the exemplary embodiment of the present disclosure.

As shown in FIG. 23A, the processing device provided by the embodiment of the present disclosure comprises: a parameter acquisition module 601 and a model personalized module 602.

The parameter acquisition module 601 is configured to acquire the actual human body parameter of the user.

The model personalized module 602 is configured to process the typical variable human body model in the variable human body model library according to the actual human body parameter to obtain the personalized variable human body model corresponding to the actual human body parameter.

Optionally, the model personalized module 602 is specifically configured to: determine the gender of the user according to the actual human body parameter; and process the typical variable human body model of the gender in the variable human body model library to obtain the personalized variable human body model corresponding to the actual human body parameter.

Optionally, the model personalized module 602 is specifically configured to interpolate the typical variable human body model in the variable human body model library according to the actual human body parameter to obtain the personalized variable human body model corresponding to the actual human body parameter.

Optionally, the model personalized module 602 is specifically configured to: determine a candidate variable human body model from the typical variable human body models in the variable human body model library according to the actual human body parameter; and interpolate the candidate variable human body model to obtain the personalized variable human body model.

Optionally, when determining the candidate variable human body model, the model personalized module 602 is specifically configured to: determine the actual human body parameter class of the actual human body parameter; and according to the mapping relationship between the actual human body parameter class and the typical human body parameter, determine the typical variable human body model of the typical human body parameter mapped by the actual human body parameter class as the candidate variable human body model.

Optionally, when determining the candidate variable human body model, the model personalized module 602 is specifically configured to: according to the mapping relationship between the data class of the human body physical sign data and the typical human body parameter, determine the typical variable human body model of the typical human body parameter mapped by each type of human body physical sign data in the actual human body parameter class as a candidate variable human body model of the type of the human body physical sign data.

Optionally, during interpolation, the model personalized module 602 is specifically configured to: according to the mapping relationship, determine the proportion coefficient between the actual human body parameter and the mapped typical human body parameter as a model weight coefficient; and according to the model weight coefficient, modify the candidate variable human body model to obtain the personalized variable human body model.

Optionally, during interpolation, the model personalized module 602 is specifically configured to: according to the model weight coefficients of the candidate variable human body models of various types of the human body physical sign data, modify the candidate variable human body model of various types of the human body physical sign data (such as the modifying manner indicated by the equation (8)) to obtain the personalized variable human body model based on various types of the human body physical sign data.

Optionally, when determining the model weight coefficient, the model personalized module 602 is specifically configured to: according to the mapping relationship between the data class of the human body physical sign data and the typical human body parameter, determine the proportion coefficient between each type of the human body physical sign data in the actual human body parameter and the type of the human body physical sign data in the mapped typical human body parameter as the model weight coefficient of the candidate variable human body model of the type of the human body physical sign data.

In an optional implementation, when determining the model weight coefficient, the model personalized module 602 is specifically configured to: according to the mapping relationship between the data class of the human body physical sign data and the typical human body parameter, determine the proportion coefficient between each type of the human body physical sign data in the actual human body parameter and the median of the type of the human body physical sign data in the mapped typical human body parameter as the model weight coefficient of the candidate variable human body model of the type of the human body physical sign data.

In another optional implementation, when determining the model weight coefficient, the model personalized module 602 is specifically configured to: according to the mapping relationship between the data class of the human body physical sign data and the typical human body parameter, determine the difference between the type of the human body physical sign data and that in the first mapped typical human body parameter as the first physical sign difference; determine the difference between the human body physical sign data in the two typical human body parameters mapped by the type of the human body physical sign data as the typical physical sign difference; determine the proportion coefficient between the first physical sign difference and the typical physical sign difference as the model weight coefficient of one candidate variable human body model of the second typical human body parameter; and according to the model weight coefficient of one candidate variable human body model of the second typical human body parameter, determine the model weight coefficient of one candidate variable human body model of the first typical human body parameters.

In a further optional implementation, when determining the model weight coefficient, the model personalized module 602 is specifically configured to: determine the model weight coefficient by the manner indicated by the equation (7).

Optionally, the model personalized module 602 is specifically configured to: according to the priority order of at least two types of human body physical sign data in the actual human body parameter, for the first type of human body physical sign data, determine the candidate variable human body model of the first type of human body physical sign data from the typical variable human body model in the variable human body model library, and interpolate the candidate variable human body model of the first type of human body physical sign data to obtain the personalized variable human body model corresponding to the first type of human body physical sign data; and for each type of human body physical sign data after the first type of human body physical sign data, according to the typical variable human body model in the variable human body model library and the personalized variable human body model corresponding to the previous type of human body physical sign data, determine the candidate variable human body model of the type of the human body physical sign data, and interpolate the candidate variable human body model of the type of the human body physical sign data to obtain the personalized variable human body model corresponding to the type of the human body physical sign data.

Optionally, for the first type of human body physical sign data, the model personalized module 602 is specifically configured to: according to the mapping relationship between the data class of the human body physical sign data and the typical human body parameter, determine the respective typical variable human body models of the two typical human body parameters mapped by the human body physical sign data as the two candidate variable human body models of the type of the human body physical sign data; according to the mapping relationship between the human body physical sign data and the typical human body parameter, determine the proportion coefficients between the type of the human body physical sign data in the actual human body parameter and the type of the human body physical sign data of the two candidate variable human body models as the model weight coefficients of the two candidate variable human body models of the type of the human body physical sign data; and according to the model weight coefficients of the two candidate variable human body models of the type of the human body physical sign data, interpolate the two candidate variable human body models of the type of the human body physical sign data to obtain the personalized variable human body model corresponding to the type of the human body physical sign data.

Optionally, for each type of human body physical sign data after the first type of human body physical sign data, the model personalized module 602 is specifically configured to: according to the mapping relationship between the data class of the human body physical sign data and the typical human body parameter, determine the typical variable human body model of one typical human body parameter mapped by the type of the human body physical sign data, and regarding the typical variable human body model corresponding to the type of the human body physical sign data and the personalized variable human body model corresponding to the previous type of the human body physical sign data as the two candidate variable human body models of the type of the human body physical sign data; according to the mapping relationship between the human body physical sign data and the typical human body parameter, determine the proportion coefficients between the type of the human body physical sign data in the actual human body parameter and the type of the human body physical sign data of the two candidate variable human body models as the model weight coefficients of the two candidate variable human body models of the type of the human body physical sign data; and according to the model weight coefficients of the two candidate variable human body models of the type of the human body physical sign data, interpolate the two candidate variable human body models of the type of the human body physical sign data to obtain the personalized variable human body model corresponding to the type of the human body physical sign data.

Optionally, the exemplary embodiment of the present disclosure provides another processing device of a variable human body model, the structural architecture of which is shown in FIG. 23B. In addition to the parameter acquisition module 601 and the model personalized module 602, the processing device further comprises a module generation module 603.

In an optional implementation, the model generation module 603 is configured to: construct a plurality of actual human body models according to the plurality of sample human body parameters; determine a principal shape change component of each of the actual human body models and a shape change characteristic value corresponding to the principal shape change component according to a principal component analysis method; and determine the typical variable human body model according to the principal shape change component and the shape change characteristic value.

In an optional implementation, the model generation module 603 is configured to: extract a typical human body parameter from variable model original data; and generate the typical variable human body model according to the typical human body parameter.

Optionally, the model generation module 603 is specifically configured to: determine at least one physical sign characteristic value of each type of the human body physical sign data according to the human body physical sign data in the plurality of sample human body parameters; and determine one typical human body parameter according to each of the physical sign characteristic values.

Optionally, the model generation module 603 is specifically configured to: construct a plurality of actual human body models according to the plurality of sample human body parameters; detect the change information of each type of the human body physical sign data in each of the actual human body models; and determine at least one physical sign characteristic value of each type of the human body physical sign data according to the change information.

Optionally, the model generation module 603 is specifically configured to: generate one actual human body model according to each sample human body parameter to obtain the plurality of actual human body models; and normalize the plurality of actual human body models to make the positions and angles of the plurality of actual human body models consistent in the same three-dimensional space.

Optionally, the model generation module 603 is specifically configured to: select any one of the actual human body models as an initial model; move and rotate the rest of the actual human body models in the same three-dimensional space sequentially until the position and angle of the moved and rotated actual human body model in the three-dimensional space are consistent with the position and angle of the initial model in the three-dimensional space.

Optionally, the model generation module 603 is further configured to: convert the file of the typical variable human body model into a binary file for storage after generating the typical variable human body model according to the typical human body parameter, wherein the binary file of the typical variable human body model comprises a typical human body parameter in a binary format.

Optionally, the model personalized module 602 is further configured to: convert the file of the personalized variable human body model into a binary file and outputting the same, wherein the binary file of the personalized variable human body model comprises a personalized variable human body parameter in a binary format.

Optionally, the model personalized module 602 is further configured to: create a binary file; and write a model name, the number of vertices and the three-dimensional positions of the vertices in the personalized variable human body model into the binary file layer by layer.

Optionally, the model personalized module 602 is further configured to: after converting the personalized variable human body model into a binary file and before outputting the binary file of the personalized variable human body model, add check bits and file size information into the binary file of the personalized variable human body model.

Optionally, as shown in FIG. 23B, another processing device of a variable human body model provided by the exemplary embodiment of the present disclosure further comprises: a key frame determination module 604.

The key frame determination module 604 is configured to: determine the key frame information of the personalized variable human body model according to the binary file of the personalized variable human body model; and generate and output the binary file of the key frame of the personalized variable human body model according to the key frame information of the personalized variable human body model.

Optionally, the key frame determination module 604 is further configured to: determine the key frame information of the candidate variable human body model according to the binary file of the candidate variable human body model; and generate and output the binary file of the key frame of the candidate variable human body model according to the key frame information of the candidate variable human body model.

Optionally, the model personalized module 602 is specifically configured to store a binary file by means of a Unity script.

Optionally, as shown in FIG. 23B, another processing device of a variable human body model provided by the exemplary embodiment of the present disclosure further comprises: an animation generation module 605.

The animation generation module 605 is configured to: read out the key frame information of the personalized variable human body model from the binary file of the key frame of the personalized variable human body model; and perform a tween operation according to the key frame information of the personalized variable human body model to obtain and play the animation of the personalized variable human body model.

Optionally, the animation generation module 605 is further configured to: read out the key frame information of the candidate variable human body model from the binary file of the key frame of the candidate variable human body model; and perform a tween operation according to the key frame information of the candidate variable human body model to obtain and play the animation of the candidate variable human body model.

Optionally, the personalized variable human body model corresponding to the actual human body parameter comprises a personalized variable human body model corresponding to each type of the human body physical sign data in the actual human body parameter, and the animation generation module 605 is specifically configured to: read out the key frame information of the personalized variable human body model corresponding to each type of the human body physical sign data from the binary file of the key frame of the personalized variable human body model corresponding to the type of the human body physical sign data; and perform a tween operation according to the key frame information of the personalized variable human body model corresponding to each type of the human body physical sign data to obtain the animation of the personalized variable human body model corresponding to the type of the human body physical sign data; and sequentially play the animation of the personalized variable human body models corresponding to various types of the human body physical sign data according to the priority order of various types of the human body physical sign data.

Another processing device of a variable human body model of the present embodiment may implement any generation method of a variable human body model provided by the embodiment of the present disclosure, and its implementation principle is similar, which will not be reiterated herein.

Based on the same inventive concept, the embodiment of the present disclosure provides a processing system of a variable human body model, the architecture of which is schematically shown in FIG. 24. It comprises an input unit, a processor and a display unit.

The input unit is configured to receive an actual human body parameter of a user.

The processor is electrically coupled to the input unit to generate a personalized variable human body model corresponding to the actual human body parameter according to any processing method of a variable human body in the present disclosure.

The display unit is electrically coupled to the processor to display the personalized variable human body model.

Optionally, the processing system of the variable human body model in the embodiment of the present disclosure is specifically a separate terminal device, which may be an electronic device with strong computing power such as a desktop computer, a notebook computer or a two-in-one computer.

Optionally, the processing system of the variable human body model in the embodiment of the present disclosure comprises a cloud device and a terminal device connected or coupled by communication. The cloud device may be an electronic device with strong computing power, such as a single server, a server cluster or a distributed server, and has a processor for performing the steps S3101 and S3102 in the processing method of the variable human body model, various methods for obtaining the typical variable human body model, and the steps S3301-S3304 in the method for deploying and processing a variable human body model based on a typical variable human body model, as above mentioned. The terminal device may be an electronic device with weak computing power, such as a smart phone or a tablet computer, and has an input unit, a processor and a display unit for performing the steps S3305 and S3306 in the method for deploying and processing a variable human body model based on a typical variable human body model.

Optionally, the deployment architecture of a processing system of a variable human body model according to the embodiment of the present disclosure, the schematic view of which is shown in FIG. 25, comprises the terminal device 810 and the cloud device 820. The terminal device 810 shown in FIG. 25 comprises: a processor 811 and a memory 813, wherein the processor 811 is electrically coupled to the memory 813 through, e.g., a bus 812. Optionally, the structure of the terminal device 810 does not constitute a limitation to an embodiment of the present disclosure.

The processor 811 may be a CPU, general purpose processor, DSP, ASIC, FPGA or other programmable logic device, transistor logic device, hardware component or any combination thereof. It may implement or execute various exemplary logical blocks, modules and circuits described in connection with the contents of the present disclosure. The processor 811 may also be a combination for realizing computing functions, for example, comprising a combination of one or more microprocessors or a combination of DSP and microprocessors.

The bus 812 may comprise a pathway for transmitting information between the above-mentioned assemblies. The bus 812 may be a PCI bus or an EISA bus or the like. The bus 812 may be divided into an address bus, a data bus, a control bus, etc. For easy expression, only one thick line is used in FIG. 25, but it does not mean that there is only one bus or one type of buses.

The memory 813 may be a ROM or other types of static storage devices that can store static information and instructions, a RAM or other types of dynamic storage devices that can store information and instructions, or may be an EEPROM, a CD-ROM or other optical disk storage, optical disc storage (including a compact disc, a laser disc, an optical disc, a digital versatile optical disc, a blue-ray disc, etc.), magnetic disk storage medium or other magnetic storage devices, or any other medium that can be used to carry or store desired program code in the form of instructions or data structures and can be accessed by a computer. But the memory is not limited to these.

The input unit 814 may be used to receive inputted digital or character information and generate key signal inputs related to user settings and function control of the terminal device. Specifically, the input unit 504 may comprise a touch panel and other input devices. The touch panel, also known as the touch screen, may collect the user's touch operations on or near the touch panel (such as the user's operation on or near the touch panel with any suitable object or accessory such as a finger or a stylus), and drive a corresponding connection device according to the preset program. Optionally, the touch panel may comprise two parts, i.e., a touch detection device and a touch controller, wherein the touch detection device detects the user's touch orientation, and detects the signal brought by the touch operation to transmit the signal to the touch controller; and the touch controller receives the touch information from the touch detection device, converts it into the contact coordinates and then sends them to the processor 811, and can receive and implement the command from the processor 811. In addition, the touch panel may be realized in many types, such as resistance, capacitance, infrared and surface acoustic wave. In addition to the touch panel, the input unit 814 may also comprise other input devices. Specifically, other input devices may include but are not limited to one or more of physical keyboard, function keys (such as volume control keys or switch keys), trackball, mouse, joystick, etc.

The communication unit 815 may be configured to receive and transmit signals. In particular, the downlink information of the cloud device is received and sent to the processor 811 for processing; and in addition, the uplink data is sent to the cloud device.

The display unit 816 may be configured to display information inputted by or provided to the user, and various menus of the terminal device. The display unit 816 may comprise a display panel. Optionally, the display panel may be configured in the form of a liquid crystal display (LCD), an organic light-emitting diode (OLED), etc. Optionally, the touch panel may cover the display panel. When the touch panel detects a touch operation on or near the touch panel, it transmits the touch operation to the processor 811 to determine the type of the touch event, and then the processor 811 provides the corresponding visual output on the display panel according to the type of the touch event. Although in the drawings, the touch panel and the display panel are used as two independent components to realize the input and output functions of the terminal device, the touch panel and the display panel in some embodiments may be integrated to realize the input and output functions of the terminal device.

Optionally, the memory 813 is used to store at least one program, which is controlled and executed by the processor 811. The processor 811 is configured to execute at least one program code stored in the memory 813 to receive the actual human body parameters inputted by the user through the input unit 814 and send the received actual human body parameters of the user to the cloud device through the communication unit 815; and when the personalized variable human body model corresponding to the actual human parameter returned by the cloud device is received, the display unit 816 is used to display the personalized variable human body model.

The cloud device 820 as shown in FIG. 25 comprises a processor 821, a bus 822, a memory 823, and a communication unit 824. The processor 821 has better computing power than the processor 811 in the terminal device 810. The bus 822, the memory 823 and the communication unit 824 are identical or similar to the bus 812, the memory 813 and the communication unit 815 in the terminal device 810, which will not be reiterated.

Optionally, the memory 823 is configured to store at least one program, which is controlled and executed by the processor 821. The processor 821 is configured to when receiving the user's actual human body parameter sent from the terminal device 810 through the communication unit 824, execute at least one program code stored in the memory 823 to generate a personalized variable human body model corresponding to the actual human body parameter and then return the same to the terminal device 810 through the communication unit 824, by means of any of the above processing methods of the variable human body model of the present disclosure.

Based on the same inventive concept, the exemplary embodiment of the present disclosure provides a computer-readable storage medium on which a computer program is stored. When the computer program is executed by a processor, any human body information display method and/or human body model generation method provided by the embodiment of the present disclosure are/is realized.

The computer storage medium includes, but is not limited to, any type of disks (including a floppy disk, hard disk, optical disk, CD-ROM, and magnetic disk), ROM, RAM, erasable programmable read-only memory (EPROM), EEPROM, flash memory, magnetic card or light card. That is, the readable medium includes any medium with which the device (e.g., a computer) stores or transmits information in a readable form.

The computer storage medium provided by the embodiment of the present disclosure is similar to the implementation principle of the previous embodiments. Reference can be made to the previous embodiments for the contents not shown in detail with respect to the computer storage medium, which will not be reiterated.

The human body model generation method according to the exemplary embodiment of the present disclosure can achieve at least the following advantageous effects:

1) In the embodiment of the present disclosure, the typical variable human body model in the variable human body model library is obtained by big data calculation based on a large number of real sample human body data. The diversity and authenticity of samples can ensure that the typical variable human body model is highly precise, and therefore the personalized variable human body model obtained by processing the typical variable human body model is highly precise; and compared with the conventional statistical calculation method, the method of the present disclosure can greatly reduce the amount of calculation, decrease costs, and shorten the processing time, such that a hardware device with common processing power may also apply the personalized variable human body model processing method provided by the embodiment of the present disclosure, thereby broadening its application scope.

2) The embodiment of the present disclosure can determine the principal shape change components and shape change characteristic values reflecting the shape change rules of each actual human body model through the principal component analysis method, and determine the typical variable human body model based on the principal shape change components and shape change characteristic values. For the shape change characteristic values, the embodiment of the present disclosure can select the largest part of the shape change characteristic values for calculation and exclude some invalid or inefficient data so as to reduce the amount of calculation and improve the efficiency of constructing the typical variable human body model and personalized variable human body model on the premise of extracting the principal influencing factors and still maintaining the high authenticity of the model.

3) The embodiment of the present disclosure can determine the typical human body parameter by determining the physical sign characteristic value of the human body physical sign data, and construct the corresponding typical variable human body model, so that the typical variable human body model can reflect the shape change characteristics of the human body. When determining the typical human body parameter, consideration may be given to the influences between different human body physical sign data, and the human body physical sign data in the typical human body parameter may be determined based on the mapping relationship between different human body physical sign data, so that the typical human body parameter obtained can reflect the human body characteristics more accurately.

4) When establishing a personalized human body model based on the actual human body parameter, the embodiment of the present disclosure may precisely match the typical variable human body model according to the parameter class of the actual human body parameter, and determine the model weight coefficient, and further properly modify the precisely matched typical variable human body model to obtain a personalized variable human body model that complies with the user's body characteristics. Even if the target user's body shape is abnormal, it can also achieve highly restored personalized customization and provide a real and reliable personalized variable human body model.

5) The technical solution of the embodiment of the present disclosure can realize real-time interaction with users, and has a wide range of application, which can be applied to both terminal devices and the overall architecture of terminal devices and cloud devices.

Those skilled in the art can understand that the steps, measures and solutions in various operations, methods, and processes that have been discussed in the present disclosure can be substituted, changed, combined or deleted. Further, other steps, measures and solutions in various operations, methods and processes that have been discussed in the present disclosure can also be substituted, changed, rearranged, decomposed, combined or deleted. Further, the steps, measures, and schemes in various operations, methods and processes disclosed in the present disclosure and in the related art can also be substituted, changed, rearranged, decomposed, combined or deleted.

It should be understood that although the steps in the flow chart of the drawing are shown in the order indicated by the arrow, these steps are not necessarily performed in the order indicated by the arrow. Unless explicitly stated, there are no strict limits to the order of executing these steps, which can be executed in other orders. Moreover, at least part of the steps in the flow chart of the drawing may include a plurality of sub-steps or stages. These sub-steps or stages are not necessarily executed at the same time, but can be executed at different times, and the execution order is not necessarily sequential, but can be executed sequentially or alternately with other steps or at least part of the sub-steps or stages of other steps.

The above are only part of the embodiments of the present disclosure. It should be pointed out that for those of ordinary skill in the art, without departing from the principle of the present disclosure, several improvements and modifications can be made, and these improvements and modifications should also be regarded as falling within the scope of protection of the present disclosure.

What is claimed is:

1. A health management system, comprising:
a health assessment module configured to obtain health parameter information related to human body health of a user, and generate a health status assessment result of the user based on the health parameter information;
a health intervention module configured to generate a health management scheme of the user based on the health status assessment result;
a human body model generation module configured to generate a three-dimensional human body model displayable on a display interface;
a human body information display module configured to:
obtain at least one first display instruction each corresponding to one human body system model of a plurality of human body system models medically classified according to human body systems;
display, on the display interface, the three-dimensional human body model in the form of layers based on the human body system model corresponding to the at least one first display instruction;
provide a human body prominently-displayed area on the three-dimensional human body model, wherein the human body prominently-displayed area is a circular area overlapping onto the three-dimensional human body model, and the circular area is slidable along the three-dimensional human body model;
display the three-dimensional human body model's portion that is overlapping with the circular area in the form of layers based on corresponding human body system models, and keep the three-dimensional human body model's all portions that are not overlapping with the circular area displayed in an unchanged manner.

2. The health management system according to claim 1, wherein the human body information display module is further configured to:
obtain at least one second display instruction each corresponding to one tissue layer model of a plurality of tissue layer models medically classified according to human body tissue layers;

display, on the display interface, the three-dimensional human body model in the form of layers based on the tissue layer model corresponding to the at least one second display instruction.

3. The health management system according to claim 1, wherein the human body information display module is further configured to:

obtain at least one third display instruction each corresponding to one local three-dimensional human body model of a plurality of local three-dimensional human body models medically classified according to human body parts;

display, on the display interface, the three-dimensional human body model in the form of layers based on the local three-dimensional human body model corresponding to the at least one third display instruction.

4. The health management system according to claim 1, wherein the first display instruction is obtained by at least one of the following manners:

an optional menu displayed on the display interface;

touch information of different predetermined areas on the display interface;

received preset voice information.

5. The health management system according to claim 1, wherein the human body information display module is further configured to:

display at least one human body information tag on the display interface;

in response to a trigger instruction for a human body information tag, prominently display, on the display interface, human body information and a human body system model corresponding to the human body information tag.

6. The health management system according to claim 5, wherein the human body information corresponding to the human body information tag comprises at least one of the group comprising: human body organ category information, human body system category information, human body parameter information and health parameter information.

7. The health management system according to claim 1, wherein a shape and/or a size of the human body prominently-displayed area can be changed, as the human body prominently-displayed area is moved on the three-dimensional human body model.

8. The health management system according to claim 1, wherein the human body information display module is further configured to:

display at least one human body information tag on the display interface;

in response to a trigger instruction for a human body information tag, move the human body prominently-displayed area to the three-dimensional human body model's portion corresponding to the human body information tag, and display the three-dimensional human body model's portion corresponding to the human body information tag in the form of layers based on a corresponding human body system model.

9. The health management system according to claim 1, wherein the human body information display module is further configured to:

obtain touch information on the display interface, the touch information comprising at least one of the group comprising: a contact position, a contact area, a contact duration or continuous contact information, the continuous contact information comprising start-point position contact information and end-point position contact information;

update and display the three-dimensional human body model according to the touch information.

10. The health management system according to claim 9, wherein updating and displaying the three-dimensional human body model according to the touch information comprises:

determining the contact position and the contact duration according to the touch information;

magnifying the three-dimensional human body model by a predetermined multiple with the contact position as a centre when the contact duration is larger than a preset trigger duration;

displaying the three-dimensional human body model that is magnified on the display interface.

11. The health management system according to claim 9, wherein updating and displaying the three-dimensional human body model according to the touch information comprises:

determining deflection displacement according to the touch information;

rotating the three-dimensional human body model according to the deflection displacement;

displaying the three-dimensional human body model that is rotated on the display interface.

12. The health management system according to claim 1, wherein the health assessment module is further configured to identify a physical examination report of the user to obtain the health parameter information related to the human body health of the user.

13. The health management system according to claim 12, wherein identifying a physical examination report of the user comprises:

performing OCR recognition of a PDF file or an image of the physical examination report of the user;

scanning and identifying a paper document of the physical examination report of the user.

14. The health management system according to claim 1, wherein the health assessment module is further configured to conduct information research for the user in the form of questionnaire.

15. The health management system according to claim 1, wherein at least one of the health assessment module and the health intervention module is configured to monitor physiological indicators reflecting the health status of the user.

16. The health management system according to claim 1, wherein at least one of the health assessment module and the health intervention module is further configured to push a message to the user.

17. The health management system according to claim 1, wherein the human body model generation module is further configured to generate a personalized three-dimensional human body model according to actual human body parameters of the user.

* * * * *